US010982013B2

(12) United States Patent
Ayoub et al.

(10) Patent No.: US 10,982,013 B2
(45) Date of Patent: Apr. 20, 2021

(54) MODIFIED BIOPOLYMERS AND METHODS OF PRODUCING AND USING THE SAME

(71) Applicant: Anavo Technologies, LLC, Raleigh, NC (US)

(72) Inventors: Ali Ayoub, Raleigh, NC (US); James Charles Bray, Raleigh, NC (US); Ryan Nicholas Chan, Cary, NC (US)

( * ) Notice: Subject to any disclaimer, the term of this patent is extended or adjusted under 35 U.S.C. 154(b) by 0 days.

(21) Appl. No.: 14/728,240

(22) Filed: Jun. 2, 2015

(65) Prior Publication Data
US 2017/0002098 A1   Jan. 5, 2017

Related U.S. Application Data

(60) Provisional application No. 62/006,317, filed on Jun. 2, 2014.

(51) Int. Cl.
| C08B 31/06 | (2006.01) |
| C08B 31/12 | (2006.01) |
| C08B 31/00 | (2006.01) |
| C08B 37/00 | (2006.01) |
| C08H 1/00 | (2006.01) |
| C08B 37/08 | (2006.01) |
| B01J 39/19 | (2017.01) |
| C08B 31/04 | (2006.01) |
| A61L 15/28 | (2006.01) |
| A61L 15/32 | (2006.01) |
| A61L 15/42 | (2006.01) |
| A61L 15/60 | (2006.01) |
| B01J 39/22 | (2006.01) |
| C08B 15/00 | (2006.01) |
| B27N 3/28 | (2006.01) |

(52) U.S. Cl.
CPC ............ C08B 31/003 (2013.01); A61L 15/28 (2013.01); A61L 15/32 (2013.01); A61L 15/425 (2013.01); A61L 15/60 (2013.01); B01J 39/19 (2017.01); B01J 39/22 (2013.01); C08B 15/005 (2013.01); C08B 31/006 (2013.01); C08B 31/04 (2013.01); C08B 31/063 (2013.01); C08B 31/066 (2013.01); C08B 31/12 (2013.01); C08B 37/003 (2013.01); C08B 37/0045 (2013.01); C08B 37/0057 (2013.01); C08H 1/00 (2013.01); A61L 2400/04 (2013.01); B27N 3/28 (2013.01)

(58) Field of Classification Search
CPC .................................................... C08B 31/00
USPC ........................................................ 536/106
See application file for complete search history.

(56) References Cited

U.S. PATENT DOCUMENTS

| 3,884,853 A | 5/1975 | Zimmerman |
| 3,932,322 A | 1/1976 | Duchane |
| 4,043,952 A | 8/1977 | Ganslaw et al. |
| 4,060,683 A | 11/1977 | Tessler |
| 4,090,013 A | 5/1978 | Ganslaw et al. |
| 4,098,997 A | 7/1978 | Tessler |
| 4,111,810 A | 9/1978 | Arai et al. |
| 4,127,944 A | 12/1978 | Giacobello |
| 4,129,722 A | 12/1978 | Iovine et al. |
| 4,131,576 A | 12/1978 | Iovine et al. |
| 4,219,646 A | 8/1980 | Rubens |
| 4,232,674 A * | 11/1980 | Melican ................. A61F 13/206 604/369 |
| 4,237,271 A * | 12/1980 | Rayford .................. C08B 31/12 536/106 |
| 4,256,111 A | 3/1981 | Lassen |
| 4,278,573 A | 7/1981 | Tessler |
| 4,454,055 A | 6/1984 | Richman et al. |
| 4,590,081 A * | 5/1986 | Sawada .................... A23G 1/10 426/448 |
| 4,654,039 A | 3/1987 | Brandt et al. |
| 4,725,628 A | 2/1988 | Garvey et al. |
| 4,725,629 A | 2/1988 | Garvey et al. |
| 4,731,391 A | 3/1988 | Garvey |
| 4,820,577 A | 4/1989 | Morman et al. |
| 4,853,168 A | 8/1989 | Eden et al. |
| 4,876,336 A | 10/1989 | Solarek et al. |
| 4,964,953 A | 10/1990 | Solarek et al. |
| 5,079,354 A | 1/1992 | Gross et al. |
| 5,122,231 A | 6/1992 | Anderson |
| 5,130,391 A | 7/1992 | Ahmed et al. |
| 5,176,635 A * | 1/1993 | Dittmann ............. A61K 9/0019 206/219 |
| 5,190,563 A | 3/1993 | Herron et al. |
| 5,216,098 A | 6/1993 | Ahmed et al. |
| 5,227,481 A | 7/1993 | Tsai et al. |
| 5,252,690 A | 10/1993 | Ahmed et al. |

(Continued)

FOREIGN PATENT DOCUMENTS

| CA | 2783361 A1 * 7/2011 ............. B65D 47/08 |
| CN | 103435708       12/2013 |

(Continued)

OTHER PUBLICATIONS

International Search Report and the Written Opinion of the International Searching Authority Corresponding to International Patent Application No. PCT/US2015/033688 (14 pages) (dated Sep. 9, 2015).

Alqnso et al. "Cross-linking chitosan into UV-irradiated cellulose fibers for the preparation of antimicrobial-finished textiles" *Carbohydrate Polymers* 77:536-543 (2009).

Baran et al. "Starch-chitosan hydrogels prepared by reductive alkylation cross-linking" *Journal of Materials Science: Materials in Medicine* 15:759-765 (2004).

Bernabe et al. "Swelling behavior of chitosan/pectin polyelectrolyte complex membranes. Effect of thermal cross-linking" *Polymer Bulletin* 55:367-375 (2005).

(Continued)

Primary Examiner — Eric Olson
(74) *Attorney, Agent, or Firm* — Myers Bigel, P.A.

(57) ABSTRACT

Modified biopolymers, such as, charge-modified biopolymers, cross-linked biopolymers, and cross-linked, charge-modified biopolymers are provided along with methods of producing and using the same.

50 Claims, 7 Drawing Sheets

(56) References Cited

U.S. PATENT DOCUMENTS

| | | |
|---|---|---|
| 5,286,827 A | 2/1994 | Ahmed |
| 5,314,420 A | 5/1994 | Smith et al. |
| 5,340,853 A | 8/1994 | Chmelir et al. |
| 5,349,089 A | 9/1994 | Tsai et al. |
| 5,422,183 A | 6/1995 | Sinclair et al. |
| 5,422,387 A | 6/1995 | Toms et al. |
| 5,451,613 A | 9/1995 | Smith et al. |
| 5,462,972 A | 10/1995 | Sinith et al. |
| 5,470,964 A | 11/1995 | Qin |
| 5,498,705 A | 3/1996 | Oin |
| 5,506,277 A | 4/1996 | Griesbach, III |
| 5,563,179 A | 10/1996 | Stone et al. |
| 5,583,193 A | 12/1996 | Aravindakshan et al. |
| 5,597,784 A | 1/1997 | Sinclair et al. |
| 5,599,916 A | 2/1997 | Dutkiewicz et al. |
| 5,629,416 A | 5/1997 | Neigel et al. |
| 5,711,908 A | 1/1998 | Tiefenbacher et al. |
| 5,721,295 A | 2/1998 | Brüggemann et al. |
| 5,736,595 A | 4/1998 | Günther et al. |
| 5,767,168 A | 6/1998 | Dyer et al. |
| 5,797,984 A | 8/1998 | Billmers et al. |
| 5,847,031 A | 12/1998 | Klimmek et al. |
| 5,849,233 A | 12/1998 | Altieri |
| 5,851,959 A | 12/1998 | Bernu |
| 5,929,437 A | 7/1999 | Elliott et al. |
| 5,958,589 A | 9/1999 | Glenn et al. |
| 6,114,410 A | 9/2000 | Betzold |
| 6,153,305 A | 11/2000 | Uemura et al. |
| 6,193,843 B1 | 2/2001 | Tsai et al. |
| 6,197,951 B1 | 3/2001 | Lenz |
| 6,225,406 B1 | 5/2001 | Wang et al. |
| 6,235,835 B1 | 5/2001 | Niessner et al. |
| 6,294,180 B1 | 9/2001 | Demars et al. |
| 6,299,969 B1 | 10/2001 | Altieri et al. |
| 6,328,105 B1 | 12/2001 | Betzold |
| 6,372,678 B1 | 4/2002 | Youngman et al. |
| 6,380,456 B1 | 4/2002 | Goldman |
| 6,444,653 B1 | 9/2002 | Huppé et al. |
| 6,488,980 B1 | 12/2002 | Jeffcoat et al. |
| 6,500,947 B1 | 12/2002 | West et al. |
| 6,506,873 B1 | 1/2003 | Ryan et al. |
| 6,517,678 B1 | 2/2003 | Shannon et al. |
| 6,585,859 B1 | 7/2003 | Håkansson |
| 6,607,748 B1 | 8/2003 | Lenaerts et al. |
| 6,620,295 B2 | 9/2003 | Shannon et al. |
| 6,670,470 B1 | 12/2003 | Ketola et al. |
| 6,689,934 B2 | 2/2004 | Dodge, II et al. |
| 6,706,944 B2 | 3/2004 | Qin et al. |
| 6,713,460 B2 | 3/2004 | Huppé et al. |
| 6,746,542 B1 | 6/2004 | Lorencak et al. |
| 6,755,915 B1 | 6/2004 | Van Soest et al. |
| 6,765,042 B1 | 7/2004 | Thornton et al. |
| 6,767,430 B1 * | 7/2004 | Wielema ............... C08B 31/003 |
| | | 162/175 |
| 6,825,252 B2 | 11/2004 | Helbling et al. |
| 6,844,430 B2 | 1/2005 | Pesce et al. |
| 6,855,434 B2 | 2/2005 | Romasn-Hess et al. |
| 6,867,287 B2 | 3/2005 | Carlucci et al. |
| 6,939,914 B2 | 9/2005 | Qin et bl |
| 6,951,933 B2 | 10/2005 | West et al. |
| 7,009,020 B2 | 3/2006 | Doane et al. |
| 7,101,426 B2 | 9/2006 | Tagge et al. |
| 7,153,354 B2 | 12/2006 | Narayan et al. |
| 7,153,553 B2 | 12/2006 | Tetrault |
| 7,244,492 B2 | 7/2007 | Sinclair et al. |
| 7,285,586 B2 | 10/2007 | Helbling et al. |
| 7,294,343 B2 | 11/2007 | Barresi et al. |
| 7,297,395 B2 | 11/2007 | Kainth et al. |
| 7,365,190 B2 | 4/2008 | Couture et al. |
| 7,419,808 B2 * | 9/2008 | Zhang ....................... C12N 7/00 |
| | | 424/184.1 |
| 7,423,090 B2 | 9/2008 | Doane et al. |
| 7,423,106 B2 | 9/2008 | Doane et al. |
| 7,425,595 B2 | 9/2008 | Savich et al. |
| 7,459,501 B2 | 12/2008 | Doane et al. |
| 7,524,379 B2 | 4/2009 | Bailey et al. |
| 7,560,419 B2 | 7/2009 | Fang et al. |
| 7,575,618 B2 | 8/2009 | Miao et al. |
| 7,591,974 B2 | 9/2009 | Savich et al. |
| 7,607,259 B2 | 10/2009 | Savich |
| 7,622,428 B2 | 11/2009 | Huff et al. |
| 7,732,525 B2 | 6/2010 | Branston et al. |
| 7,807,271 B2 | 10/2010 | Branston et al. |
| 7,833,384 B2 | 11/2010 | Weerawarna |
| 7,842,164 B2 | 11/2010 | Rasheed et al. |
| 7,932,378 B2 | 4/2011 | Mikkonen et al. |
| 7,959,762 B2 | 6/2011 | Weerawarna |
| 7,985,742 B2 | 7/2011 | Bergeron |
| 7,985,794 B2 | 7/2011 | Narayan et al. |
| 7,994,384 B2 | 8/2011 | Qin et al. |
| 8,017,249 B2 | 9/2011 | Tippit |
| 8,017,553 B2 | 9/2011 | Doane et al. |
| 8,076,279 B2 | 12/2011 | Brand et al. |
| 8,076,473 B2 | 12/2011 | Berckmans et al. |
| 8,084,391 B2 | 12/2011 | Weerawarna |
| 8,101,543 B2 | 1/2012 | Weerawarna |
| 8,114,809 B2 | 2/2012 | Chevigny et al. |
| 8,163,309 B2 | 4/2012 | Glenn et al. |
| 8,192,660 B2 | 6/2012 | Wang et al. |
| 8,263,163 B2 | 9/2012 | Wang et al. |
| 8,268,989 B2 | 9/2012 | English et al. |
| 8,361,926 B2 | 1/2013 | Tian et al. |
| 8,362,089 B2 | 1/2013 | Hashimoto |
| 8,383,573 B2 * | 2/2013 | Dupont ................ C11D 3/0036 |
| | | 510/276 |
| 8,431,619 B2 | 4/2013 | Hashimoto |
| 8,434,498 B2 | 5/2013 | Sebastian |
| 8,436,056 B2 | 5/2013 | Barati |
| 8,442,820 B2 * | 5/2013 | Kim ................ G06K 9/00335 |
| | | 704/231 |
| 8,444,819 B2 | 5/2013 | Anderson et al. |
| 8,461,129 B2 | 6/2013 | Bolduc et al. |
| 8,481,717 B2 | 7/2013 | Trksak |
| 8,486,854 B2 | 7/2013 | Berrada et al. |
| 8,486,855 B2 | 7/2013 | Tian et al. |
| 8,507,666 B2 | 8/2013 | Skuratowicz |
| RE44,519 E | 10/2013 | Anderson et al. |
| 8,545,691 B2 | 10/2013 | Teymour et al. |
| 8,563,466 B2 | 10/2013 | Chevigny et al. |
| 8,580,953 B2 | 11/2013 | Frank et al. |
| 8,613,971 B2 | 12/2013 | Finocchiaro et al. |
| 8,623,341 B2 | 1/2014 | Peffly et al. |
| 8,641,869 B2 | 2/2014 | Weerawarna |
| 8,686,132 B2 | 4/2014 | Berckmans et al. |
| 8,703,645 B2 | 4/2014 | Tian et al. |
| 8,710,212 B2 | 4/2014 | Thibodeau et al. |
| 8,759,511 B2 | 6/2014 | English et al. |
| 8,785,417 B2 | 7/2014 | Couffin et al. |
| 8,795,834 B2 | 8/2014 | Tetrault et al. |
| 8,815,008 B2 | 8/2014 | Drake et al. |
| 8,815,135 B2 | 8/2014 | Beecher et al. |
| 8,829,107 B2 | 9/2014 | Furno et al. |
| 8,852,682 B2 | 10/2014 | Sinclair et al. |
| 8,859,758 B2 | 10/2014 | Frank et al. |
| 8,926,794 B2 | 1/2015 | Han et al. |
| 8,951,594 B2 | 2/2015 | Wang et al. |
| 8,962,092 B2 | 2/2015 | Trksak et al. |
| 8,975,387 B1 | 2/2015 | Venditti et al. |
| 8,993,039 B2 | 3/2015 | Harrison et al. |
| 9,011,741 B2 | 4/2015 | Wildi et al. |
| 9,039,924 B2 | 5/2015 | Leavitt et al. |
| 9,078,947 B2 | 7/2015 | MacDonald et al. |
| 9,107,975 B2 | 8/2015 | Godin et al. |
| 9,149,787 B1 | 10/2015 | Godin et al. |
| 9,296,655 B2 | 3/2016 | Mann et al. |
| 9,297,244 B2 | 3/2016 | Mahoney et al. |
| 9,315,721 B2 | 4/2016 | Mahoney et al. |
| 9,932,521 B2 | 4/2018 | Soane et al. |
| 2001/0015267 A1 | 8/2001 | Pauley et al. |
| 2001/0040136 A1 * | 11/2001 | Wei ...................... B01D 39/1607 |
| | | 210/767 |
| 2002/0039869 A1 | 4/2002 | Achille |
| 2002/0110875 A1 | 8/2002 | Bazin et al. |
| 2002/0156048 A1 | 10/2002 | Huppé et al. |

(56) References Cited

U.S. PATENT DOCUMENTS

| | | |
|---|---|---|
| 2003/0020043 A1 | 1/2003 | Barresi et al. |
| 2003/0027787 A1 | 2/2003 | Couture et al. |
| 2003/0176293 A1 | 9/2003 | Schilling et al. |
| 2003/0202996 A1 | 10/2003 | Bazin et al. |
| 2004/0086541 A1 | 5/2004 | Barresi et al. |
| 2004/0091324 A1 | 5/2004 | Schilling et al. |
| 2004/0091977 A1 | 5/2004 | Teeri et al. |
| 2004/0124013 A1 | 7/2004 | Wiesner et al. |
| 2004/0140584 A1 | 7/2004 | Wang et al. |
| 2005/0214541 A1 | 9/2005 | Berrada et al. |
| 2005/0260316 A1 | 11/2005 | Wang et al. |
| 2006/0018939 A1 | 1/2006 | Bazin et al. |
| 2006/0045912 A1 | 3/2006 | Truog |
| 2006/0062990 A1 | 3/2006 | Gotoh |
| 2006/0172092 A1 | 8/2006 | Tetrault |
| 2006/0182944 A1 | 8/2006 | Leavitt et al. |
| 2006/0276569 A1 | 12/2006 | Hernandez et al. |
| 2007/0042473 A1 | 2/2007 | Bazin et al. |
| 2007/0059432 A1 | 3/2007 | Norman et al. |
| 2007/0089734 A1 | 4/2007 | Stanley et al. |
| 2007/0110962 A1 | 5/2007 | Tien et al. |
| 2007/0179291 A1 | 8/2007 | Thibodeau et al. |
| 2007/0275155 A1 | 11/2007 | Nehmer et al. |
| 2008/0051494 A1 | 2/2008 | Savich et al. |
| 2008/0082067 A1 | 4/2008 | Weerawarna et al. |
| 2008/0110816 A1 | 5/2008 | Leavitt et al. |
| 2008/0177057 A1 | 7/2008 | Bolduc et al. |
| 2008/0207431 A1 | 8/2008 | Townley et al. |
| 2008/0226722 A1 | 9/2008 | Van Tomme et al. |
| 2008/0261807 A1 | 10/2008 | Chevigny et al. |
| 2008/0305950 A1 | 12/2008 | Berrada |
| 2009/0044941 A1 | 2/2009 | De Paiva Cortes et al. |
| 2009/0304835 A1 | 12/2009 | Savich et al. |
| 2010/0032367 A1 | 2/2010 | Leavitt et al. |
| 2010/0036337 A1 | 2/2010 | Couffin et al. |
| 2010/0042063 A1 | 2/2010 | Couffin et al. |
| 2010/0057027 A1 | 3/2010 | Furno et al. |
| 2010/0147760 A1 | 6/2010 | Leavitt et al. |
| 2010/0203265 A1 | 8/2010 | Tetrault et al. |
| 2010/0221402 A1 | 9/2010 | Wang et al. |
| 2010/0221406 A1 | 9/2010 | Norman et al. |
| 2010/0252031 A1 | 10/2010 | Stanley et al. |
| 2010/0311687 A1 | 12/2010 | Bosco et al. |
| 2010/0311904 A1 | 12/2010 | Chambers |
| 2011/0095227 A1 | 4/2011 | Herth et al. |
| 2011/0120719 A1 | 5/2011 | Soane et al. |
| 2011/0183380 A1 | 7/2011 | El-Tahlawy et al. |
| 2012/0065604 A1 | 3/2012 | Chang et al. |
| 2012/0121519 A1* | 5/2012 | Thomaides ............ A61K 8/732 424/43 |
| 2012/0125231 A1 | 5/2012 | Markland et al. |
| 2012/0138848 A1 | 6/2012 | Leavitt et al. |
| 2012/0142525 A1 | 6/2012 | Chevigny et al. |
| 2012/0258811 A1 | 10/2012 | Tetrault et al. |
| 2012/0266869 A1 | 10/2012 | Wang et al. |
| 2012/0328723 A1 | 12/2012 | Savich et al. |
| 2013/0011885 A1 | 1/2013 | Binder et al. |
| 2013/0174993 A1 | 7/2013 | Medhekar et al. |
| 2013/0203983 A1 | 8/2013 | English et al. |
| 2013/0233545 A1 | 9/2013 | Mahoney et al. |
| 2013/0251996 A1 | 9/2013 | Ji et al. |
| 2013/0289267 A1 | 10/2013 | Weisser et al. |
| 2013/0296543 A1 | 11/2013 | Hanna et al. |
| 2013/0303714 A1 | 11/2013 | Chambers |
| 2014/0000891 A1 | 1/2014 | Mahoney et al. |
| 2014/0005280 A1 | 1/2014 | Assaad et al. |
| 2014/0014348 A1 | 1/2014 | Mahoney et al. |
| 2014/0060832 A1 | 3/2014 | Mahoney et al. |
| 2014/0158355 A1 | 6/2014 | Wuthrich et al. |
| 2014/0212589 A1 | 7/2014 | Trksak et al. |
| 2014/0228258 A1 | 8/2014 | Mahoney et al. |
| 2014/0309410 A1* | 10/2014 | Haider .................... B01J 20/24 536/20 |
| 2014/0322459 A1 | 10/2014 | Tetrault et al. |
| 2014/0335040 A1* | 11/2014 | Yu ........................ A61K 8/4933 424/70.28 |
| 2015/0201653 A1 | 7/2015 | Yildiz et al. |
| 2015/0252252 A1 | 9/2015 | Soane et al. |
| 2015/0252253 A1 | 9/2015 | Soane et al. |
| 2015/0299431 A1 | 10/2015 | Parcq et al. |
| 2016/0137913 A1 | 5/2016 | Mahoney et al. |
| 2016/0200966 A1 | 7/2016 | Mahoney et al. |
| 2016/0200967 A1 | 7/2016 | Mahoney et al. |
| 2016/0298026 A1 | 10/2016 | Aboushabana et al. |
| 2017/0058191 A1 | 3/2017 | Mahoney et al. |
| 2017/0335178 A1 | 11/2017 | Aboushabana et al. |

FOREIGN PATENT DOCUMENTS

| | | | |
|---|---|---|---|
| EP | 0 257 338 A2 | 3/1988 | |
| EP | 1 390 412 B1 | 2/2004 | |
| EP | 1 649 851 A2 | 4/2006 | |
| EP | 1674502 | 6/2006 | |
| EP | 1 812 477 A2 | 8/2007 | |
| EP | 1 897 893 A1 | 3/2008 | |
| EP | 1 939 219 A1 | 7/2008 | |
| GB | 1183623 | 3/1970 | |
| WO | WO 96/23104 A1 | 8/1996 | |
| WO | WO 97/46591 A1 | 12/1997 | |
| WO | WO 99/12977 A1 | 3/1999 | |
| WO | WO 00/49226 A1 | 8/2000 | |
| WO | WO0049226 * | 8/2000 | ............ D21H 17/28 |
| WO | WO 01/79301 A1 | 10/2001 | |
| WO | WO 02/02084 A1 | 1/2002 | |
| WO | WO 02/274814 A1 * | 9/2002 | |
| WO | WO 02/087868 A1 | 11/2002 | |
| WO | WO 03/033813 A1 | 4/2003 | |
| WO | WO 03/040055 A1 | 5/2003 | |
| WO | WO 03/074787 A1 | 9/2003 | |
| WO | WO 2004/076551 A1 | 9/2004 | |
| WO | WO 2004/085481 A1 | 10/2004 | |
| WO | 2005030845 | 4/2005 | |
| WO | WO 2005/113616 A2 | 12/2005 | |
| WO | WO 2005/113894 A1 | 12/2005 | |
| WO | WO 2006/014416 A1 | 2/2006 | |
| WO | WO 2006/023825 A1 | 3/2006 | |
| WO | WO 2006/032929 A1 | 3/2006 | |
| WO | WO 2006/037157 A1 | 4/2006 | |
| WO | WO 2006/042364 A1 | 4/2006 | |
| WO | WO 2006/053847 A1 | 5/2006 | |
| WO | WO 2006/055504 A2 | 5/2006 | |
| WO | WO 2006/055505 A2 | 5/2006 | |
| WO | WO 2006/124871 A1 | 11/2006 | |
| WO | WO 20071035099 A1 | 3/2007 | |
| WO | WO 2007/071776 A1 | 6/2007 | |
| WO | WO 2007/080539 A2 | 7/2007 | |
| WO | WO 2007/086803 A1 | 8/2007 | |
| WO | WO 2007/126603 A2 | 11/2007 | |
| WO | WO 2008/022127 A2 | 2/2008 | |
| WO | WO 2008/081257 A2 | 7/2008 | |
| WO | WO 2009/073197 A1 | 6/2009 | |
| WO | WO 2009/094421 A1 | 7/2009 | |
| WO | WO 2009/143119 A2 | 11/2009 | |
| WO | WO 2010/051151 A2 | 5/2010 | |
| WO | WO 2010/065750 A1 | 6/2010 | |
| WO | WO 2010/148357 A1 | 12/2010 | |
| WO | WO 2011/019646 A1 | 2/2011 | |
| WO | WO 2011/029518 A1 | 3/2011 | |
| WO | WO 2012/064741 A2 | 5/2012 | |
| WO | WO 2012/097447 A1 | 7/2012 | |
| WO | WO 2012/162845 A1 | 12/2012 | |
| WO | 2013/033391 | 3/2013 | |
| WO | WO 2013/042083 A1 | 3/2013 | |
| WO | WO 2013/096891 A1 | 6/2013 | |
| WO | WO 2013/116945 A1 | 8/2013 | |
| WO | WO 2013/158945 A1 | 10/2013 | |
| WO | WO 2013/180643 A1 | 12/2013 | |
| WO | WO 2014/029029 A1 | 2/2014 | |
| WO | WO 2014/043808 A1 | 3/2014 | |

(56) References Cited

FOREIGN PATENT DOCUMENTS

| WO | 2015/047116 | 4/2015 |
|----|-------------|--------|
| WO | 2015/130278 | 9/2015 |

OTHER PUBLICATIONS

Demitri et al. "Novel Superabsorbent Cellulose-Based Hydrogels Crosslinked with Citric Acid" *Journal of Applied Polymer Science* 110:2453-2460 (2008).

Edlund et al. "A Microspheric System: Hemicellulose-based Hydrogels" *Journal of Bioactive and Compatible Polymers* 23:171-186 (2008).

El-Tahlawy et al. "The antimicrobial activity of cotton fabrics treated with different crosslinking agents and chitosan" *Carbohydrate Polymers* 60:421-430 (2005).

El-Tahlawy et al. "Aspects of the preparation of starch microcellular foam particles crosslinked with glutaraldehyde using a solvent exchange technique" *Carbohydrate Polymers* 67(3):319-331 (2007).

Gabrielii et al. "Preparation and Properties of Hydrogels Based on Hemicellulose" *Journal of Applied Polymer Science* 69(8):1661-1667 (1998).

Gabrielii et al. "Separation, characterization and hydrogel-formation of hemicellulose from aspen wood" *Carbohydrate Polymers* 43(4):367-374 (2000).

Gaffar, Mohammed A. "Preparation and Utilization of New Carboxyl Group Containing Cation Exchangers Based on Starch Using a Dry Reaction Method" *Starch* 54:185-192 (2002).

Heinze et al. "Starch derivatives of high degree of functionalization 9: carboxymethyl starches" *Cellulose* 11:239-245 (2004).

Helander et al. "Chitosan disrupts the barrier properties of the outer membrane of gram-negative bacteria" *International Journal of Food Microbiology* 71(2):235-244 (2001).

Jain et al. "Thermoplastic xylan derivatives with propylene oxide" *Cellulose* 7:319-336 (2001).

Kema et al. "Wet-milling/Ammonia Process for the Manufacture of Wheat Starch and Gluten" *Starch* 48:279-285 (1996).

Kiatkamjornwong, Suda "Superabsorbent Polymers and Superabsorbent Polymer Compositions" *ScienceAsia* 33(Supplement 1):39-43 (2007).

Kumar, Majeti N.V. Ravi "A review of chitin and chitosan applications" *Reactive & Functional Polymers* 46:1-27 (2000).

Kumari et al. "Controlled Release of Metformin hydrochloride through crosslinked blends of chitosan-starch" *Advances in Applied Science Research* 2(2):48-54 (2011).

Lee et al. "Polyelectrolyte Complexes of Sodium Alginate with Chitosan or Its Derivatives for Microcapsules" *Journal of Applied Polymer Science* 63:425-432 (1997).

Lim et al. "Application of a fiber-reactive chitosan derivative to cotton fabric as an antimicrobial textile finish" *Carbohydrate Polymers* 56(2):227-234 (2004).

Lim et al. "Synthesis and antimicrobial activity of a water-soluble chitosan derivative with a fiber-reactive group" *Carbohydrate Research* 339(2):313-319 (2004).

Lindblad et al. "New Hemicellulose-Based Hydrogels" *ACS Symposium Series* 864(22):347-359 (2004).

Liu et al. "Antibacterial Action of Chitosan and Carboxymethylated Chitosan" *Journal of Applied Polymer Science* 79:1324-1335 (2001).

Liu et al. "Structural characterization and antimicrobial activity of chitosan/betaine derivative complex" *Carbohydrate Polymers* 55:291-297 (2004).

Liu et al. "Thermal processing of starch-based polymers" *Progress in Polymer Science* 34:1348-1368 (2009).

Okazaki et al. "Development of Poly(vinyl alcohol) Hydrogel for Waste Water Cleaning. II. Treatment of N,N-Dimethylformamide in Waste Water with Poly(vinyl alcohol) Gel with Immobilized Microorganisms" *Journal of Applied Polymer Science* 58:2243-2249 (1995).

Pelissari et al. "Extrusion parameters related to starch/chitosan active films properties" *International Journal of Food Science & Technology* 46:702-710 (2011).

Petzold et al. "Carboxymethyl xylan—synthesis and detailed structure characterization" *Carbohydrate Polymers* 64(2):292-298 (2006).

Rayford et al. "Crosslinked Cationic and Anionic Starches: Preparation and Use in Heavy Metal Removal" *Starch* 31:361-365 (1979).

Rozie et al. "Crosslinked xylan as an affinity adsorbent for endo-xylanases" *Carbohydrate Polymers* 17(1):19-28 (1992).

Shi et al. "Characterization of citric acid/glycerol co-plasticized thermoplastic starch prepared by melt blending" *Carbohydrate Polymers* 64(4):748-755 (2007).

Steckel et al. "Production of chitosan pellets by extrusion/spheronization" *European Journal of Pharmaceutics and Biopharmaceutics* 57:107-114 (2004).

Sun et al. "Preparation of sugarcane bagasse hemicellulosic succinates using NBS as a catalyst" *Carbohydrate Polymers* 53(4):483-495 (2003).

Thatte, Mrunal R. "Synthesis and Antibacterial Assessment of Water-Soluble Hydrophobic Chitosan Derivatives Bearing Quaternary Ammonium Functionality" *Dissertation* 120 pages (Dec. 2004).

Umemura et al. "Preparation and Characterization of Maillard Reacted Chitosan Films with Hemicellulose Model Compounds" *Journal of Applied Polymer Science* 108:2481-2487 (2008).

Vaara et al. "Polycations as Outer Membrane-Disorganizing Agents" *Antimicrobial Agents and Chemotherapy* 24(1):114-122.

Vaca-Garcia et al. "Cellulose Esterification with Fatty Acids and Acetic Anhydride in Lithium Chloride/N,N-Dimethylacetamide Medium" *Journal of the American Oil Chemists' Society* 75:315-319 (1998).

Varma et al. "Metal complexation by chitosan and its derivaties: a review" *Carbohydrate Polymers* 55(1):77-93 (2004).

Wang et al. "Preparation, characterization and antimicrobial activity of chitosan—Zn complex" *Carbohydrate Polymers* 56:21-26 (2004).

Wing, Robert E. "Starch Citrate: Preparation and Ion Exchange Properties" *Starch* 48:275-279 (1996).

Yin et al. "Miscibility studies of the blends of chitosan with some cellulose ethers" *Carbohydrate Polymers* 63(2):238-244 (2006).

Yu et al. "Polymer blends and composites from renewable resources" *Progress in Polymer Science* 31:576-602 (2006).

Zdanowicz et al. "Starch graft copolymers as superabsorbents obtained via reactive extrusion processing" *Polish Journal of Chemical Technology* 12(2):14-17 (2010).

Zhang et al. "Chitosan-acrylamide graft copolymers and flocculation properties" *Xi'an Jiaotong Daxue Xuebao* 36(5):541-544 (2002).

Zhang et al. "Synthesis and characterization of water-soluble O-succinyl-chitosan" *European Polymer Journal* 39(8):1629-1634 (2003).

Zheng et al. "Study on antimicrobial activity of chitosan with different molecular weights" *Carbohydrate Polymers* 54:527-530 (2003).

Goldstein et al. "Improve Well Performance by Reducing Formation Damage" Unconventional Resources Technology Conference (pp. 2752-2769) (Jul. 20-22, 2015).

Goldstein et al. "Self-Suspending Proppant Transport Technology Increases Stimulated Reservoir Volumn and Reduces Proppant Pack and Formation Damage" SPE Annual Technical Conference and Exhibition (16 pages) (Sep. 2015).

Kuo et al. "Effects of reaction conditions on the physicochemical properties of cationic starch studied by RSM" Carbohydrate Polymers, 75(4):627-635 (2009).

Liang et al. "A comprehensive review on proppant technologies" Petroleum, 2:26-39 (2016).

Liu et al. "A method to evaluate hydraulic fracture using proppant detection" Applied Radiation and Isotopes, 105:139-143 (2015).

Lorenz et al. "Starch Hydrolysis Under High Temperatures and Pressures" Cereal Chemistry, 49:616-628 (1972).

"USGS Water-Quality Information: Water Hardness and Alkalinity" https://water.usgs.gov/owq/hardness-alkalinity.html (3 pages) (2016).

Narkrugsa et al. "Production of starch derivatives by cooking extrusion" Starch/Stärke, 44:81-90 (1992) (English translation of abstract).

\* cited by examiner

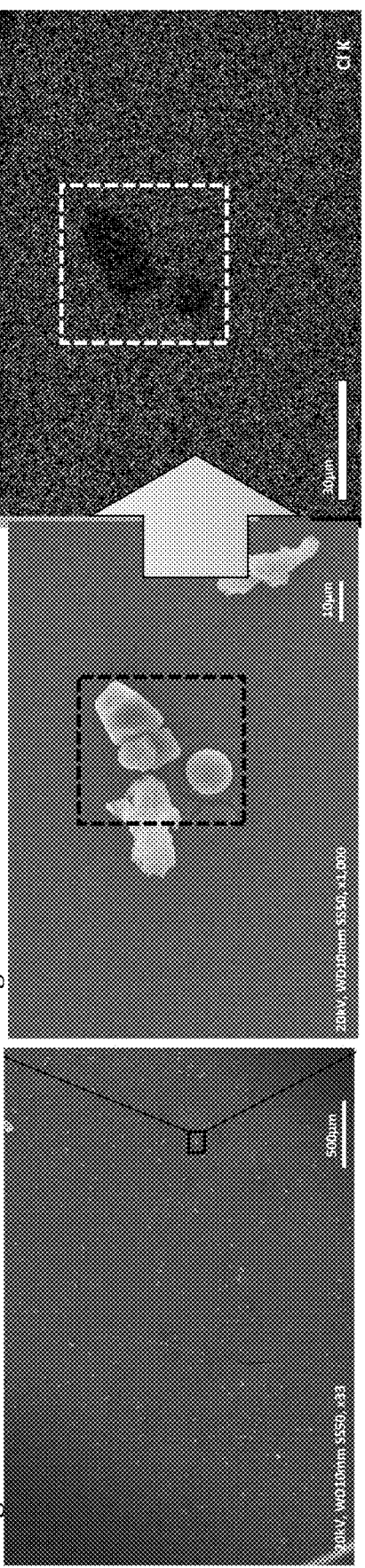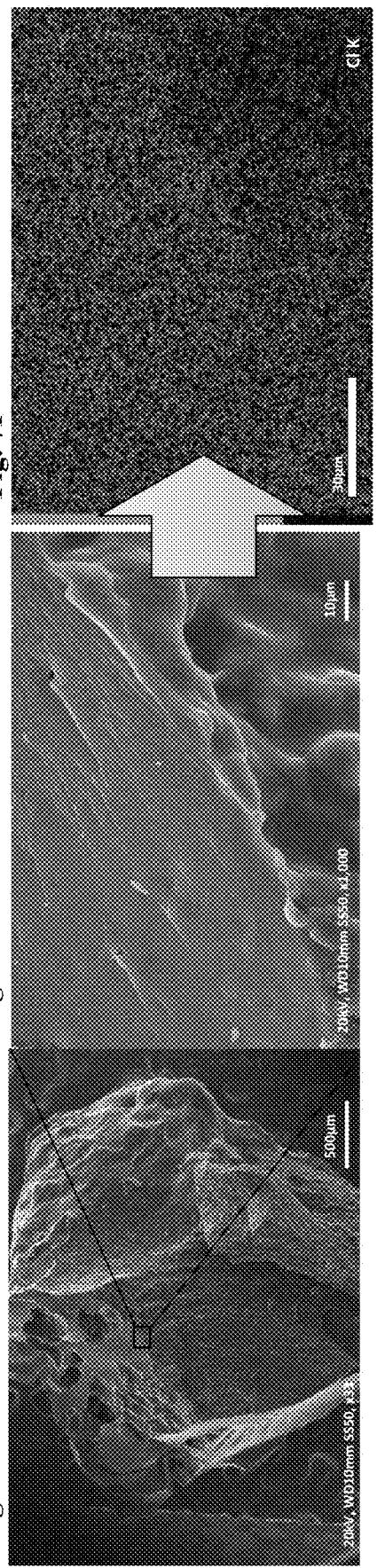
Fig. 7A Fig. 7B Fig. 7C Fig. 7D Fig. 7E Fig. 7F

MODIFIED BIOPOLYMERS AND METHODS OF PRODUCING AND USING THE SAME

RELATED APPLICATION DATA

This application claims the benefit of U.S. Provisional Patent Application Ser. No. 62/006,317, filed Jun. 2, 2014, the disclosure of which is incorporated herein by reference in its entirety.

FIELD

The present invention relates to modified biopolymers, including charge-modified biopolymers, cross-linked biopolymers, and cross-linked, charge-modified biopolymers. Methods of producing and using a modified biopolymer of the present invention are also provided.

BACKGROUND

Biopolymers are of interest due to their many uses. For example, biopolymers may be useful as absorbents, such as in diapers, hygiene products, and wound dressings, and may be useful as adsorbents. In addition, biopolymers may have the advantage of providing environmentally friendly products.

However, methods of forming and/or processing biopolymers into useful products, such as traditional heterogeneous wet chemistry methods, can often be complex, expensive, and inefficient.

The present invention addresses previous shortcomings in the art by providing modified biopolymers and methods of producing and using the same.

SUMMARY

A first aspect of the present invention includes a method for producing a cross-linked, charge-modified biopolymer comprising: combining a biopolymer and at least one charge-modifying agent to form a homogenous reaction blend; reacting the biopolymer and the at least one charge-modifying agent in the homogenous reaction blend; and cross-linking the biopolymer in the homogeneous reaction blend to form a cross-linked, charge-modified biopolymer.

The method may include reacting the biopolymer and the at least one charge-modifying agent to form a charge-modified biopolymer. In some embodiments, the charge-modified biopolymer may be cross-linked with a different biopolymer, which may optionally be charged-modified.

The method may include forming a homogenous reaction blend in an extruder, optionally using a reactive extrusion process.

Another aspect of the present invention includes a method for producing a cross-linked, charge-modified starch-chitosan comprising: combining starch, chitosan, at least one charge-modifying agent, a catalyst, and a plasticizer to form a homogenous reaction blend; charge-modifying the starch and chitosan to form a charge-modified starch and a charge-modified chitosan; and cross-linking the charge-modified starch and charge-modified chitosan to form a cross-linked, charge-modified starch-chitosan.

In a further aspect of the present invention, a method for producing a cross-linked, charge-modified starch-chitosan comprises: combining starch, a first charge-modifying agent, and a catalyst to form a homogeneous reaction blend comprising a charge-modified starch; adding charge-modified chitosan and a plasticizer to the homogeneous reaction blend comprising the charge-modified starch; and cross-linking the charge-modified starch and charge-modified chitosan to form a cross-linked, charge-modified starch-chitosan.

Another aspect of the present invention includes a method for producing a cross-linked, charge-modified starch-chitosan comprising: combining starch, a first charge-modifying agent, and a catalyst, to form a charge-modified starch; forming a homogeneous reaction blend comprising the charged-modified starch, a charged-modified chitosan, and a plasticizer; and cross-linking the charge-modified starch and charged-modified chitosan to form a cross-linked, charge-modified starch-chitosan.

A further aspect of the present invention includes a cross-linked, charge-modified biopolymer prepared according to a method of the present invention.

Another aspect of the present invention includes a cross-linked, charge-modified biopolymer having a charge density of at least 3 meq/g as determined by titration.

A further aspect of the present invention includes a cross-linked, charge-modified biopolymer having an increased charge density and/or degree of cross-linking compared to a cross-linked, charge-modified biopolymer prepared using a conventional method.

An additional aspect of the present invention includes a cross-linked, charge-modified biopolymer having an increased porosity and/or pore size compared to a cross-linked, charge-modified biopolymer prepared using a conventional method.

A further aspect of the present invention includes a method of absorbing a fluid comprising contacting a cross-linked, charge-modified biopolymer of the present invention with the fluid, thereby absorbing the fluid.

Another aspect of the present invention includes a cross-linked, charge-modified biopolymer having an increased salt uptake and/or metal chelation property compared to a cross-linked, charge-modified biopolymer prepared using a conventional method.

Another aspect of the present invention includes a method of reducing the amount of a salt and/or metal in a solution comprising contacting the cross-linked, charge-modified biopolymer of the present invention with a solution comprising a salt and/or metal, wherein the salt and/or metal binds to the cross-linked, charge-modified biopolymer, thereby reducing the amount of the salt and/or metal in the solution.

The foregoing and other aspects of the present invention will now be described in more detail with respect to other embodiments described herein. It should be appreciated that the invention can be embodied in different forms and should not be construed as limited to the embodiments set forth herein. Rather, these embodiments are provided so that this disclosure will be thorough and complete, and will fully convey the scope of the invention to those skilled in the art.

BRIEF DESCRIPTION OF THE DRAWINGS

FIG. 7A shows a SEM image of a commercially available cationic starch at 33×.

FIG. 7B shows a SEM image of the commercially available cationic starch at 1000×.

FIG. 7C shows a SEM image of an EDS chlorine map of the commercially available cationic starch.

FIG. 7D shows a SEM image of a cationic starch prepared according to methods of the present invention at 33×.

FIG. 7E shows a SEM image of the cationic starch prepared according to methods of the present invention at 1000×.

FIG. 7F shows a SEM image of an EDS chlorine map of the cationic starch prepared according to methods of the present invention.

DETAILED DESCRIPTION

Figure 1A:
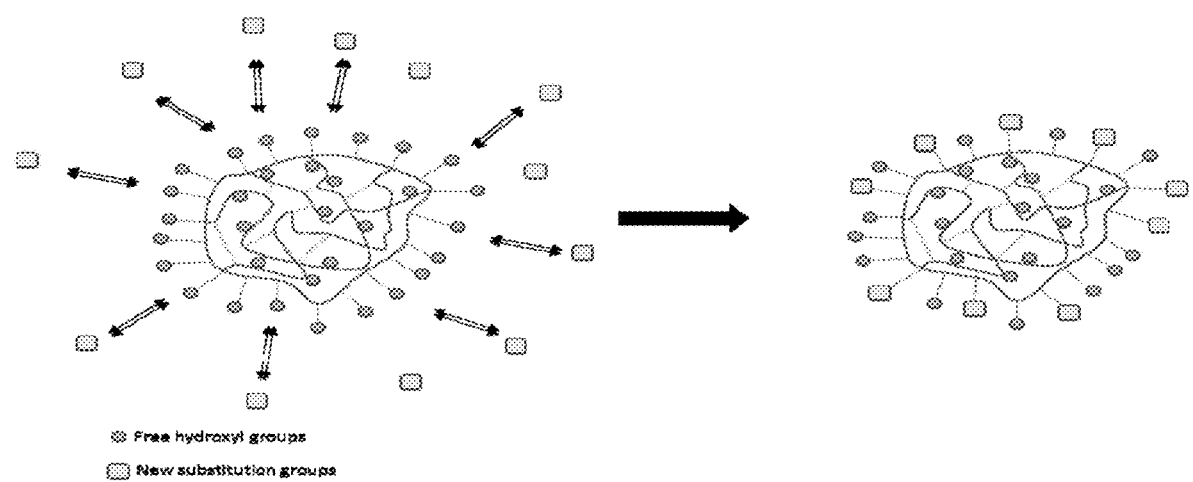
FIG. 1A is a schematic of a heterogeneous phase reaction.

The present invention will now be described more fully hereinafter. This invention may, however, be embodied in different forms and should not be construed as limited to the embodiments set forth herein. Rather, these embodiments are provided so that this disclosure will be thorough and complete, and will fully convey the scope of the invention to those skilled in the art.

The terminology used in the description of the invention herein is for the purpose of describing particular embodiments only and is not intended to be limiting of the invention. As used in the description of the invention and the appended claims, the singular forms "a", "an" and "the" are intended to include the plural forms as well, unless the context clearly indicates otherwise.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the present application and relevant art and should not be interpreted in an idealized or overly formal sense unless expressly so defined herein. The terminology used in the description of the invention herein is for the purpose of describing particular embodiments only and is not intended to be limiting of the invention. All publications, patent applications, patents and other references mentioned herein are incorporated by reference in their entirety. In case of a conflict in terminology, the present specification is controlling.

Also as used herein, "and/or" refers to and encompasses any and all possible combinations of one or more of the associated listed items, as well as the lack of combinations when interpreted in the alternative ("or").

Unless the context indicates otherwise, it is specifically intended that the various features of the invention described herein can be used in any combination. Moreover, the present invention also contemplates that in some embodiments of the invention, any feature or combination of features set forth herein can be excluded or omitted. To illustrate, if the specification states that a complex comprises components A, B and C, it is specifically intended that any of A, B or C, or a combination thereof, can be omitted and disclaimed.

As used herein, the transitional phrase "consisting essentially of" (and grammatical variants) is to be interpreted as encompassing the recited materials or steps "and those that do not materially affect the basic and novel characteristic(s)" of the claimed invention. See, In re Herz, 537 F.2d 549, 551-52, 190 U.S.P.Q. 461, 463 (CCPA 1976) (emphasis in the original); see also MPEP § 2111.03. Thus, the term "consisting essentially of" as used herein should not be interpreted as equivalent to "comprising."

The term "about," as used herein when referring to a measurable value, such as, for example, an amount or concentration and the like, is meant to refer to variations of up to ±20% of the specified value, such as, but not limited to, ±20%, ±15%, ±10%, ±5%, ±1%, ±0.5%, or even ±0.1% of the specified value, as well as the specified value. For example, "about X" where X is the measurable value, is meant to include X as well as variations of ±20%, ±15%, ±10%, ±5%, ±1%, ±0.5%, or even ±0.1% of X. A range provided herein for a measurable value may include any other range and/or individual value therein.

According to some embodiments of the present invention, provided herein are modified biopolymers, such as, charge-modified biopolymers, cross-linked biopolymers, and/or cross-linked, charge-modified biopolymers. The cross-linked, charged-modified biopolymers of the present invention may comprise one biopolymer that has been charge-modified and cross-linked. In some embodiments, the cross-linked, charged-modified biopolymers of the present invention may comprise two or more different biopolymers that are cross-linked and at least one of the biopolymers has been charge-modified. The two or more different biopolymers may be cross-linked with each other. In certain embodiments, a cross-linked, charge-modified biopolymer may comprise two different biopolymers that are cross-linked and both of the biopolymers may be charge-modified.

A "biopolymer" as used herein refers to a polymer that has at least one free amine and/or hydroxyl group present on a majority of the monomeric units of the polymer and is a polymer produced by a living organism or a derivative thereof. In some embodiments, a free amine and/or hydroxyl group may be present on each of the monomeric units of the polymer backbone. Exemplary biopolymers include, but are not limited to, proteins and/or polysaccharides. As one of ordinary skill in the art will understand, a biopolymer may be synthetically obtained (e.g., through laboratory synthesis) and/or obtained and/or derived from nature (e.g., from a living or previously living organism). Therefore, the biopolymer may be the same as a polymer found in nature (i.e., a native biopolymer) or may be a derivative thereof. For example, a biopolymer of the present invention may be a derivative of a polymer produced by a living organism, the derivative caused by the synthetic method used to obtain or isolate the biopolymer from nature. In some embodiments, a biopolymer may be a polymer produced by bacteria and/or microbes.

Further exemplary biopolymers include, but are not limited to, starches (including amylose and/or amylopectin), chitosans, hemicelluloses, lignins, celluloses, chitins, alginates, dextrans, pullanes, polyhydroxyalkanoates, fibrins, cyclodextrins, proteins (e.g., soy protein), polysaccharides (e.g., pectin), and/or polylactic acids.

A biopolymer used in a method of the present invention may have a moisture content of about 20% by weight or less. In some embodiments, the biopolymer may have a moisture content of about 20%, 15%, 10%, 5%, or less by weight. In certain embodiments, the biopolymer may have a moisture content in a range of about 5% to about 20% by weight or about 10% to about 15% by weight. In some embodiments, a method of the present invention utilizes a biopolymer, such as, for example, starch, having a moisture content of about 20% by weight or less, and the biopolymer may be in powder form.

A biopolymer used in a method of the present invention may have a molecular weight of about 10,000 Daltons or more. In some embodiments, the biopolymer may have a molecular weight of about 10,000; 20,000; 30,000; 40,000, 50,000; 60,000; 70,000; 80,000; 90,000; 100,000; 200,000; 300,000; 400,000; 500,000; 600,000; 700,000; 800,000; 900,000; 1,000,000; 2,000,000; 3,000,000, 4,000,000 Daltons or more. In certain embodiments, the biopolymer may have a molecular weight of about 50,000 Daltons or more. In some embodiments, the biopolymer may have a molecular weight of about 100,000 Daltons to about 4,000,000 Daltons, about 500,000 Daltons to about 3,000,000 Daltons, or about 1,000,000 Daltons to about 2,000,000 Daltons. In some embodiments, when only one biopolymer is used to prepare a modified biopolymer of the present invention (e.g., a cross-linked, charge-modified biopolymer), the biopolymer may have a molecular weight of greater than about 50,000 Daltons. In some embodiments, when two or more different biopolymers are used to prepare a modified biopolymer of the present invention (e.g., a cross-linked, charge-modified biopolymer), at least one of the two or more different biopolymers may have a molecular weight of about 10,000 Daltons or more, such as, for example, about 20,000; 30,000; 40,000, 50,000 Daltons or more. In certain embodiments, a modified biopolymer of the present invention (e.g., a cross-linked, charge-modified biopolymer) may be prepared using a biopolymer having a molecular weight of greater than about 50,000 Daltons optionally with a second different biopolymer having a molecular weight of greater than about 10,000 Daltons. In some embodiments, the biopolymer may be polydisperse.

In some embodiments, the biopolymer used in a method of the present invention may be a starch. Exemplary starches include, but are not limited to, potato starch, wheat starch, tapioca starch, cassava starch, rice starch, corn starch, waxy corn starch, waxy wheat starch, waxy rice starch, waxy sorghum starch, waxy cassava starch, waxy barley starch, and/or waxy potato starch. The starch may have an amylopectin content of about 70% w/w or more and an amylose content of about 30% w/w or less. In certain embodiments, the starch may have an amylopectin content of about 70%, 75%, 80%, 85%, 90%, 95% w/w or more and an amylose content of about 30%, 25%, 20%, 15%, 10%, 5% w/w or less. In some embodiments, the starch may have an amylopectin content of less than 90%, such as, for example, about 85%, 80%, 75%, 70%, 65%, 60%, 55%, 50%, 45%, 40%, 35%, 30%, 25%, 20%, 15%, 10%, etc. In some embodiments, starch may have an amylopectin content in a range of about 10% to about 85%, such as, for example, about 25% to about 85% or about 50% to about 80%.

In some embodiments, the starch may be dissolvable in water (e.g., pre-gelatinized starch). In certain embodiments, the starch may be steam exploded to form a pre-gelatinized starch. In some embodiments, a starch used in a method of the present invention may have a reduced degree of crystallinity compared to a native starch. In certain embodiments, the biopolymer used in a method of the present invention may be a chitosan. The chitosan may have a degree of deacetylation of about 50% to about 100%. In some embodiments, the chitosan may have a degree of deacetylation of about 50%, 55%, 60%, 65%, 70%, 75%, 80%, 85%, 90%, 95%, or 100%. In certain embodiments, the chitosan may have a degree of deacetylation in a range of about 70% to about 100% or greater than about 80%. In some embodiments, the chitosan may have a molecular weight of greater than about 80,000 Daltons.

A biopolymer used in a method of the present invention may be charge-modified according to a method described herein (e.g., by reacting the biopolymer with a charge-modifying agent in a homogeneous reaction blend). However, as one of skill in the art will recognize, a biopolymer may naturally carry a charge (i.e., the biopolymer may natively be charged in that the charge is present on the biopolymer not through a method of the present invention). Thus, a method of the present invention may change the charge present on a biopolymer (e.g., type and/or amount of charge). In some embodiments, a charge-modified biopolymer may be soluble (e.g., partially or fully soluble) in a polar solvent, such as, for example, water and/or a polar organic solvent at room temperature and/or a nonpolar solvent at room temperature. In some embodiments, a charge-modified biopolymer of the present invention may be at least 70% soluble in a polar and/or nonpolar solvent at room temperature. Solubility may be used as an indication and/or characteristic of the degree of charge modification.

"Charge-modifying agent" as used herein refers to a molecule or compound comprising one moiety that may react with an amine and/or hydroxyl group of the biopolymer and a second moiety that may be positively charged or negatively charged under suitable conditions, such as, for example, at a certain pH. "Moiety" as used herein, refers to a portion of a molecule or compound having a particular functional or structural feature. For example, a moiety may comprise a functional group or a reactive portion of a compound. As those of skill in the art recognize, a strong acidic moiety (e.g., —$SO_3H$) or a weak acidic moiety (e.g., —COOH) may form a negatively charged moiety and a strong basic moiety (e.g., —$NH_3OH$) or a weak basic moiety (—$NH_2$) may form a positively charged moiety.

The charge-modifying agent may comprise at least one moiety that may be a positively charged group, such as, but not limited to, a primary amine, secondary amine, tertiary amine, quaternary ammonium, sulfonium, and/or phosphonium group. Exemplary charge-modifying agents that can have a positively charged moiety include, but are not limited to, ethylene imine, N-(2-hydroxyethyl) ethylene imine, cyanamide, beta-morpholinoethyl chloride, beta-diethyl aminoethylchloride, S-diethyl amino 1,2-epoxypropane dimethyl aminoethyl methacrylate, epoxy 3-methyl ammonium, glycidyltrimethylammonium chloride (e.g., QUAB® 151), N-(2,3-epoxypropyl) trimethyl ammonium chloride, (4-chlorobutene-2) trimethyl ammonium chloride, 2-chloroethyl methyl ethyl sulfonium iodide, and/or Z-chloroethyl tributylphosphonium chloride. In some embodiments, the charge-modifying agent comprises a tertiary amino alkyl group, a hydroxyalkyl group, a quaternary ammonium alkyl group, or a hydroxyalkyl group.

In some embodiments, a positively charged moiety may be introduced into and/or onto a biopolymer by reacting the biopolymer and charge-modifying agent in a homogeneous reaction blend, optionally in the presence of a catalyst. This reaction may be a dry melt process and/or may be an etherification or esterification reaction.

The charge-modifying agent may comprise at least one moiety that may be a negatively charged group, such as, but not limited to, a carboxyl, sulfonate, sulfate, and/or a phosphate group (e.g., sodium tripolyphosphate). Exemplary charge-modifying agents that can have a negatively charged moiety include, but are not limited to, acids (e.g., citric acid, glacial acetic acid, ethylenediaminetetraacetic acid (EDTA), and/or diethylene triamine pentaacetic acid (DTPA)); monohalogen substituted fatty acids (e.g., monochloroacetic acid); acetates (e.g., sodium monochloroacetate); anhydrides (e.g., succinic anhydride, maleic anhydride, citraconic anhydride, and/or octenyl succinicanhydride); alkyl esters of acrylic acid, crotonic acid or itaconic acid (e.g., methyl and ethyl esters of acrylic acid, crotonic acid or itaconic acid); acrylonitrile; sodium periodate; sulfones; and/or sulfonic acids (e.g., halo alkane sulfonic acids, chlorooxypropane sulfonic acid, epoxypropane sulfonic acid, chlorooxypropane sulfonic acid, epoxypropane sulfonic acid, ethene sulfonic acid, and/or salts thereof).

In some embodiments, a negatively charged moiety may be introduced into a biopolymer by reacting the biopolymer and charge-modifying agent in a homogeneous reaction blend in the presence an alkaline catalyst. In certain embodiments, the charge-modifying agent may be acrylonitrile and the reaction of the biopolymer and acrylonitrile in the presence of an alkaline catalyst may be followed by hydrolysis of the cyanoethyl groups. When the charge-modifying agent is sodium periodate, the reaction with the biopolymer may be followed by a treatment to transform the carbonyl groups into carboxyl groups, such as, but not limited to, by treating with sodium chlorite, and/or by a treatment with sodium bisulfite and/or potassium bisulfite. In certain embodiments, both carboxyl and sulfonate groups may be introduced into a biopolymer by reacting the biopolymer with an anhydride of an unsaturated acid (e.g., maleic acid) and a bisulfite. The bisulfite may be reacted with the unsaturated bond of the polysaccharide half ester.

In some embodiments, the charge-modifying agent may react with an amine and/or hydroxyl group of a biopolymer to provide a charge-modified biopolymer. The charge-modified biopolymer may be cationic (i.e., have a net positive charge) or may be anionic (i.e., have a net negative charge). In some embodiments, the charge-modified biopolymer may contain both positively and negatively charged moieties.

A biopolymer used in a method of the present invention may be cross-linked by reacting a cross-linking agent with the biopolymer and optionally with at least one different biopolymer that may optionally be charge-modified. In some embodiments, a cross-linking agent may be reacted with at least one charge-modified biopolymer. "Cross-linking agent" as used herein refers to a compound that links two or more biopolymer chains and/or portions of the biopolymer together, the biopolymer optionally being charge-modified. The linkage may be achieved via a covalent bond or an ionic bond. In some embodiments, the linkage may be through a moiety or group of the biopolymer or different biopolymers.

Exemplary cross-linking agents include, but are not limited to, epichlorohydrin, glutaraldehyde, oxalic acid, malonic acid, succinic acid, glutaric acid, adipic acid, pimelic acid, fumaric acid, maleic acid, malic acid, tartartic acid, sodium trimetaphosphate, sodium tripolyphosphate, ionic cross-linkers (e.g., calcium chloride, calcium hydroxide, etc.), poly(ethylene glycol) diglycidyl ether (PEGDE), poly(propylene glycol) diglycidyl ether (PPGDE), and/or an anhydride, such as, for example, succinic anhydride and maleic anhydride. In some embodiments, the cross-linking agent is non-toxic.

Without wishing to be bound to any particular theory, in some embodiments, a charge-modifying agent, such as, for example, citric acid, when heated inside an extruder may dehydrate to yield an anhydride. The free hydroxyl groups from a biopolymer, such as, for example, starch, present in the reaction mixture may react with the anhydride to form starch citrate. Further, without wishing to be bound to any particular theory, in some embodiments, additional dehydration of the biopolymer and/or charge-modified biopolymer may allow for cross-linking of the biopolymer and/or charge-modified biopolymer to occur. In some embodiments, cross-linking of the biopolymer and/or charge-modified biopolymer may be achieved due to the heat inside the extruder and/or during a post treatment process, such as, for example, a thermal post-treatment process. In some embodiments, a charge-modified biopolymer may be prepared using a ring-opening polymerization of anhydrous acids.

A modified biopolymer of the present invention (e.g., a cross-linked, charge-modified biopolymer) may comprise a plurality of pores or void spaces formed therein. The pores or void spaces may have an average diameter of about 0.1 micron to about 500 microns, such as, but not limited to, about 10 microns to about 500 microns, about 50 microns to about 500 microns, about 100 microns to about 400 microns, or about 250 microns to about 500 microns. In certain embodiments, the pores or void spaces may have an average diameter of about 0.1 micron, 1 micron, 10 microns, 25 microns, 50 microns, 100 microns, 150 microns, 200 microns, 250 microns, 300 microns, 350 microns, 400 microns, 450 microns, or 500 microns.

In some embodiments, a modified biopolymer of the present invention (e.g., a cross-linked, charge-modified biopolymer) has a net positive charge (i.e., is cationic) or a net negative charge (i.e., is anionic). In certain embodiments, the modified biopolymer (e.g., a cross-linked, charge-modified biopolymer) is a polyampholyte. In some embodiments, the modified biopolymer may be a polyelectrolyte, which may be hydrophilic (e.g., due to the number of ionizable groups present on the modified biopolymer). In some embodiments, a modified biopolymer of the present invention (e.g., a cross-linked, charge-modified biopolymer) may be a superabsorbent. In some embodiments, a superabsorbent of the present invention, may absorb a fluid in an amount of about 15 times or more (e.g., 20×, 30×, 40×, 50×, 100×, etc.) relative to its weight. A superabsorbent, in some embodiments, may absorb a 0.9% saline solution in an amount of about 20 times or more (e.g., 25×, 30×, etc.) at room temperature and/or water in an amount of about 35 times or more (e.g., 40×, 45×, etc.) at room temperature. In some embodiments, a cross-linked, charge-modified biopolymer of the present invention is charge-modified and cross-linked in an extruder. Some embodiments of the present invention may provide a cross-linked, charge-modified biopolymer in a one step extrusion process.

A modified biopolymer of the present invention (e.g., a cross-linked, charge-modified biopolymer) may be a biosorbent and/or may be biodegradable. A "biosorbent" as used herein may refer to an absorbent (e.g., that may be utilized in the removal of a fluid) and/or an adsorbent (e.g., that may be utilized as an ion exchange material and/or metal chelating material). In some embodiments, a biosorbent may be a superabsorbent.

A modified biopolymer of the present invention (e.g., a cross-linked, charge-modified biopolymer and/or charge-modified biopolymer) may have a charge density of about 3 meq/g or more as determined by titration. For example, in some embodiments, charge density may be determined by titration as described in Example 1.1. In some embodiments, the modified biopolymer may have a charge density of about 3, 3.5, 4, 4.5, 5, 5.5, 6, 6.5, 7, 7.5, 8, 8.5, 9, 9.5, 10 meq/g or more as determined by titration. In certain embodiments, the modified biopolymer may have a charge density of at least about 5 meq/g as determined by titration.

In some embodiments, a method of the present invention may provide a modified biopolymer (e.g., a cross-linked, charge-modified biopolymer and/or charge-modified biopolymer) having the charge modification substantially uniformly distributed throughout the bulk of the modified biopolymer. Thus, the modified biopolymer may have a substantially uniform charge density. In some embodiments, the uniformity of the charge density of a modified biopolymer may be determined by evaluating the presence of insoluble materials after exposure of the modified biopolymer to a solvent, such as, for example water. Observation of particles (such as, for example, 1-10 μm particles) may indicate the lack of charge modification within the particles and/or modified biopolymer. In some embodiments, charge density distribution on a modified biopolymer may be determined and/or evaluated using one or more spectrographic analytical techniques such as, but not limited to, EDS, EPS, and/or TOF-SIMS of the charged moiety's counter ion. In some embodiments, an uneven distribution of counter ions and/or the presence of particles (e.g., 1-10 μm particles) lacking the counter ion indicates non-uniformity and/or inhomogeneity in regard to the distribution of the charge on the modified biopolymer.

In some embodiments, the modified biopolymer may have an increased charge density and/or degree of cross-linking compared to a modified biopolymer (e.g., a cross-linked, charge-modified biopolymer) prepared using a conventional method. "Conventional method" as used herein in reference to a method for preparing a modified biopolymer refers to a method for preparing a modified biopolymer in which the biopolymer is a solid (e.g., a particulate) and a reaction of the biopolymer with at least one reactant in the method occurs at a solid interface of the biopolymer. In some embodiments, a conventional method may be a method that does not involve forming a homogeneous reaction blend and/or that does not involve a melt extrusion process, such as a reactive extrusion process. In some embodiments, a conventional method may be a semi-dry process, a multi-phase process, a process having a liquid interface with a solid material, and/or a heterogeneous process. In certain embodiments, a conventional method may be a heterogeneous wet chemistry method and/or a multi-phase process.

The modified biopolymer may have a charge density and/or degree of cross-linking that is increased by at least about 5% or more compared to a modified biopolymer prepared using a conventional method. In some embodiments, the modified biopolymer may have a charge density and/or degree of cross-linking that is increased by at least about 5%, 10%, 15%, 20%, 25%, 30%, 35%, 40%, 45%, 50%, 55%, 60%, 65%, 70%, 75%, 80%, 85%, 90%, 95%, 100%, 150%, 200%, or more compared to a modified biopolymer prepared using a conventional method.

In some embodiments, the degree or amount of cross-linking present in a modified biopolymer of the present invention (e.g., a cross-linked, charge-modified biopolymer and/or cross-linked biopolymer) may provide mechanical rigidity to the modified biopolymer and/or correlate with the degree of mechanical rigidity in the modified biopolymer.

In some embodiments, a modified biopolymer of the present invention (e.g., a cross-linked, charge-modified biopolymer) may have a degree of substitution of about 0.01 or more, such as, for example, in a range of about 0.01 to about 0.3. For example, in some embodiments, the modified biopolymer may have a degree of substitution of about 0.01, 0.02, 0.03, 0.04, 0.05, 0.06, 0.07, 0.08, 0.09, 0.1, 0.15, 0.2, 0.25, 0.3, or more. In some embodiments, a modified biopolymer may have a degree of substitution in a range of about 0.09 to about 0.3 or about 0.1 to about 0.25. In some embodiments, the degree of substitution may be measured by nitrogen content.

In some embodiments, a modified biopolymer of the present invention (e.g., a cross-linked, charge-modified biopolymer) may have a free swell capacity (FSC) of about 5 g/g or more, such as, for example, in a range of about 5 g/g to about 100 g/g. For example, in some embodiments, the modified biopolymer may have a FSC of about 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, or more.

In some embodiments, a modified biopolymer of the present invention (e.g., a cross-linked, charge-modified biopolymer) may have a Centrifuge Retention Capacity (CRC) of about 1 g/g or more, such as, for example, in a range of about 1 g/g to about 60 g/g. For example, in some embodiments, the modified biopolymer may have a CRC of about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, or more.

A modified biopolymer of the present invention (e.g., a cross-linked, charge-modified biopolymer) may comprise a plurality of pores and/or void spaces. The modified biopolymer may have an increased porosity and/or pore size compared to a modified biopolymer prepared using a conventional method. The porosity may be increased by increasing the number of pores or void spaces. The pores or void spaces may be substantially the same size (e.g., varying in size or diameter by less than about 20%) or may be different sizes. The modified biopolymer may have a porosity and/or pore size that is increased by at least about 5% or more compared to a modified biopolymer prepared using a conventional method. In some embodiments, the modified biopolymer may have a porosity and/or pore size that is increased by at least about 5%, 10%, 15%, 20%, 25%, 30%, 35%, 40%, 45%, 50%, 55%, 60%, 65%, 70%, 75%, 80%, 85%, 90%, 95%, 100%, 150%, 200%, or more compared to a modified biopolymer prepared using a conventional method.

In some embodiments, the modified biopolymer may have a more uniform porosity and/or pore size compared to a modified biopolymer prepared using a conventional method. A more uniform porosity may include a more uniformly or evenly dispersed number of pores or void spaces throughout the modified biopolymer. In some embodiments, a more uniform pore size may include a more uniform diameter of the pores or void spaces throughout the modified biopolymer. In certain embodiments, the porosity and/or pore size of the modified biopolymer may be more uniform compared to the porosity and/or pore size of a modified biopolymer prepared using a conventional method, and may vary by less than about 20%, such as, for example, by about 20%, 15%, 10%, 5% or less, as determined by comparing two or more defined areas of the modified biopolymer compared to two or more defined areas of the modified biopolymer prepared using a conventional method.

A modified biopolymer of the present invention (e.g., a cross-linked, charge-modified biopolymer) may sequester, bind, absorb, chelate, uptake, adsorb, and/or the like a fluid (e.g., water, hydrocarbons, oils, alcohols, aqueous solutions, non-aqueous solutions, ionic solutions such as salt solutions, biological fluids such as blood and/or urine, gases, waste water, and/or fracking fluids), a charged species (e.g., ions such as potassium ions ($K^+$), calcium ions ($Ca^{2+}$), sodium ions ($Na^+$), chloride ions ($Cl^-$), fluoride ions (F), phosphite ions ($PO_3^{3-}$), sulfate ions ($SO_4^{2-}$), sulfite ions ($SO_3^{2-}$), phosphate ions ($PO_4^{3-}$), polyatomic ions, and/or metal ions; charged peptides, polypeptides, nucleic acids, and/or oligonucleotides; and the like), and/or a metal (e.g., lead, mercury, cadmium, arsenic, copper, chromium, thallium, selenium, zinc, calcium, magnesium, silver, boron, and the like). In some embodiments, a modified biopolymer of the present invention (e.g., a cross-linked, charge-modified biopolymer) may physically adsorb a species present in a fluid, such as, but not limited to an ionic species and/or a metal. The species may be dissolved in the fluid. In certain embodiments, a modified biopolymer may bind, such as, for example, via hydrogen bonding, covalent bonding, van der waals/adsorptive binding, and/or ionic bonding, a fluid, charged species, and/or metal.

In certain embodiments, a modified biopolymer of the present invention (e.g., a cross-linked, charge-modified biopolymer) may sequester, bind, absorb, chelate, uptake, adsorb, and/or the like an ion and/or a metal. The metal may be in an ionized form, such as in the form of a salt. As those skilled in the art recognize, a metal may exist in a number of ionized forms, such as, monovalent, divalent, polyvalent, anionic, and/or cationic forms. Further exemplary ions and/or metals, in any ionized form, that a modified biopolymer of the present invention may sequester, bind, absorb, chelate, uptake, adsorb, and/or the like include, but are not limited to, sodium, potassium, lithium, ammonium, barium, strontium, manganese, silver, cesium, zinc, cadmium, selenium, calcium, magnesium, iron, radium, mercury, copper, lead, nickel, chromium, arsenic, gold, uranium, chloride, bromide, nitrate, iodide, carbonate, sulphate, and/or phosphate.

In some embodiments, a modified biopolymer of the present invention (e.g., a cross-linked, charge-modified biopolymer) may sequester, bind, absorb, chelate, uptake, adsorb, and/or the like an organic. Exemplary organics include, but are not limited to, toluene, xylenes, benzene, ethylbenzene, trimethylbenzene, acetone, and/or methanol.

A modified biopolymer of the present invention (e.g., a cross-linked, charge-modified biopolymer) may sequester, bind, absorb, chelate, uptake, adsorb, and/or the like an increased amount or concentration of a fluid, a charged species, and/or a metal compared to a modified biopolymer prepared using a conventional method. The modified biopolymer may sequester, bind, absorb, chelate, uptake, adsorb, and/or the like an increased amount or concentration of a fluid, charged species, and/or a metal by at least about 5% or more compared to a modified biopolymer prepared using a conventional method. In some embodiments, the modified biopolymer may sequester, bind, absorb, chelate, uptake, adsorb, and/or the like an increased amount or concentration of a fluid, charged species, and/or a metal by at least about 5%, 10%, 15%, 20%, 25%, 30%, 35%, 40%, 45%, 50%, 55%, 60%, 65%, 70%, 75%, 80%, 85%, 90%, 95%, 100%, 150%, 200%, or more compared to a modified biopolymer prepared using a conventional method.

In some embodiments, a modified biopolymer of the present invention may comprise starch and chitosan. The starch and chitosan may both be charged-modified and cross-linked with each other to form a cross-linked, charged-modified starch-chitosan biopolymer.

According to some embodiments of the present invention, a method for producing a charge-modified biopolymer may be provided. The method may comprise reacting a biopolymer and at least one charge-modifying agent in a homogeneous reaction blend to form a charge-modified biopolymer. In some embodiments, the method may comprise combining the biopolymer and at least one charge-modifying agent, optionally with a plasticizer and/or catalyst, to form a homogenous reaction blend. In some embodiments, the method may comprise reacting two or more different biopolymers with a charge-modifying agent in a homogeneous reaction blend. Optionally, at least one of the two or more different biopolymers may be charge-modified (e.g., according to a method of the present invention) prior to the reacting step.

According to some embodiments of the present invention, a method for producing a cross-linked biopolymer may be provided. The method may comprise reacting a biopolymer and at least one cross-linking agent in a homogeneous reaction blend to form a cross-linked biopolymer. In some embodiments, the method may comprise combining the biopolymer and at least one cross-linking agent, optionally with a plasticizer and/or catalyst, to form a homogenous reaction blend. In some embodiments, the method may comprise reacting two or more different biopolymers with a cross-linking agent in a homogeneous reaction blend.

According to some embodiments of the present invention, a method for producing a cross-linked, charge-modified biopolymer may be provided. The method may comprise reacting a biopolymer and at least one charge-modifying agent in a homogenous reaction blend to form a charge-modified biopolymer and cross-linking the charge-modified biopolymer in the homogeneous reaction blend to form a cross-linked, charge-modified biopolymer. Some embodiments may include reacting two or more different biopolymers with the at least one charge-modifying agent in the homogeneous reaction blend to form at least one charge-modified biopolymer. In some embodiments, the charge-modified biopolymer may be cross-linked to one or more different biopolymers in the homogeneous reaction blend, and the one or more different biopolymers may optionally be charge-modified, such as, for example, prior to a combining, reacting, and/or cross-linking step. In some embodiments, a charge-modified biopolymer prepared according to a method of the present invention is used to prepare a cross-linked, charge-modified biopolymer of the present invention. In some embodiments, the biopolymer and the at least one charge-modifying agent may be combined to form a homogeneous reaction blend.

In some embodiments, one or more steps of a method of the present invention (e.g., a combining, reacting, and/or cross-linking step) may occur simultaneously and/or sequentially with another step in the method. For example, in some embodiments, a reacting step to form a charged-modified biopolymer of the present invention may occur simultaneously with a cross-linking step to form a cross-linked, charge-modified biopolymer of the present invention. A further example includes, in some embodiments, that a cross-linking step to form a cross-linked, charge-modified biopolymer of the present invention may occur after a reacting step to form a charged-modified biopolymer has occurred. In some embodiments, a reacting and cross-linking step occur in different reaction zones of an extruder.

In some embodiments, a method for producing a cross-linked, charge-modified biopolymer may comprise combining a first charge-modified biopolymer and a second charge-modified biopolymer that is different than the first charge-modified biopolymer, optionally with a plasticizer, cross-linking agent, and/or catalyst, to form a homogeneous reaction blend, and cross-linking the first and second charge-modified biopolymers in the homogeneous reaction blend to form a cross-linked, charge-modified biopolymer. The first and/or second charge-modified biopolymers may be charge-modified according to a method of the present invention.

Some embodiments include a method for producing a cross-linked, charge-modified biopolymer comprising: combining a first biopolymer, a second biopolymer that is different than the first biopolymer, at least one charge-modifying agent, a plasticizer, and optionally a catalyst to form a homogenous reaction blend; reacting the first biopolymer and second biopolymer with the at least one charge-modifying agent to form a charge-modified first biopolymer and a charge-modified second biopolymer; and cross-linking the charge-modified first biopolymer and charge-modified second biopolymer to form a cross-linked, charge-modified biopolymer.

In some embodiments, a method for producing a cross-linked, charge-modified biopolymer comprises: combining a first biopolymer, a first charge-modifying agent, and optionally a catalyst to form a homogeneous reaction blend comprising a charge-modified first biopolymer; adding a charge-modified second biopolymer and a plasticizer to the homogeneous reaction blend comprising the charge-modified first biopolymer; and cross-linking the charge-modified first biopolymer and charge-modified second biopolymer to form a cross-linked, charge-modified biopolymer. In some embodiments, the charge-modified second biopolymer is prepared according to a method of the present invention.

Some embodiments include a method for producing a cross-linked, charge-modified biopolymer comprising: combining a first biopolymer, a first charge-modifying agent, and optionally a catalyst to form a charge-modified first biopolymer; forming a homogeneous reaction blend comprising the charged-modified first biopolymer, a charged-modified second biopolymer, and a plasticizer; and cross-linking the charge-modified first biopolymer and charged-modified second biopolymer to form a cross-linked, charge-modified biopolymer. In some embodiments, the charge-modified second biopolymer is prepared according to a method of the present invention.

In some embodiments, a method for producing a cross-linked, charge-modified biopolymer comprises: forming a homogenous reaction blend comprising a first biopolymer, a second biopolymer that is optionally charged-modified, and at least one charge-modifying agent; reacting the first biopolymer and the at least one charge-modifying agent in the homogenous reaction blend to form a charge-modified biopolymer; and cross-linking the charge-modified biopolymer and the second biopolymer in the homogeneous reaction blend to form a cross-linked, charge-modified biopolymer. In some embodiments, the second biopolymer may be charge-modified according to a method of the present invention.

In some embodiments, a method for producing a cross-linked, charge-modified biopolymer comprises: forming a first homogenous reaction blend comprising a first biopolymer and at least one charge-modifying agent; reacting the first biopolymer and the at least one charge-modifying agent in the first homogenous reaction blend to form a charge-modified biopolymer; combining the charge-modified biopolymer with a second biopolymer that is optionally charge-modified to form a second homogeneous reaction blend; and cross-linking the charge-modified biopolymer and second biopolymer in the second homogeneous reaction blend to form a cross-linked, charge-modified biopolymer. In some embodiments, the second biopolymer may be charge-modified according to a method of the present invention.

In some embodiments, a method for producing a modified biopolymer of the present invention (e.g., a cross-linked, charge-modified biopolymer) may occur and/or be carried out in a continuous process. In some embodiments, the reacting and/or cross-linking steps may occur and/or be carried out in a continuous process. A continuous process is one that does not involve intermediate steps that stop a reaction in process. Exemplary intermediate steps include, but are not limited to, changing a buffer or providing a wash step before obtaining the product. The continuous process may be carried out or performed in an extruder optionally using a reactive extrusion process. For example, a continuous process includes a process in which all reactants are added to an extruder either at the same time or different times and the process occurs continuously (i.e. without stopping for intermediate steps) until the modified biopolymer is extruded. A continuous process may also include a step in a method of the present invention that is carried out or performed in an extruder, such as a reacting and/or cross-linking step.

In some embodiments, a method of the present invention may comprise a continuous process followed by a non-continuous process, such as, but not limited to, a post-treatment step. In certain embodiments, a method of the present invention may comprise a continuous process, a non-continuous process (e.g., a batch process), and optionally a subsequent continuous process. In some embodiments, a method of the present invention may comprise a continuous process to prepare a charge-modified biopolymer (e.g., a charge-modified starch), and then the charge-modified biopolymer may undergo a post-treatment, which may optionally be a batch process. The method may further comprise another continuous process in which the charged-modified biopolymer may be reacted with another biopolymer (e.g., chitosan), which may optionally be charge-modified.

A "reactive extrusion process" as used herein refers to a process in which a biopolymer is both chemically and physically modified. A reactive extrusion process may provide for a chemical modification of a biopolymer, such as, but not limited to, grafting onto the biopolymer, cross-linking of the biopolymer, functionalization of the biopolymer, and/or charge-modification of the biopolymer. In some embodiments, a reactive extrusion process may provide for polymerization and/or branching of a biopolymer. The polymerization and/or branching may be with a different biopolymer to provide a co-polymer. An exemplary physical modification may be changing the form of the biopolymer, such as, but not limited to, from a powder, particulate, and/or solid form to a molten or melted form.

At least one charge-modifying agent may be present in a homogeneous reaction blend in an amount of about 5% to about 200% or more by weight of a biopolymer present in the homogeneous reaction blend. In some embodiments, at least one charge-modifying agent may be present in a homogeneous reaction blend in an amount of about 5%, 10%, 20%, 30%, 40%, 50%, 60%, 70%, 80%, 90%, 100%, 110%, 120%, 130%, 140%, 150%, 160%, 170%, 180%, 190%, 200%, or more by weight of a biopolymer present in the homogeneous reaction blend. In some embodiments, at least one charge-modifying agent may be present in a homogeneous reaction blend in an amount of at least about 75% by weight of a biopolymer present in the homogeneous reaction blend. In some embodiments, a method of the present invention may include at least one charge-modifying agent present in a homogeneous reaction blend in an amount of at least about 75% by weight of the biopolymer and provide a modified biopolymer having a charge density of at least 1.5 meq/g of the modified biopolymer.

A homogeneous reaction blend is a melted blend of all the components in a single phase. In some embodiments, a homogeneous reaction blend may be obtained using an extruder. In certain embodiments, a homogeneous reaction blend may be obtained using a reactive extrusion process in an extruder. The homogeneous reaction blend may be in the form of a single liquid phase. A homogeneous reaction blend may provide a uniform distribution of the components or reactants as compared to a conventional method. In some embodiments, a method of the present invention may provide a chemical reaction that occurs more uniformly and/or completely due to the formation of a homogeneous reaction blend as compared to a conventional method. In some embodiments, the biopolymer in the homogeneous reaction blend may be a melted thermoplastic. A biopolymer may react thermo-mechanically and/or chemically with one or more reagents to form a charge-modified biopolymer of the present invention, which may be thermoplastic and/or a viscoelastic material. In some embodiments, a method of the present invention removes hydrogen bonding and/or crystalline domains present in a biopolymer. This may allow for all or substantially all portions of the biopolymer to be available for chemical reaction, such as, for example, charge-modification and/or cross-linking.

Figure 1B:
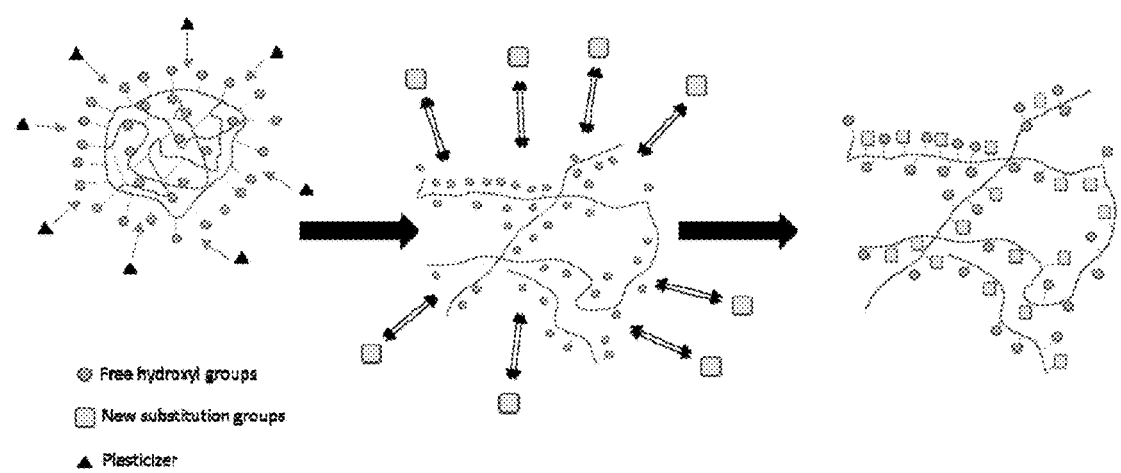
FIG. 1B is a schematic of a homogeneous phase reaction.

In some embodiments, a homogeneous reaction blend may contain a plasticized biopolymer, which may allow for greater access to moieties throughout the biopolymer. In contrast, in a heterogeneous phase reaction (for example, in which modified biopolymers are synthesized by a coating process, in a diluted suspension, or with a concentrated gel solution) there is a limited amount of moieties (e.g., free hydroxyls) exposed to the reagent as the surface moieties are exposed to the reagent, but not the interior moieties are not exposed. The reaction is thus carried out on the surface of the solid granule as shown in FIG. 1A, such as, for example, by direct conversion of either the semi-crystalline granules in aqueous suspension or as a dry process. FIG. 1B shows an exemplary schematic of a homogeneous phase reaction in which a biopolymer in the presence of a plasticizer is a plasticized to obtain thermoplastic behavior. Under the action of thermo-mechanical energy, the starch granule will melt. The plasticizer may be adsorbed to the starch by heating the mixture and destruction of the granule structure of the biopolymer may occur with the introduction of mechanical and heat energy. In the presence of a plasticizer, biopolymer granules may be transferred to a continuous phase and moieties (e.g., hydroxyl free groups) may be available to react with the reagent. In some embodiments, a homogeneous reaction blend may aid in distributing a modification (e.g. a charge-modification) along a biopolymer chain and/or more uniformly throughout a biopolymer in contrast to a conventional method, such as, for example, one in which the modification is only achieved at the surface (e.g. at the surface of a solid biopolymer granule).

In some embodiments, a method of the present invention may provide a modified biopolymer (e.g., a charge-modified biopolymer and/or a cross-linked, charge-modified biopolymer) that lacks a granular structure and/or morphology. In some embodiments, a method of the present invention may destroy or remove the crystalline structure and/or domains of a biopolymer and/or modified biopolymer.

In certain embodiments, a method of the present invention may provide a reaction with faster kinetics than the kinetics of the same reaction in a conventional method. The speed of at least one reaction in a method of the present invention may be increased compared to the speed of the same reaction in a conventional method. In some embodiments, a method of the present invention provides an overall greater speed of reaction to produce a modified biopolymer of the present invention compared to a conventional method. In some embodiments, a plasticizer may be present in the homogeneous reaction blend with a biopolymer and a charge-modifying agent. In some embodiments, a plasticizer may be combined with the biopolymer and the at least one charge-modifying agent to form a homogenous reaction blend. A plasticizer may be present in a homogeneous reaction blend in an amount of about 10% to about 400% or more by weight of a biopolymer present in the homogeneous reaction blend. In some embodiments, a plasticizer may be present in a homogeneous reaction blend in an amount of about 10%, 20%, 30%, 40%, 50%, 60%, 70%, 80%, 90%, 100%, 110%, 120%, 130%, 140%, 150%, 160%, 170%, 180%, 190%, 200%, 210%, 220%, 230%, 240%, 250%, 260%, 270%, 280%, 290%, 300%, 310%, 320%, 330%, 340%, 350%, 360%, 370%, 380%, 390%, 400%, or more by weight of a biopolymer present in the homogeneous reaction blend. In some embodiments, a plasticizer may be present in a homogeneous reaction blend in an amount of at least about 30% or more by weight of a biopolymer (e.g., starch) present in the homogeneous reaction blend. In some embodiments, a plasticizer may be present in a homogeneous reaction blend in an amount of at least about 100% or more by weight of a biopolymer (e.g., chitosan, hemicellulose, pectin, and/or soy protein) present in the homogeneous reaction blend.

In some embodiments, where a reactive plasticizer is used (i.e., a plasticizer that serves as both a plasticizer and a reagent), such as, for example, citric acid, the plasticizer may be present in an amount of about 100%, 125%, 150%, 175%, 200% or more by weight of a biopolymer (e.g., starch) present in the homogeneous reaction blend. In some embodiments, a reactive plasticizer may be present in an amount of about 70% to about 175% by weight of a biopolymer (e.g., starch) present in the homogeneous reaction blend, such as, for example, about 75% to about 100% or about 90% to about 150%. In some embodiments, where a non-reactive plasticizer is used (i.e., a plasticizer that only functions to allow the material to extrude and does not serve as a reagent), such as, for example, water and, at some pHs, glycerol, the plasticizer may be present in amount of about 100% or less, such as, for example, less than 75%, 50%, or 25%. In some embodiments, a non-reactive plasticizer may be present in an amount of about 20% to about 200% by weight of a biopolymer present in the homogeneous reaction blend, such as, for example, about 20% to about 50%, about 75% to about 100%, or about 90% to about 150%.

The plasticizer may reduce the glass transition temperature ($T_g$). In some embodiments, the plasticizer may improve the flexibility, workability, distensibility, and/or processability of a biopolymer and may do so by lowering the glass transition temperature ($T_g$). In certain embodiments, a biopolymer to be extruded by a method of the present invention may not be thermoplastic. Thus, to extrude a biopolymer that is not thermoplastic, the glass transition temperature ($T_g$) must be lowered by addition of a plasticizer.

A plasticizer may reduce the tension of deformation, hardness, density, viscosity and/or electrostatic charge of a biopolymer and at the same time may increase the biopolymer chain flexibility, resistance to fracture and/or dielectric constant. Other properties of the biopolymer may also be affected by the inclusion of a plasticizer, such as, but not limited to, the degree of crystallinity, optical clarity, electric conductivity, fire behavior and/or resistance to biological degradation. In some embodiments, a plasticizer may disrupt hydrogen bonds present in a crystalline structure of the biopolymer and this may lead to the breaking of the crystalline domains that prevent thermal processing.

In some embodiments, the plasticizer may allow for the biopolymer to melt and/or become thermoplastic to provide a single phase. In some embodiments, a plasticizer may lower the $T_g$ by solvating the inherent crystallinity of the biopolymer and disrupting hydrogen bonding. This may allow for the melt processability of biopolymers that are not traditionally melt processable.

A plasticizer may be a low molecular weight non-volatile compound. Additional exemplary plasticizers include, but are not limited to, citric acid, triphenyl phosphate, camphor oil, amylacetate, allyurea, citrate esters, phthalic acid esters, dioctyl phthalate, fatty acid esters, benzoates, tartrates, chlorinated hydrocarbons, esters of adipic acid, polyols (e.g., glycerol, ethylene glycol (EG), diethylene glycol (DEG), triethylene glycol (TEG), tetraethylene glycol, polyethylene glycol, propylene glycol (PG), sorbitol, mannitol, xylitol, fatty acids, and/or vegetable oils), lecithin, waxes, amino acids, surfactants, and/or water.

In some embodiments, citric acid is present in a homogeneous reaction blend and it may function as both a charge-modifying agent and a plasticizer.

A catalyst may optionally be present in a homogeneous reaction blend. In some embodiments, a catalyst and/or a plasticizer may be combined with a biopolymer and at least one charge-modifying agent to form a homogenous reaction blend. A catalyst may be present in a homogeneous reaction blend in an amount of about 1% to about 100% or more by weight of a biopolymer present in the homogeneous reaction blend. In some embodiments, a catalyst may be present in a homogeneous reaction blend in an amount of about 1%, 5%, 10%, 20%, 30%, 40%, 50%, 60%, 70%, 80%, 90%, 100%, or more by weight of a biopolymer present in the homogeneous reaction blend.

A catalyst may accelerate the charge-modification and/or cross-linking reaction. In some embodiments, a catalyst may adjust the pH to enhance the opening of chemical bonds. Exemplary catalysts include, but are not limited to, sodium hypophosphite, sodium bisulfate, sodium bisulfite, and/or caustics (e.g., sodium hydroxide, calcium hydroxide, etc.). In some embodiments, a method of the present invention may be carried out at a pH of about 2, 3, 4, 5, 6, 7, 8, 9, 10, 11, or 12. In some embodiments, a method of the present invention may be carried out at a pH in a range of about 9 to about 12, about 10 to about 12, about 2 to about 7, or about 2 to about 5.

In some embodiments, the catalyst may be an initiator. In some embodiments, the cross-linking step may comprise reacting the biopolymer with at least one cross-linking agent, optionally in the presence of an initiator. The biopolymer may be a charge-modified biopolymer. Exemplary initiators include, but are not limited to, peroxides such as acyl peroxides (e.g., benzoyl peroxide) and dialkyl or aralkyl peroxides (e.g., di-t-butyl peroxide, dicumyl peroxide, cumyl butyl peroxide, 1,1-di-t-butylperoxy-3,5,5-trimethylcyclohexane, 2,5-dimethyl-2,5-di-t-butylperoxy hexane, and bis(t-butylperoxyisopropyl)benzene); ketone peroxides (e.g., cyclohexanone peroxide and methylethylketone peroxide); sodium methoxide, potassium persulfate, ceric ammonium, sodium hydroxide, and/or azo compounds (e.g., azobisisobutyronitrile).

An initiator may be present in a homogeneous reaction blend in an amount of about 1% to about 100% or more by weight of a biopolymer present in the homogeneous reaction blend. In some embodiments, an initiator may be present in a homogeneous reaction blend in an amount of about 1%, 5%, 10%, 20%, 30%, 40%, 50%, 60%, 70%, 80%, 90%, 100%, or more by weight of a biopolymer present in the homogeneous reaction blend.

Optional additives may be used in a method of preparing a modified biopolymer. Exemplary optional additives include, but are not limited to, dyes, pigments, organic fillers, inorganic fillers, softening agents (e.g., mineral oils and synthetic oils), flame retardants, crystallization accelerators, stabilizers (e.g., heat and light stabilizers), tie-agents, nucleating agents, other polymers (e.g., non-biopolymers), and/or the like.

Forming a homogenous reaction blend may comprise melt blending at least one biopolymer and at least one charge-modifying agent, optionally with at least one plasticizer, a catalyst (e.g., an initiator), and/or optional additives. In some embodiments, at least one biopolymer, at least one charge-modifying agent, at least one plasticizer, and optionally a catalyst may be combined to form a homogeneous reaction blend. In some embodiments, a homogeneous reaction blend may be formed and/or prepared using a reactive extrusion process. The reactive extrusion process may be carried out in an extruder.

In certain embodiments, a homogeneous reaction blend may be formed comprising at least two different biopolymers. In some embodiments, a homogeneous reaction blend may be formed comprising a charge-modified biopolymer and at least one different biopolymer, which may optionally be charge-modified. When two biopolymers are present in a homogeneous reaction blend, a first biopolymer may be present in the homogeneous reaction blend in an amount of about 10% to about 200% or more by weight of a second biopolymer present in the homogeneous reaction blend. In some embodiments, a first biopolymer may be present in a homogeneous reaction blend in an amount of about 10%, 20%, 30%, 40%, 50%, 60%, 70%, 80%, 90%, 100%, 110%, 120%, 130%, 140%, 150%, 160%, 170%, 180%, 190%, 200%, or more by weight of a second biopolymer present in the homogeneous reaction blend.

In some embodiments, a first biopolymer and a second biopolymer may be present in a homogeneous reaction blend in a ratio in a range of 0.1:1 to 4:1 (first biopolymer:second biopolymer), such as, for example, in a ratio in a range of 0.5:1 to 2:1 or 1:1 to 3:1. In certain embodiments, a first biopolymer and a second biopolymer may be present in a homogeneous reaction blend in a ratio of about 0.5:1, 1:1, or 1:0.5.

In some embodiments, the reacting and/or cross-linking step(s) may be carried out and/or performed in a homogeneous reaction blend. The reacting and/or cross-linking step(s) may be carried out and/or performed using a reactive extrusion process. In some embodiments, the reacting and/or cross-linking step(s) may be carried out at a temperature in a range of about 80° C. to about 200° C., such as, for example, at a temperature in a range of about 80° C. to about 120° C., about 80° C. to about 150° C., about 90° C. to about 120° C., about 100° C. to about 120° C., about 100° C. to about 200° C., about 150° C. to about 180° C., or about 110° C. to about 130° C. In certain embodiments, the reacting and/or cross-linking step(s) may be carried out at a temperature of about 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, or 150° C. In some embodiments, the reacting and/or cross-linking step(s) may be carried out at a temperature of about 140° C. or less.

In some embodiments, the reacting and/or cross-linking step(s) may be carried out at a temperature that avoids degradation of a biopolymer and/or modified biopolymer. In some embodiments, increasing the temperature of the reacting and/or cross-linking steps may provide for an increased amount of charge-modification on the biopolymer if the temperature remains below the degradation temperature for the biopolymer. In some embodiments, the reacting step may be carried out and/or performed at a temperature in a range of about 100° C. to about 175° C., such as, for example, about 120° C. to about 140° C. or about 100° C. to 150° C. In some embodiments, the cross-linking steps may be carried out and/or performed at a temperature in a range of about 120° C. or more, such as, for example, about 120° C. to about 175° C. or about 120° C. to about 140° C.

One or more process conditions for a method of the present invention may be modified to provide a particular modified biopolymer, such as, for example, a super absorbent, ion exchange resin, etc., and/or a particular property of a modified biopolymer, such as, for example, the degree of charge modification, cross-linking, etc. Example processing conditions for a method of the present invention include, but are not limited to, the type of extruder (e.g., single screw vs. twin screw); screw diameter (D); screw length (L) (L/D may be used to describe an extruder configuration); screw configuration (i.e., specific types of shear inducing sections within an extruder which may range from gentle conveying elements to more shear intensive elements that may be designed to enhance uniform mixing within the extruder and/or accelerate a chemical reaction); temperature (overall and profile along various extruder zones); screw RPM; number of separate extruder zones where both temperature can be changed independent of other zones and different ingredients of the formulation can be added; and feed rate of different formulation elements into different zones. In some embodiments, the combination of one or more independently controlled process variables may influence dependent variables of residence time, mechanical energy input (SME) and/or shear. Changes in screw RPM may induce changes in shear, heating and/or residence time in the extruder.

In some embodiments, the reacting and/or cross-linking step(s) may be carried out in an extruder. The reacting and/or cross-linking step(s) may carried out in an extruder with a residence time in a range of about 0.1 minutes to about 30 minutes, such as, for example, in a range of about 0.1 minutes to about 10 minutes, about 0.5 minutes to about 5 minutes, about 1 minute to about 10 minutes, about 1 minute to about 5 minutes, or about 1 minute to about 3 minutes. In certain embodiments, the reacting and/or cross-linking step(s) may be carried out in an extruder with a residence time of about 0.1, 0.2, 0.3, 0.4, 0.5, 0.6, 0.7, 0.8, 0.9, 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 minutes. In some embodiments, the reacting and/or cross-linking step(s) may be carried out in an extruder with a residence time of about 5 minutes. In some embodiments, increasing the residence time of the reacting and/or cross-linking steps may provide for an increased amount of charge-modification on the biopolymer.

The reacting and/or cross-linking step(s) may carried out in an extruder having a screw RPM in a range of about 10 to about 500 rpm, such as, but not limited to, about 10 to about 200, about 50 to about 200, about 100 to about 200, about 125 to 250, about 100 to about 500, or about 90 to about 130. In certain embodiments, the reacting and/or cross-linking step(s) may be carried out in an extruder having a screw RPM in a range of about 40, 50, 60, 70, 80, 90, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, or 500 rpm. In some embodiments, the reacting and/or cross-linking step(s) may be carried out in an extruder having a screw RPM of about 120 rpm.

In some embodiments, the reacting and/or cross-linking step(s) may be carried out in an extruder with a Specific Mechanical Energy (SME) value of at least about 20 kJ/kg. In certain embodiments, the reacting and/or cross-linking step(s) may be carried out in an extruder with a SME value in a range of about 20 kJ/kg to about 500 kJ/kg or about 25 kJ/kg to about 250 kJ/kg. The SME value may be measured using methods known to those of skill in the art.

The step of reacting a biopolymer with a charge-modifying agent and the step of cross-linking the biopolymer may occur simultaneously. Alternatively or in addition, in some embodiments, the step of reacting the biopolymer with the charge-modifying agent and the step of cross-linking the biopolymer may be done sequentially. Thus, in some embodiments, the step of reacting the biopolymer with the charge-modifying agent may be carried out first to form a charge-modified biopolymer and then cross-linking step may be carried out with the charge-modified biopolymer.

Figure 6:
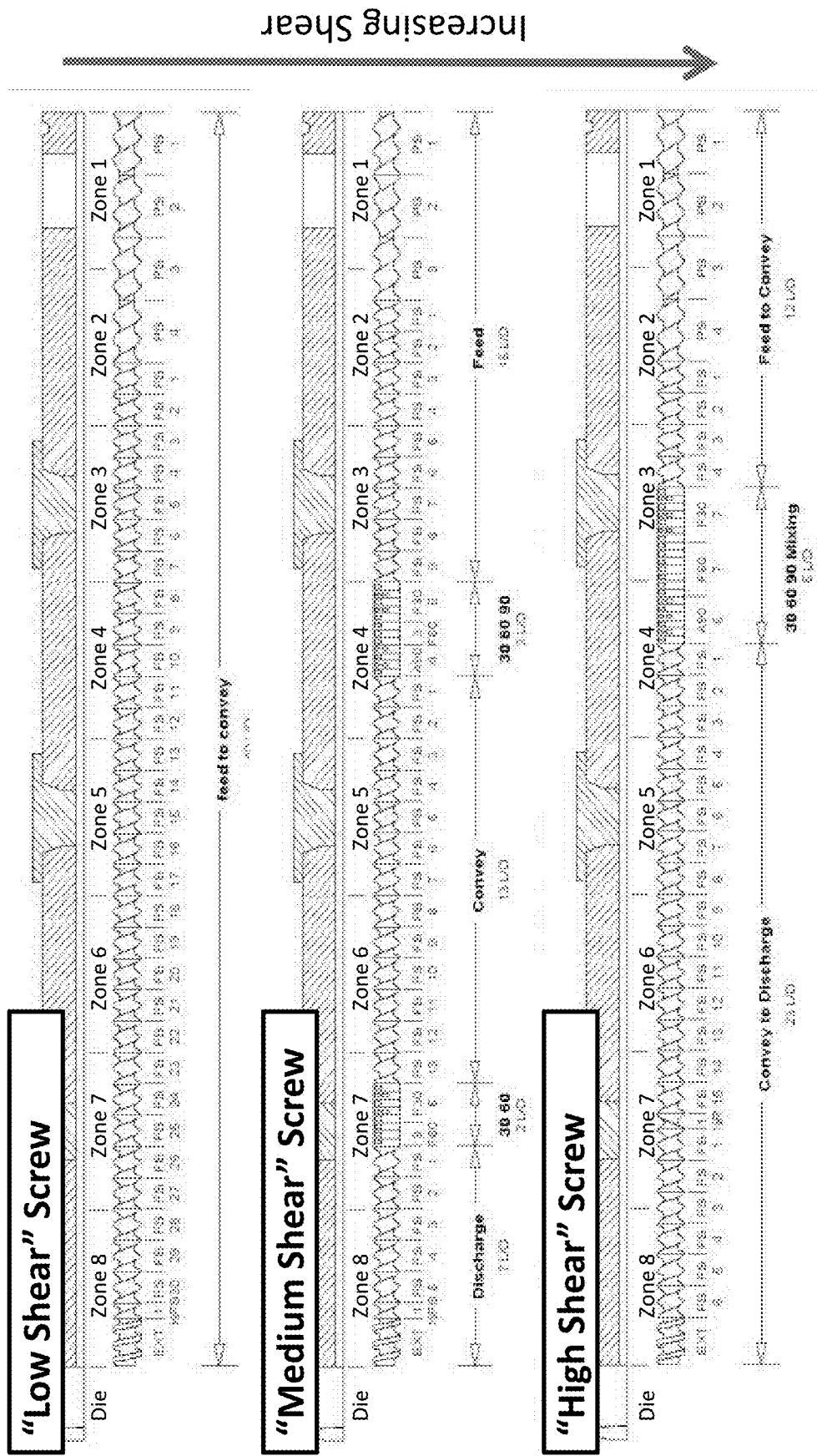
FIG. 6 illustrates exemplary screw configurations according to embodiments of the present invention.

Exemplary devices for carrying out a method of the present invention include, but are not limited to, co-rotational and counter rotational twin screws, thermal kinetic compounders, high shear mixers, paddle mixers, static mixers blenders, open-type mixing roll, closed Banbury mixer, kneader, single-screw extruder, vented screw extruder, and/or twin-screw extruder (e.g., a parallel or conical twin-screw extruder). In some embodiments, an extruder is used to carry out a method of the present invention. Exemplary screw configurations include those illustrated in FIG. 6. A low shear screw configuration may include a low number or no shear inducing elements or zones along the screw profile where shear inducing elements or zones may include mixing, kneading, and/or reversing elements or zones which increase the torque or load on the extrusion motor for a given mass flow rate. A medium and/or high shear screw configuration may include an increased number of shear inducing elements or zones compared to a low shear screw configuration.

In some embodiments, the components or reactants for one or more steps in a method of the present invention may be dry mixed together prior addition to an extruder. Alternately or in addition, two or more feeders (e.g., loss-in-weight feeders) may be used that supply the components or reactants to be blended to an extruder. In certain embodiments, multiple extruders may be used to feed melts of the blend components, such as in co-extrusion. In some embodiments, one or more components or reactants may be added to an extruder in powder form. The components and/or mixture blends may be sized by conventional means such as pelletization, granulation, and/or grinding.

A method of the present invention may be performed and/or carried out as a single-stage direct extrusion process or a multi-stage extrusion process. In some embodiments, the method comprises in-line compounding. In some embodiments, the method is carried out in an extruder comprising at least two reaction zones and the at least two reaction zones are used for one or more steps in the method for preparing a modified biopolymer of the present invention (e.g., a cross-linked, charge-modified biopolymer). For example, a method of the present invention may comprise reacting a biopolymer and at least one charge-modifying agent at a first reaction zone to form a charge-modified biopolymer and cross-linking the charge-modified biopolymer at a second reaction zone to form a cross-linked, charge-modified biopolymer.

In some embodiments, one or more reagents may be in powder form when added to an extruder and may not be in the form of a liquid or paste. In some embodiments, the one or more reagents in powder form may have a moisture content of about 20% by weight or less. Some embodiments include adding a biopolymer and/or charged-biopolymer to an extruder in powder form and/or adding one or more additional reagents (e.g., a charge-modifier, plasticizer, cross-linker, etc.) to the extruder in powder form. The one or more additional reagents may be added in the same or a different reaction zone than the biopolymer and/or charged-biopolymer.

In some embodiments, an extruder is used as one complete reaction vessel, which may allow for the reaction to occur along the entire length of the extruder. When two or more reaction zones are provided, the one or more process conditions (e.g., temperature, shear, etc.) in one or more reaction zones may be independently provided and/or changed. Some embodiments may include providing a different temperature and/or screw element in at least one reaction zone compared to another reaction zone. For example, in some embodiments, a mixture of a biopolymer (e.g., starch), plasticizer, charge-modifying agent, and catalyst may be introduced into a feed zone in an extruder and in the extruder the mixture may form a homogenous reaction blend. The reaction taking place in the extruder may be modified (e.g., accelerated and/or slowed) by varying the temperature in one or more reaction zones in the extruder. In some embodiments, the reaction may be accelerated by increasing the temperature in one or more reaction zones in the extruder. Some embodiments may include introducing shear in one more reaction zones, such as, e.g., zone 3 and/or zone 5 of an extruder, by having intense mixing elements in the screw to facilitate mixing and/or shear induced reaction. In some embodiments, the length of different reaction zones and/or the length of the extruder itself (e.g., by moving the injection zone closer to the end of the extruder) may be varied or adjusted, such variations or adjustments may modify the degree of reaction. The length of the extruder is generally defined as the length over diameter ratio or L/D.

In some embodiments, an extruder may be used as a sequential reactor. For example, in some embodiments, a mixture of a biopolymer (e.g., starch), plasticizer, and charge-modifying agent may be introduced into a feed zone of an extruder. The mixture may be heated as it is transported through one or more reaction zones (e.g., one or more initial reaction zones, such as, e.g., zones 1 and 2) using conveying elements on the screw, and the charge-modifying agent may react with the biopolymer to form a charge-modified biopolymer. Then, a cross-linking agent may be added in either solid or liquid form into one or more reaction zones (e.g., zone 3) to form the cross-linked, charge-modified biopolymer. In some embodiments, following the reaction zone(s) in which the charge-modifying agent was added, an intense mixing screw element may be placed on the screw in one or more reaction zones (e.g., in zone 4 and/or 5) to mix the cross-linking agent with the charge-modified biopolymer. The cross-linking reaction may be facilitated by different temperatures and/or different screw elements in one or more reaction zones (e.g., zone 4 and/or 5). In some embodiments, a foaming agent (e.g., water) may be injected into an extruder (e.g., in a reaction zone near the end of the extruder, such as, e.g., at zone 6), which may cause the cross-linked, charge-modified biopolymer to expand as it exits the die. Some embodiments include that the biopolymer introduced into a feed zone of an extruder is in powder form.

In some embodiments, a method of the present invention may comprise foaming a modified biopolymer of the present invention (e.g., a cross-linked, charge-modified biopolymer). Foaming may be done to induce porosity and/or void size of the modified biopolymer, such as by opening and/or increasing cell porosity. Foaming may aid in increasing fluid, charged species, and/or metal sequestration, binding, absorption, chelation, uptake and/or the like. In some embodiments, the modified biopolymer may have open, connected pores, which may facilitate mass transfer within the modified biopolymer and access of ions in a fluid to the ionic binding sites of the modified biopolymer. Foaming the modified biopolymer may modify (e.g., increase or decrease) the viscoelastic properties of the modified biopolymer. In some embodiments, the amount or degree of modification may vary with the amount of a fluid (e.g., water, carbon dioxide, nitrogen, etc.) absorbed in the modified biopolymer at the time of foaming.

A foaming agent may be a chemical agent or physical agent. Exemplary foaming agents, include, but are not limited to, supercritical nitrogen ($N_2$) calcium carbonate ($CaCO_3$), water (e.g., steam), and/or supercritical carbon dioxide ($CO_2$).

In some embodiments, a method of the present invention may comprise treating a modified biopolymer of the present invention (i.e., a post-treatment), such as, for example, thermally treating a charge-modified biopolymer and/or cross-linked, charge-modified biopolymer post extrusion. A post-treatment of the prevent invention may increase the degree of cross-linking present in a modified biopolymer of the present invention and/or may increase and/or improve charge density and/or charge modification of a modified biopolymer. In some embodiments, a post-treatment of the present invention may decrease the soluble gel fraction in a modified biopolymer. The modified biopolymer in solid form may be undergo a post-treatment. In some embodiments, a post-treatment of the present invention may fine tune and/or modify the properties of a modified biopolymer of the present invention.

A post-treatment may comprise heating the modified biopolymer. In some embodiments, a method of the present invention may comprise heating the modified biopolymer at a temperature in a range of about 80° C. to about 180° C., such as, for example, about 100° C. to about 150° C. or about 120° C. to about 140° C., for a period of time in a range of about 0.5 minutes to about 24 hours, such as, for example, about 5 minutes to about 180 minutes, or about 30 minutes to about 90 minutes. In some embodiments, a post-treatment may comprise heating the modified biopolymer at a temperature of about 110° C. to about 130° C. for a period of time in a range of about 60 minutes to about 120 minutes. In some embodiments, a post-treatment may comprise heating the modified biopolymer at a temperature of about 130° C. to about 150° C. for a period of time in a range of about 10 minutes to about 50 minutes.

In some embodiments, a method of the present invention may comprise removing unreacted reagents, soluble and/or low molecular weight species, and/or degradation products from a modified biopolymer of the present invention, such as, for example, by rinsing, dialyzing, and/or the like the modified biopolymer. Some embodiments include removing unreacted reagants from the modified biopolymer after a post-treatment. Some embodiments of the present invention may include drying the modified biopolymer (e.g., drying at a temperature of about 40° C.). In some embodiments, a method of the present invention may comprise sizing the modified biopolymer by conventional means, such as, for example, pelletization, granulation, milling, and/or grinding.

According to some embodiments of the present invention, a method of the present invention may comprise forming a homogeneous reaction blend comprising a starch, at least one charge-modifying agent, optionally at least one plasticizer, and optionally a catalyst, and reacting the starch and the at least one charge-modifying agent to form a charged-modified starch. In some embodiments, the at least one charge-modifying agent may be an acid such as, for example, citric acid, the optional at least one plasticizer may be water and/or glycerol, and/or the optional catalyst may be sodium hypophosphite. The reacting step may comprises reacting starch and the charge-modifying agent (e.g., citric acid) in a ratio in a range of 0.1:1 to 4:1 (charge-modifying agent:starch), such as, for example, in a ratio in a range of 0.5:1 to 2:1 or 1:1 to 3:1.

The charge-modified starch may be cross-linked with another biopolymer, such as, for example chitosan to form a cross-linked, charge-modified starch-chitosan. In some embodiments, the chitosan is charged modified, such as, but not limited, protonated. In certain embodiments, the method may comprise combining charged-modified starch with chitosan, at least one plasticizer, and optionally a charge-modifying agent, and cross-linking the charged-modified starch and chitosan. In some embodiments, a charge-modifying agent may be an acid (e.g., acetic acid, such as glacial or concentrated acetic acid) and may react with the chitosan to form charge-modified chitosan that may be cross-linked with the charge-modified starch. In some embodiments, charge-modified chitosan may be prepared by reacting chitosan and acetic acid in an amount of about 1% to about 40%, such as, for example, about 2.5% to about 13% or about 20% to about 40% by weight of the chitosan, wherein acetic acid is added directly to the chitosan without the presence of water.

A method of preparing a cross-linked, charge-modified starch-chitosan may comprise providing in an extruder starch in an amount in a range of about 5 wt % to about 50 wt % and chitosan in an amount in a range of about 5 wt % to about 50 wt % to form a homogeneous reaction blend. In some embodiments, the chitosan may be charge-modified chitosan. The homogeneous reaction blend may further comprise a charge-modifying agent (e.g., citric acid) in an amount in a range of about 5 wt % to about 40 wt %, a catalyst in an amount in a range of about 0.1 wt % to about 5 wt %, and a plasticizer in an amount in a range of about 20 wt % to about 40 wt %.

According to some embodiments, a method of the present invention may comprise combining starch, chitosan, at least one charge-modifying agent, a catalyst, and a plasticizer to form a homogenous reaction blend; charge-modifying the starch and chitosan to form a charge-modified starch and a charge-modified chitosan; and cross-linking the charge-modified starch and charge-modified chitosan to form a cross-linked, charge-modified starch-chitosan. In some embodiments, the combining step may be carried out by providing, adding, feeding, injecting and/or the like all components into the extruder at substantially the same time. This may allow for the charge-modifying and cross-linking reactions to occur simultaneously.

In some embodiments, a method of the present invention may comprise combining starch, a first charge-modifying agent, and a catalyst to form a homogeneous reaction blend comprising a charge-modified starch; adding chitosan, a plasticizer, and optionally a second charge-modifying agent to the homogeneous composition comprising the charge-modified starch; and cross-linking the charge-modified starch and chitosan to form a cross-linked, charge-modified starch-chitosan. The chitosan, in some embodiments, may be charged-modified and/or added to an extruder in the presence of a charge-modifying agent, such as, for example, glacial acetic acid. In some embodiments, the method may use multiple inlets of an extruder. For example, starch, the first charge-modifying agent, and the catalyst may be added at a first inlet and/or reaction zone in an extruder, and chitosan, the plasticizer, and optionally the second charge-modifying agent may be added at a second inlet and/or reaction zone in an extruder. This may allow for the charge-modifying and cross-linking reactions to occur simultaneously and/or sequentially.

In certain embodiments, a method of the present invention may comprise combining starch, a first charge-modifying agent, and a catalyst to form a charge-modified starch; forming a homogeneous reaction blend comprising the charged-modified starch, chitosan, a plasticizer, and optionally a second charge-modifying agent; and cross-linking the charge-modified starch and chitosan to form a cross-linked, charge-modified starch-chitosan. This may allow for the charge-modifying and cross-linking reactions to occur sequentially. The chitosan, in some embodiments, may be charged-modified and/or added to an extruder in the presence of a charge-modifying agent, such as, for example, glacial acetic acid.

In some embodiments, the charge-modified starch is prepared and/or formed by forming a homogeneous reaction blend in an extruder. The charge-modified starch may be extruded and the extrudate may optionally be ground into a powder and/or pelletized. The extrudate may then be combined with chitosan, a plasticizer, and optionally a second charge-modifying agent to form a homogeneous reaction blend.

A method of the present invention may provide a formed modified biopolymer (e.g., a cross-linked, charge-modified biopolymer). In some embodiments, the method may comprise grinding, milling, pelletizing, drawing, compressing, shaping, and/or the like to provide a formed modified biopolymer of the present invention. The formed product may be of any shape and/or size. In some embodiments, a method of the present invention provides a plurality of formed products of substantially uniform size and/or shape (e.g., varying in size and/or shape by less than about 20%). In some embodiments, a method of the present invention provides a variety of particle sizes and/or shapes. In some embodiments, a method of the present invention may provide a modified biopolymer (e.g., a cross-linked, charge-modified biopolymer) that is in the form of a bead, column, sheet, powder, particle (e.g., nanoparticles, microparticles, etc.), ribbon, fiber, film, pellet, and/or the like. In some embodiments, a method of the present invention may provide a modified biopolymer in the form of a particle having a diameter in a range of about 1 micron to 2,000 microns, such as, but not limited to, in a range of about 10 microns to about 1000 microns, about 100 microns to about 1000 microns or about 300 to about 800 microns. In some embodiments, a modified biopolymer of the present invention (e.g., a cross-linked, charge-modified biopolymer) having a particle size in a range of about 300 to about 800 microns or less than about 500 microns may be suitable for use as an absorbent. In some embodiments, a modified biopolymer of the present invention (e.g., a cross-linked, charge-modified biopolymer) having a particle size in a range of about 10 to about 150 microns or less than about 100 microns may be suitable for use as an ion exchange material.

In some embodiments, a modified biopolymer of the present invention (e.g., a cross-linked, charge-modified biopolymer) may be used as and/or to prepare a consumer product, such as, but not limited to, a diaper, hygiene product, and/or wound dressing. In some embodiments, a modified biopolymer of the present invention (e.g., a cross-linked, charge-modified biopolymer) may be used as and/or to prepare an ion exchange resin and/or absorbent. Thus, in some embodiments, a modified biopolymer of the present invention may be an ion exchange resin, ion removal resin, metal chelating and/or adsorbing resin, and/or an absorbent including high performing absorbents, such as, for example, super absorbents. In some embodiments, a modified biopolymer of the present invention (e.g., a cross-linked, charge-modified biopolymer) may remove contaminants from a fluid and/or absorb a fluid.

Further exemplary industries and/or uses for a modified biopolymer of the present invention include, but are not limited to, water treatment such as, for example, single-use ion exchange for water deionization (e.g., for laboratories and/or electronics), potable water desalination, potable water contaminant and heavy metals adsorbents, and an alternative to activated carbon for dechlorination; hygienic super absorbent applications (SAP) such as, for example, baby diaper absorbents, adult incontinence absorbents, feminine hygiene absorbents; non-hygenic SAP applications such as, for example, sub-sea cable wraps, re-usable gel/ice packs, liquid waste solidification, pet pads, meat pads, concrete additives, remove water from oil and/or hydrocarbons, liquid/solid separation, waste lagoon remediation, paint solidification, agricultural and horticultural soil amendments, mortuary absorbents, whole blood or blood mixture absorbents, medical waste solidification and spill control, drug delivery systems, and wound dressings; energy such as, for example, hydraulic fracturing flowback water treatment or reuse, guar alternative hydraulic fracturing viscosifying agent, hydraulic fracturing friction reducer additive, lost circulation drilling fluid additive, oil refinery water treatment, cooling tower water softening, boiler feed water deionization, coal ash and flu vent remediation, and nuclear isotope removal; mining such as, for example, metals mining water treatment, metal removal from mining solutions, and coal mining water treatment; environmental such as, for example, pump and treat water remediation, in situ reactive barrier remediation, and sludge absorption and dewatering; packaging such as, for example, biobased packaging films and biobased structural packaging; paper such as, for example, pulp and paper strength additives and/or coatings for paper; textiles such as, for example, textile adhesives, starch ester alternative for textile manufacture, and textile non-woven thickening agents; and/or construction such as, for example, construction adhesive in wallboard. In some embodiments, a modified biopolymer of the present invention may be useful in the paper industry, cosmetics, tissue engineering, hydrogels, drug delivery applications, photonics applications, and/or as a flocculant and/or coagulant.

The present invention is explained in greater detail in the following non-limiting Examples.

EXAMPLES

Example 1.1

Extruded Charge Modified Biopolymer (Example of Citric Acid Grafted on to Starch at ~2mm Scale)

A twin screw conical extruder manufactured by DSM, a parallel twin screw extruder manufactured by Leistritz, and a parallel twin screw extruder manufactured by Wegner were used to prepare charge-modified starch. The extruder properties are provided in Table 1. Various extruders listed here allow for demonstration of scalability from lab scale to production-relevant scale. Furthermore, multiple extruders allow for transposition of process parameters across a range of extruder configurations and size.

Additionally, the parallel twin screw extruders manufactured by Lestritz and Wegner supported multiple reactions zones, allowing for increased capabilities, including: temperature, screw, and injection profiles. Examples of temperature and injection profiles may be found in Examples 1.2, 5.1, and 7, below.

TABLE 1

Extruder properties for a range of extruder configurations and sizes

| | | | | |
|---|---|---|---|---|
| Extruder Manufacturer | DSM | Thermo Fisher | Leistritz | Wegner |
| Extruder Model | Xplore | Process 11 | N/A | TX-52 |
| Residence Time | 0.25-10 mins | 0.25-5 mins | ~3 mins | ~3 mins |
| Screw Size (Screw Diameter) | 3 cm | 11 mm | 18 mm | 52 mm |
| L/D | 5 | 40 | 40 | 27 |
| Die Size | 1-2 mm | 0.5-11 mm | 1 mm & 4.5 mm | 2-4 mm |
| Rotation | Corotating Screws | Co-rotating Screws | Corotating Screws | Corotating Screws |
| Throughput | 0.05-0.2 Kg/hr | 0.1-5 Kg/hr | 0.5-8 Kg/hr | 3-30 Kg/hr |
| Type of heating | Electric | Electric | Electric | Electric |
| Number of heating zones | 1 | 8 | 8 | 1 |
| Type of Die | Single hole/circular | Single hole/circular | single holes | 1 or 2 holes |
| Additive zones | One | 8 | 3 feed ports | 2 feed ports, 1 extra for foaming agent |
| Type of cooling | Water | Water | Air | Water |

In preparing the charge-modified starch, the following parameters were varied: temperature, screw RPM, and amount of citric acid using each extruder. Table 2 sets forth the ranges for the temperature, screw RPM, and amount of citric acid tested using each extruder.

TABLE 2

Parameter ranges for charge-modified starch for each extruder.

| Parameter | Range (DSM) | Range (Leistritz) | Range (Wegner) |
|---|---|---|---|
| Temperature Ranges (° C.) | 90-150 | 100-120 | 100-125 |
| RPM Ranges (RPM) | 60-200 | 120-200 | 120-200 |
| Citric Acid Ranges (rel % to starch) | 50-100 | 50-100 | 50-100 |

Starch (Native Corn Starch, Item 18321, Batory Foods, Des Plaines Ill.), citric acid (Item 756707, Univar, Downers Grove, Ill.) as a charge modifier and plasticizer, and sodium hypophosphate (SHP) (Item S1320, Spectrum Chemical, New Brunswick, N.J.) as a catalyst were combined and hand mixed in powder form. Powder mixtures were loaded into custom powder injectors and input into the extruder feed port. Various amounts of citric acid were added to the mixture as provided in Table 2. The resulting mixture was added to the extruder as a powder at varying extrusion conditions as provided in Table 2. The powder mixture was melt-blended in the extruder to form a homogeneous blend reaction in which the citric acid was grafted onto the starch to form a charge-modified starch, termed starch citrate. In some runs, this charge-modified starch was utilized as a precursor polymer to subsequently cross-link to another biopolymer as described in Example 5. Select samples underwent a thermal post treatment following extrusion by way of vacuum oven at 120° C. for 90 mins.

Table 3 provides specific parameters tested on the DSM extruder with responses described in Table 4 and described below. Each sample was titrated to determine its charge density, and analyzed via FTIR (at wavelengths of 1720cm$^{-1}$) to determine each sample's relative carboxyl content via methods described below. Additionally, parameters such as DI uptake, and % extractables were measured as qualitative gauges of material performance.

TABLE 3

Process parameters for preparing charged-modified starch on a DSM extruder

| | Sample # | | | | |
|---|---|---|---|---|---|
| | Sample 1.1A | Sample 1.1B | Sample 1.1C | Sample 1.1D | Sample 1.1E |
| Temperature (° C.) | 140 | 140 | 100 | 140 | 125 |
| RPM | 120 | 120 | 120 | 120 | 120 |
| Post Treatment | Yes | No | Yes | Yes | Yes |
| Citric Acid (wt % relative to Starch) | 150 | 150 | 50 | 50 | 75 |
| SHP (wt % relative to Citric Acid) | 20 | 20 | 20 | 20 | 20 |

Fourier Transform Infrared Spectroscopy (FTIR) is a measure of a samples' absorbance/transmittance of wavelengths in the IR spectrum. The intensity of absorbed IR radiation at a given wavelength can be correlated to particular covalent bonds. When data is normalized to the primary alcohol peak (~1000cm$^{-1}$), relative peak intensities may be used to estimate the amount characteristic groups on the polymer, where decreasing transmittance or, inversely, increasing absorbance indicates an increased degree of reagent grafting. Bonds of interest for biopolymers modified with citric acid, such as, for example, starch citrate, include the carboxyl (R—CO$_2$H) bond at ~1713cm$^{-1}$, where decreasing transmittance or, inversely, increasing absorbance indicates an increased degree of charge density.

Back titration is a measure of charge density in anionic, charge-modified biopolymer samples. The results of this measurement technique scales with the FTIR data. As described here in Example 1.1, along with Examples 1.2, 1.3, 2.1, 3.1, 3.2, and 3.3, 0.2-0.3g of sample was exposed to 50 ml of 0.05 M NaOH solution for 1 hr. One drop of phenolphthalein (Item 3241N80, Thomas Scientific, Swedesboro, N.J.) was added and mixed into solution to act as a visual indication, approximating neutrality of the solution. A pH probe was used to monitor acid/alkaline nature of the solution during mixing and titration. The solution was then titrated with 0.05M HCl at, ~0.05 ml/second. The volume of HCl required to reach pH neutrality was recorded and assumed to be equivalent to the number of mols needed to neutralize excess NaOH in solution. The difference between the recorded mols and initial mols was then normalized to the original sample weight to yield a mol/g or meq/g charge density unit.

DI uptake is a measure of a sample's degree of swelling (i.e., its absorbency by weight under given conditions). DI uptake was measured by inserting ~0.25g sample/cm in 33 mm diameter, of 12-14 kD dialysis tubing (Item 684219, Carolina Biological, Burlington, N.C.). The ends of tubing were sealed and labeled, then exposed to 20 ml DI water per gram of sample for 72 hours. DI water was replaced every 2-3 hours over the course of a 72 hr period. Samples were then removed from the dialysis tubing and weighed. Changes in weight between the initial and final (wet) measurements were normalized to initial mass to grams of DI water absorbed per gram of sample (g/g).

Samples were then dried using a forced air oven and/or freeze dryer. Weight loss between dried sample and initial sample weight (pre dialysis) was used to calculate extractables as a % of initial sample (inverse of yield). These extractables reflect a measure of the amount of sample that elutes upon initial contact with water. This parameter qualitatively measures the mass fraction of unreacted moieties, plasticizer, and/or degraded polymeric products in a given sample.

TABLE 4

Properties of the charged-modified starch.

| Sample # | FTIR (% Trans.) | Titration (meq/g) | DI Uptake (g/g) | Extractables (%) |
|---|---|---|---|---|
| 1.1A | 36 | 5.9 | 3.4 | 89 |
| 1.1B | 96 | 1.9 | 2.8 | 87 |
| 1.1C | 59 | 2.8 | 2.7 | 37 |
| 1.1D | 48 | 4.2 | 3.1 | 30 |
| 1.1E | 49 | 3.8 | 5.4 | 49 |

As can be seen from Tables 3 and 4, charge-modified starch was produced in the process example of reactive extrusion described here. % Transmittance as measured via FTIR is shown to decrease significantly below that of starch (94.5%) while titration values are shown to increase significantly over that of starch (0meq/g).

Temperature and citric acid (charge modifying agent) concentration are the parameters where increasing inputs show increased charge density. Furthermore, inclusion of a thermal post treatment after extrusion was also studied and addition of a post treatment also shows increasing charge density. Relative similarity and relatively low values of DI uptake parameters across indicate a lack of crosslinking. Extractable values are indicative of excess reagent and generally trend with charge modifier concentration. FTIR transmittance values achieved ranged from approximately 35-98% while charge density values achieved ranged from approximately 1 to 6.5 meq/g.

Example 1.2

Extruded Charge Modified Biopolymer (Example of Citric Acid Grafted on to Starch at 18mm Scale)

Figure 2:
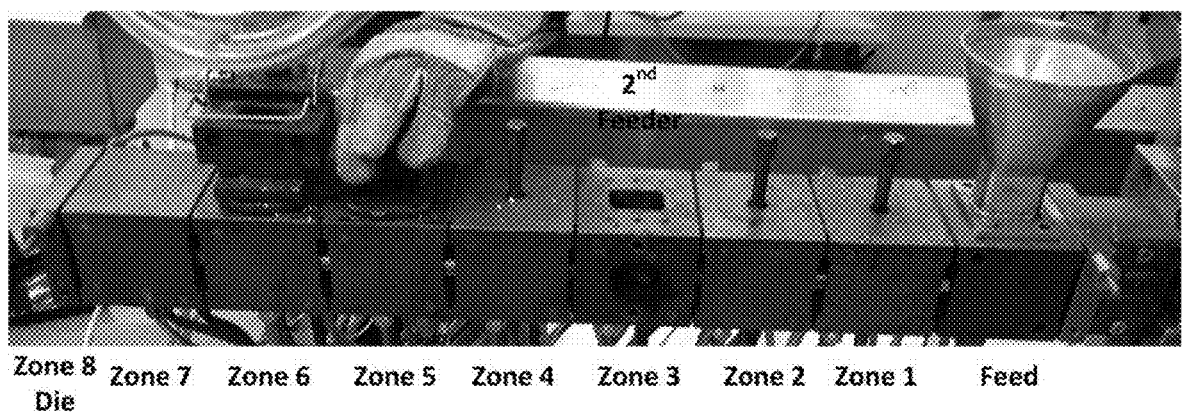
FIG. 2 illustrates a parallel twin screw extruder with multiple injection and reaction zones according to embodiments of the present invention.

A parallel twin screw extruder with multiple injection and reaction zones manufactured by Leistritz was also used to prepare charge-modified starch citrate. These experiments were performed to determine scalability and behavior of materials through varied reaction zones. The extruder properties are provided in Table 1 above. FIG. 2 illustrates the 8-zone extruder with injection ports in this configuration located prior to zone 1 and at zone 3.

Raw materials were prepared in a similar manner to extrusion as described above in Example 1.1. However, samples were mixed in 1kg units and fed using gravimetric powder feeders manufactured by Brabender (Duisburg, Germany) to account for scale. Studies below utilized multiple injection and reaction zones to simulate full-scale extrusion processes. Screw profile utilized is described in FIG. 6 (medium shear screw). Powder samples of each of the following components: starch, citric acid, and SHP were fed into the primary injection zone (prior to zone 1) where the mixture was allowed to react at 120° C. Without wishing to be bound to any particular theory, at this temperature the citric acid dehydrates to yield an anhydride that reacts faster with the free hydroxyl groups. Temperature profiles for each zone are detailed in Table 5 below. Extrusion and composition parameters for starch citrate were varied as described in Table 6 below. In some runs, extruded samples in solid form were post-treated by placing the charge-modified starch in an oven at 120° C. for 90 minutes. Specific examples of process parameters and resulting responses are shown in Tables 7 & 8 below, respectively.

TABLE 5

Temperature and injection parameters for charge-modified starch via parallel twin-screw extruder.

| | | Zone | | | | | | | |
|---|---|---|---|---|---|---|---|---|---|
| | | 1 | 2 | 3 | 4 | 5 | 6 | 7 | 8 |
| Temperature (° C.) | | 100 | 105 | 115 | 120 | 120 | 120 | 120 | 115 |
| Injection | Starch + Reagents | N/A | N/A | N/A | N/A | N/A | N/A | N/A | N/A |

TABLE 6

Parameter ranges for charge-modified starch via 18 mm, parallel twin-screw extruder.

| Temperature Ranges (° C.) | 100-120 (see Table 5) |
|---|---|
| RPM Ranges (RPM) | 120-200 |
| Citric Acid Ranges (rel % to starch) | 50-100 |

TABLE 7

Process parameters for preparing charged-modified starch via 18 mm, parallel twin-screw extruder.

| | Sample # | | | |
|---|---|---|---|---|
| | Sample 1.2A | Sample 1.2B | Sample 1.2C | Sample 1.2D |
| Temperature (° C.) | 100-120 (multiple zones) | 100-120 (multiple zones) | 100-120 (multiple zones) | 100-120 (multiple zones) |
| RPM | 100 | 160 | 100 | 170 |
| Post Treatment | Yes | Yes | Yes | Yes |
| Citric Acid (wt % relative to Starch) | 100 | 50 | 75 | 75 |
| SHP (wt % relative to starch) | 20 | 20 | 20 | 20 |

TABLE 8

Properties of the charged-modified starch.

| Sample # | FTIR (% Trans.) | Titration (meq/g) | DI Uptake (g/g) | Extractables (%) |
|---|---|---|---|---|
| 1.2A | 35 | 6.55 | 1.7 | 32 |
| 1.2B | 53 | 2.10 | 1.1 | 10.5 |
| 1.2C | 54 | 2.0 | 1.8 | 45 |
| 1.2D | 43 | 5.8 | 1.3 | 10 |

As can be seen from Tables 7 and 8, this work demonstrated the feasibility of producing charge-modified starch via a reactive extrusion process. % Transmittance as measured via FTIR is shown to decrease significantly below that of starch (94.5%) while titration values are shown to increase significantly over that of starch (0meq/g). Furthermore, it should be noted that titration and FTIR values have a positive correlation. While not wishing to be bound to any particular theory, it appears that increased RPM in this method can improve the degree of charge modification as a response to increased shear.

Example 1.3

Extruded Charge Modified Biopolymer (Example of Citric Acid Grafted on to Starch at 52mm Scale)

A parallel twin screw extruder manufactured by Wegner was used to prepare charged-modified starch and to further demonstrate scaling. The extruder properties are provided in Table 1.1 above. Screw profile utilized largely conforms to a purely conveying screw as described in FIG. 6 (low shear screw).

Raw materials for charge-modified starch were prepared in a similar manner to the extrusion processes described above. However, samples were mixed and injected in ~2kg units to account for the larger scale and continuous nature of this extruder. Extrusion and composition parameters for starch citrate were varied as described in Table 9 below. Specific examples of process parameters and resulting responses are shown respectively in Tables 10 and 11 below, respectively. In some runs, extruded samples in solid form were post-treated by placing the charge-modified starch in an oven at 120° C. for 90 minutes.

TABLE 9

Parameter ranges for charge-modified starch via 52 mm, parallel twin-screw extruder.

| | |
|---|---|
| Temperature Ranges (° C.) | 100-125 |
| RPM Ranges (RPM) | 120-200 |
| Citric Acid Ranges (wt % relative to starch) | 50-100 |

TABLE 10

Process parameters for preparing charged-modified starch via 52 mm, parallel twin screw extruder.

| | Sample # | |
|---|---|---|
| | Sample 1.3A | Sample 1.3B |
| Temperature (° C.) | 110 | 120 |
| RPM | 120 | 100 |
| Post Treatment | Yes | Yes |
| Citric Acid (wt % relative to Starch) | 66 | 66 |
| SHP (wt % relative to Citric Acid) | 20 | 20 |

TABLE 11

Properties of the charged-modified starch.

| Sample# | FTIR (% Trans.) | Titration (meq/g) | DI Uptake (g/g) | Extractables (%) |
|---|---|---|---|---|
| 1.3A | 65 | 2.9 | N/A | 64 |
| 1.3B | 69 | 2.4 | N/A | 68 |

This work demonstrated the feasibility of producing charge-modified starch via a reactive extrusion process. % Transmittance as measured via FTIR is shown to decrease significantly below that of starch (94.5%) while titration values are shown to increase significantly over that of starch (0meq/g). Examples 1.1E, 1.2C and 1.3 are used to compare samples at similar processing conditions. It is concluded from the similar responses that parameters listed in these examples are transposable across a significant range of extruder sizes (representing from laboratory benchtop to commonly-used industrial sizes).

Example 2.1

Extruded Charge Modified Biopolymer (Examples of Additional Anionic Charge Modifiers Grafted on to Starch)

In addition to citric acid, additional anionic charge modifiers are demonstrated in the example below. Starch was charged modified using maleic anhydride (Item 63200-500G-F, Sigma-Aldrich, Mo., St. Louis) a catalyst (NaOH, Reagent ACS, Item 630, GFS Chemicals, Powell Ohio), and plasticizer to form an anionic starch. Table 12 sets forth the ranges for the temperature, screw rpm, and amount of reagent tested using a Process 11, 11 mm parallel twin screw extruder as described in Example 1.1, above. Screw profile utilized is described in FIG. 6 (medium shear screw). Specific examples of process parameters and resulting responses are shown in Tables 13 and 14 below, respectively. In some runs, extruded samples in solid form were post-treated by placing the charge-modified starch in an oven at 120° C. for 90 minutes.

In addition to charge density (measured via titration), solubility of each sample was also studied. Here, purified samples (as described in the dialysis process above) are used. 0.25g of sample is mixed into in a beaker with 25ml of DI water at 60C. Beaker with mixture is set stirring on hotplate and held at 60C for 15 mins. Mixture is then centrifuged at 250g (1800 RPM & 7cm radius) for 20 mins to separate solid fraction from the liquid fraction, including dissolved solids. A pipette is then used to decant the liquid layer and discarded. Aluminum weigh pans stored in a desiccator and with predetermined weights are used to collect remaining solids. Weigh pans and solids are then dried in a forced air oven for 48 hrs at 40° C. Weigh pans and samples are removed from the forced air oven and immediately weighed. Sample weights as a fraction of initial weights are recorded as a % Solubility.

TABLE 12

Parameter ranges of the anionic-modified starch on an 11 mm, parallel twin screw extruder.

| | |
|---|---|
| Temperature Ranges (° C.) | 85-140 |
| RPM Ranges (RPM) | 10-500 |
| Maleic Anhydride Ranges (wt % relative to starch) | 5-120 |
| Catalyst (NaOH) Ranges (wt % relative to starch | 2-60 |
| Plasticizer Ranges (wt % relative to starch) | Water, Glycerol, & Water/Glycerol mixes at 40% |

TABLE 13

Process parameters for preparing anionic-modified starch via 11 mm, parallel twin screw extruder.

| | Example 2.1A | Example 2.1B |
|---|---|---|
| Temperature (° C.) | 110 | 110 |
| RPM (RPM) | 50 | 50 |
| Post Treatment | No | No |
| Maleic Anhydride Ranges (wt % relative to starch) | 30 | 60 |
| Catalyst (NaOH) Ranges (wt % relative to starch | 12 | 24 |
| Plasticizer (wt % relative to starch) | Water (40%) | Water (40%) |

TABLE 14

Properties of the Anionic Modified Starch

| Sample# | FTIR (% Trans) | Titration (meq/g) | Solubility (%) |
|---|---|---|---|
| 2.1A | 83 | 3.26 | 76 |
| 2.1B | 73 | 5.11 | 84 |

Data indicated that a charge-modified starch was produced via a reactive extrusion process. % Transmittance as measured via FTIR is shown to decrease significantly below that of starch (94.5%) while titration and solubility values are shown to increase significantly over that of starch (0meq/g and 7%, respectively). Ranges of charge density varied from 1.3-6.3 meq/g, and solubility varied from 27-86%. The level of charge modification of the starch increased with increasing reagent concentration. Data are further confirmed via increasing solubility with increasing charge density.

Example 2.2

Extruded Charge Modified Biopolymer (Examples of Cationic Charge Modifiers Grafted on to Starch)

In addition to anionc charges, starch was charge-modified to form a cationic starch. The cationic charge-modified starch was prepared by varying the following parameters: temperature, screw rpm, amount of charge modifying reagent (glycidyltrimethylammonium chloride [Sigma Aldrich Item 50053-1L]), catalyst (Sodium Hydroxide) and plasticizer content. Table 15 sets forth the ranges for the studied parameters in the Leistritz, 11 mm extruder.

TABLE 15

Parameter ranges of the anionic-modified starch on an 11 mm, parallel twin screw extruder.

| | |
|---|---|
| Temperature Ranges (° C.) | 85-140 |
| RPM Ranges (RPM) | 10-500 |
| glycidyltrimethylammonium chloride Ranges (wt % relative to starch) | 5-150 |
| Catalyst (NaOH) Ranges (wt % relative to starch | 2-60 |
| Plasticizer Ranges (wt % relative to starch) | Water, Glycerol, & Water/Glycerol mixes at 40% |

Starch powder was mixed with a catalyst (NaOH) in powder form. Plasticizer was then added to the mixture containing the starch and catalyst and mixed well by hand. The mixture was then input into the extruder.

Table 16 provides specific parameters tested with test responses described in Table 17. Note, temperature settings were set to apply a uniform temperature for all heating zones. Although temperature profiles were utilized in other experiments, they are not detailed here. Screw profile utilized is described in FIG. 6 (medium shear screw). Each sample was tested to determine its charge density (degree of substitution) via elemental analysis (measuring nitrogen).

Elemental analysis may be used to measure charge density for cationic charge-modified biopolymer samples, whereas titration may be used to measure charge density for anionic charge-modified biopolymer samples. Elemental analysis was carried out by means of Perkin Elmer 2400 CHNS Analyzer: The Perkin Elmer 2400 was used to determine total elemental carbon, nitrogen, hydrogen, or sulfur by total combustion. The Degree of Substitution (DS) was determined by nitrogen and calculated according to Equation (1) below:

$$DS = 162.15 x\% N / 1401 - 151.64 x\% N \quad (1),$$

where DS is the degree of substitution and % N is the measured nitrogen content. Furthermore, % N is nearly 0% but a non-zero number (e.g. 0.002). It is subtracted from all measurements for precision.

TABLE 16

Process and formulation parameters for preparing cationic charge-modified starch.

| | Sample # | | | |
|---|---|---|---|---|
| | Sample 2.2A | Sample 2.2B | Sample 2.2C | Sample 2.2D |
| Temperature (° C.) | 90 | 120 | 90 | 90 |
| Plasticizer (wt % relative to starch) | Water (40%) | Water (40%) | Water (40%) | Water (40%) |
| RPM | 100 | 120 | 50 | 50 |
| Post Treatment | No | No | No | Yes |
| glycidyltrimethylammonium chloride (wt % relative to Starch) | 4 | 85 | 30 | 30 |
| NaOH (wt % relative to Starch) | 1.2 | 24 | 12 | 12 |

TABLE 17

Properties of the cationic charged-modified starch.

| Sample # | Degree of Substitution* | Solubility (%) |
|---|---|---|
| 2.2A | 0.035 | 28 |
| 2.2B | 0.12 | 68 |
| 2.2C | 0.19 | 76 |
| 2.2D | 0.21 | 13 |

*Degree of substitution as measured by nitrogen content

Once again, a charge-modified starch was produced in this reactive extrusion process. Degree of substitution and solubility values were significantly greater than that of starch (0 DS, and 0.4% solubility, respectively) and demonstrate charge modification of a cationic starch via reactive extrusion. A range of DS values are produced. The DS values achieved here are significantly higher than previously reported values of DS for cationic starch produced via reactive extrusion.

In example 2.2D, inclusion of post treatment shows increased degree of substitution with simultaneous reduction in solubility indicating presence of cross linking as discussed in later examples.

Example 3.1

Extruded Charge Modified Biopolymer (Demonstration of Charge Grafting onto Hemicellulose)

In addition to starch, additional biopolymers were utilized to demonstrate charge modification. Hemicellulose (Xylan from Beechwood >=90%, Item X4252, Sigma Aldrich, St. Louis Mo.) was charge modified with citric acid to form an anionic hemicellulose using the DSM extruder described in Example 1.1. In preparing the charge-modified hemicellulose, the following parameters were varied: temperature, screw rpm, and amount of citric acid. Table 18 sets forth the ranges for the temperature, screw rpm, and amount of citric acid tested using the twin screw conical extruder.

TABLE 18

Parameter ranges for charge-modified hemicellulose via twin screw conical extruder.

| | |
|---|---|
| Temperature Ranges (° C.) | 90-150 |
| RPM Ranges (RPM) | 50-200 |

TABLE 18-continued

Parameter ranges for charge-modified hemicellulose via twin screw conical extruder.

| | |
|---|---|
| Citric Acid Ranges (wt % relative to hemicellulose) | 40-150 |

Figure 3:
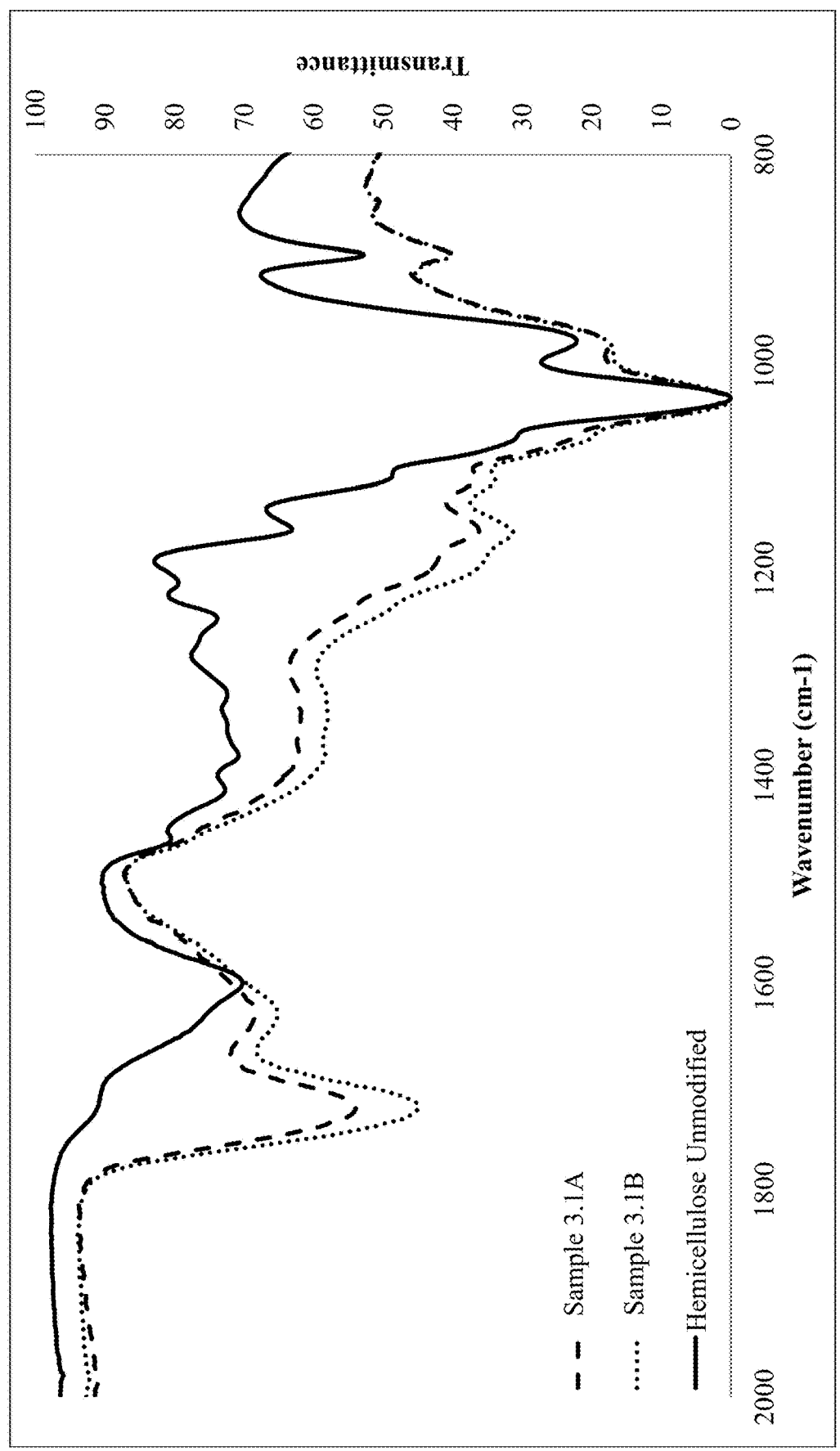
FIG. 3 illustrates FTIR spectra for unmodified hemicellulose and charge-modified hemicellulose according to embodiments of the present invention.

Reagents in powder form were hand mixed in 50 g batches, loaded into the extruder using custom powder injectors, and fed into the extruder at feed rates determined to be relatively and qualitatively consistent. Table 19 provides specific parameters tested with test responses described in Table 20. The FTIR spectra for the charge-modified hemicellulose and for unmodified hemicellulose is provided in FIG. 3. Charge density values are reported according to the titration method described in Example 1.1. It should be noted that in this example, charge density values of the raw materials are measured and then subtracted from measured values to show a degree of change in charge density above that of the raw biopolymer.

TABLE 19

Process and formulation parameters for preparing charge-modified hemicellulose.

| | Sample # | |
|---|---|---|
| | Sample 3.1A | Sample 3.1B |
| Temperature (° C.) | 140 | 140 |
| RPM | 120 | 120 |
| Post Treatment | No | Yes |
| Citric Acid (wt % relative to Hemicellulose) | 150 | 150 |
| SHP (wt % relative to Citric Acid) | 20 | 20 |

TABLE 20

Properties of the charged-modified hemicellulose.

| Sample # | FTIR (% Trans.) | Titration (meq/g) |
|---|---|---|
| 3.1A | 81.4% | 1.66 |
| 3.1B | 53.4% | 4.68 |

A charge-modified hemicellulose was produced via reactive extrusion. FTIR analysis shows % Transmission values significantly lower than that of unmodified hemicellulose (91%) and titration values significantly greater than that of unmodified hemicellulose (0meq/g), indicating charge modification of the hemicellulose.

Example 3.2

Extruded Charge Modified Biopolymer (Demonstration of Charge Grafting onto Pectin)

Pectin (Item 76282, Sigma Aldrich, St. Louis, Mo.) was charge modified to increase the anionic property of pectin by grafting additional carboxylic acid groups onto pectin using the DSM extruder described in Example 1.1. Experimental methods followed those in Example 3.1. Table 21 sets forth the ranges for the temperature, screw rpm, and amount of citric acid tested using the twin screw conical extruder.

TABLE 21

Parameter ranges for charge-modified pectin via twin screw conical extruder.

| | |
|---|---|
| Temperature Ranges (° C.) | 90-150 |
| RPM Ranges (RPM) | 50-200 |
| Citric Acid Ranges (wt % relative to pectin) | 40-150 |

Figure 4:
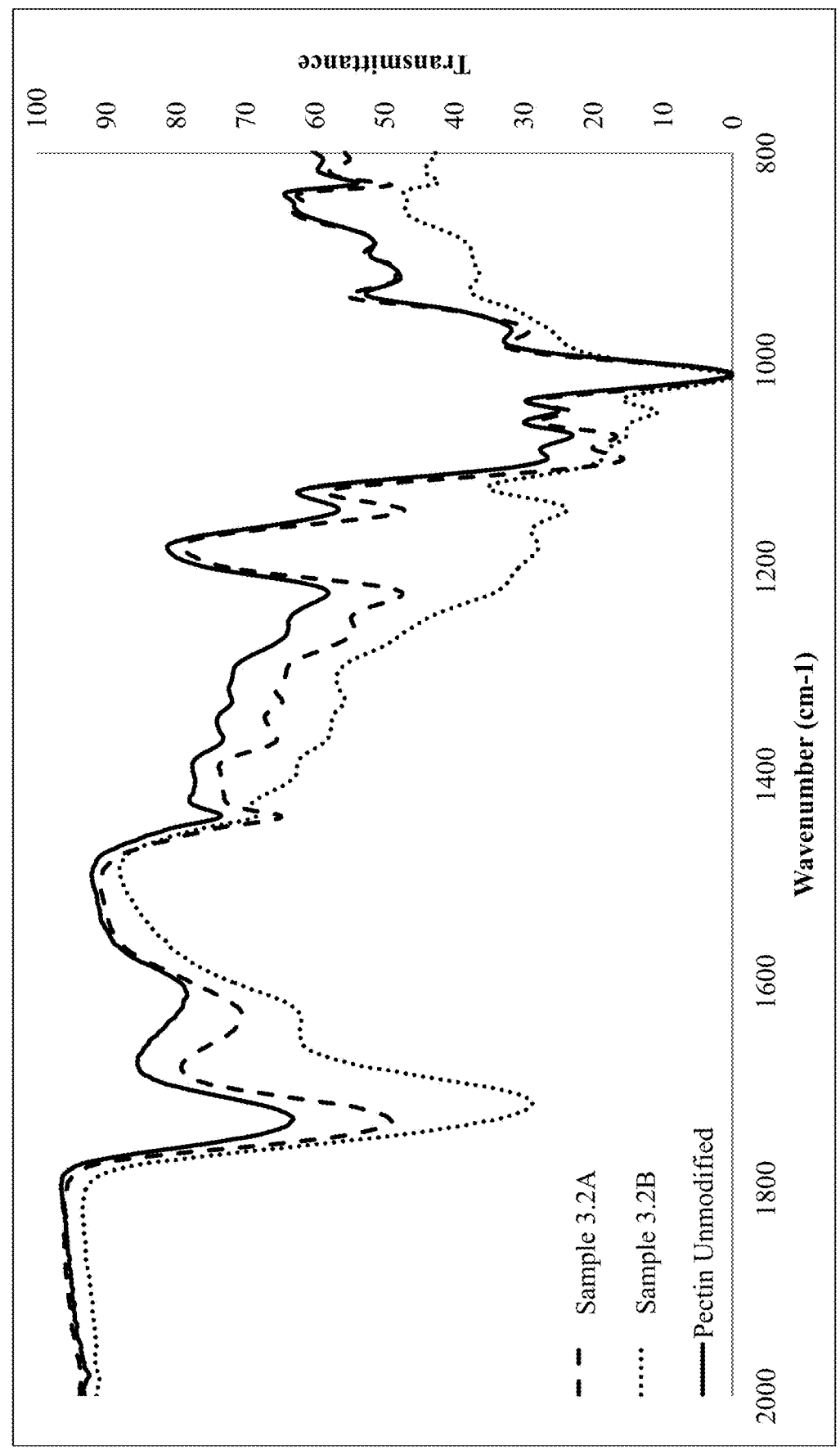
FIG. 4 illustrates FTIR spectra for unmodified pectin and charge-modified pectin according to embodiments of the present invention.

Table 22 provides specific parameters tested with test responses described in Table 23. If the sample underwent a post treatment, then the sample was placed in a vacuum oven at 120° C. for 90 mins. Each sample was tested to determine its charge density (meq/g), and absorbance/transmittance via Fourier Transform Infrared Spectroscopy (FTIR) at $1720 cm^{-1}$. The FTIR spectra for the charge-modified pectin and for unmodified pectin is provided in FIG. 4. Charge density values are reported according to the titration method described in Example 1.1. It should be noted that in this example, charge density values of the raw materials are measured and then subtracted from measured values to show a degree of change in charge density above that of the raw biopolymer.

TABLE 22

Process and formulation parameters for preparing charge-modified pectin.

| | Sample # | |
|---|---|---|
| | Sample 3.2A | Sample 3.2B |
| Temperature (° C.) | 140 | 140 |
| RPM | 120 | 120 |
| Post Treatment | No | Yes |
| Citric Acid (% relative to pectin) | 150 | 150 |
| SHP (% relative to Citric Acid) | 20 | 20 |

TABLE 23

Properties of the charged-modified pectin.

| Sample # | FTIR (% Trans.) | Titration (meq/g) |
|---|---|---|
| 3.2A | 59.1 | 4.96 |
| 3.2B | 26.6 | 5.72 |

A charge-modified pectin was produced via reactive extrusion. FTIR analysis shows % Transmission values significantly lower than that of unmodified pectin (63%) and titration values significantly greater than that of unmodified pectin (0meq/g), indicating charge modification of the pectin.

Example 3.3

Extruded Charge Modified Biopolymer (Demonstration of Charge Grafting onto Soy Protein)

Soy protein was charge modified to form an anionic soy protein using the DSM extruder described in Example 1.1. In preparing the charge-modified soy protein, Experimental methods followed those in Example 3.1. Table 24 sets forth the ranges for the temperature, screw rpm, and amount of citric acid tested using the twin screw conical extruder.

TABLE 24

Parameter ranges for charge-modified soy protein via twin screw conical extruder.

| | |
|---|---|
| Temperature Ranges (° C.) | 90-150 |
| RPM Ranges (RPM) | 50-200 |
| Citric Acid Ranges (wt % relative to soy protein) | 40-150 |

Figure 5:
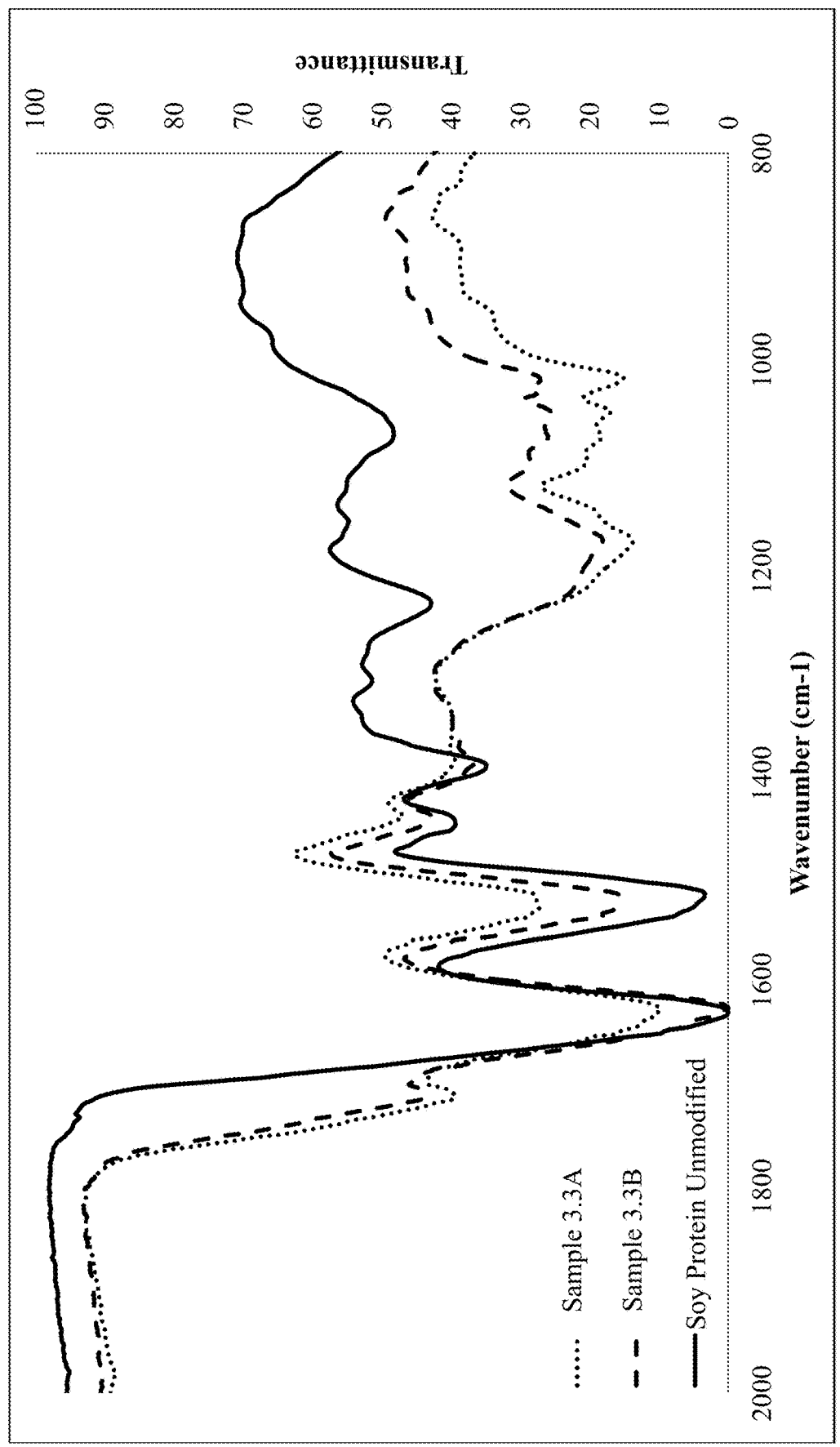
FIG. 5 illustrates FTIR spectra for unmodified soy protein and charge-modified soy protein according to embodiments of the present invention.

Table 25 provides specific parameters tested with test responses described in Table 26. If the sample underwent a post treatment, then the sample was placed in a vacuum oven at 120° C. for 90 mins. Each sample was tested to determine its charge density (meq/g), and absorbance/transmittance via Fourier Transform Infrared Spectroscopy (FTIR) at 1720cm$^{-1}$. The FTIR spectra for the charge-modified soy protein and for unmodified soy protein is provided in FIG. 5. Charge density values are reported according to the titration method described in Example 1.1. It should be noted that in this example, charge density values of the raw materials are measured and then subtracted from measured values to show a degree of change in charge density above that of the raw biopolymer.

TABLE 25

Process and formulation parameters for preparing charge-modified soy protein.

| | Sample # | |
|---|---|---|
| | Sample 3.3A | Sample 3.3B |
| Temperature (° C.) | 140 | 140 |
| RPM | 120 | 120 |
| Post Treatment | No | Yes |
| Citric Acid (wt % relative to Hemicellulose) | 150 | 150 |
| SHP (wt % relative to soy protein) | 20 | 20 |

TABLE 26

Properties of the charged-modified soy protein.

| Sample # | FTIR (% Trans.) | Titration (meq/g) |
|---|---|---|
| 3.3A | 68.4 | 1.66 |
| 3.3B | 42.8 | 4.68 |

A charge-modified soy protein was produced via reactive extrusion. FTIR analysis shows % Transmission values significantly lower than that of unmodified soy protein (93%) and titration values significantly greater than that of unmodified pectin (0meq/g), indicating charge modification of the soy protein. Charge modification was enhanced by thermal post treatment.

Example 4.1

Extruded Cross Linked Biopolymer (Demonstration of Starch Modified with a Range of Cross Linkers)

In addition to charge modifiers, cross-linkers were utilized to form a cross-linked starch using the DSM extruder described in Example 1.1. In preparing the cross-linked starch, experimental methods followed those in Example 1.1. The following parameters are varied: temperature, screw rpm, and the amount of cross linker. In this example, water was used as the plasticizer at the level of 40 wt % relative to starch. Cross linkers included: Epichlorohydrin (EPI, >=99% (GC), Item 45340, Sigma-Aldrich, St. Louis, Mo.), Poly(ethylene glycol) diglycidyl ether (PEDGE, Avg. MN 500, Item 475696, Sigma-Aldrich, St. Louis, Mo.), and Poly(propylene glycol) diglycidyl ether (PPDGE, Avg. CA. 640, Item 406740, Sigma-Aldrich, MO, St. Louis) with sodium hydroxide as catalyst. Table 27 sets forth the ranges for the temperature, screw rpm, and amount of cross-linker tested using the twin screw conical extruder. Table 28 provides specific parameters tested with test responses described in Table 29.

TABLE 27

Process and formulation ranges for preparing cross-linked starch.

| | |
|---|---|
| Temperature (° C.) | 80-110 |
| RPM | 50-120 |
| Crosslinker | Epichlorohydrin, PEDGE, and PPDGE |
| Crosslinker (wt % relative to starch) | 0.01-0.1 |
| NaOH (wt % relative to Starch) | 0.005-0.2 |

TABLE 28

Process and formulation parameters for preparing cross-linked starch.

| | Sample 4.1A | Sample 4.1B | Sample 4.1C |
|---|---|---|---|
| Temperature (° C.) | 90 | 90 | 90 |
| RPM | 120 | 120 | 120 |
| Post-treatment | No | No | No |
| Crosslinker | EPI | PEDGE | PPDGE |
| Crosslinker (wt % relative to starch) | 0.1 | 0.1 | 0.1 |
| NaOH (wt % relative to Starch) | 0.2 | 0.2 | 0.2 |
| Plasticizer (40% relative to starch) | Water | Water | Water |

TABLE 29

Properties of cross-linked starch.

| | Solubility (%) | Swelling (g/g) |
|---|---|---|
| Sample 4.1A | 1.6 | 0.35 |
| Sample 4.1B | 2.53 | 2.67 |
| Sample 4.1C | 4.07 | 3.15 |

Here, cross-linked biopolymers were produced via a reactive extrusion process. Reactive extrusion of starch with cross linkers show: as cross linker chain length (molecular weight) is increased (EPI<PEDGE<PPDGE), swelling values improve beyond that of uncross-linked starch (0.4g/g) and solubility values approach that of uncross-linked starch (7%).

Example 4.2

Extruded, Cross Linked, Charge Modified Biopolymer (Demonstration of Cationic Starch Modified with Various Cross Linkers)

In addition to starch, charge-modified starch were utilized to form a cross-linked, charge-modified starch using the DSM extruder described in Example 1.1. In preparing the cross-linked, charge-modified starch, experimental methods followed those in Example 4.1. Aquaflocc 330 AW, manufactured by Aquasol Corp (Rock Hill, S.C.) was used as the cationic starch in this example. Additional commercially-available cationic starches, as well as cationic starches as described in Example 2.2 were also utilized. The following parameters are varied: temperature, screw rpm, amount of cross linker, and plasticizer. Cross linkers included: Epichlorohydrin, Poly(ethylene glycol) diglycidyl ether, and Poly (propylene glycol) diglycidyl ether with sodium hydroxide as catalyst. Table 30 sets forth the ranges for the temperature, screw rpm, and amount of cross-linker tested using the twin screw conical extruder. Table 31 provides specific parameters tested with test responses described in Table 32.

TABLE 30

Process and formulation ranges for preparing cross-linked, cationic starch.

| | |
|---|---|
| Temperature (° C.) | 80-160 |
| RPM | 10-300 |
| Crosslinker (wt % relative to starch) | 0.0001 to 10 |
| NaOH (wt % relative to Starch) | 0.001 to 20 |
| Plasticizer (%) | Water, Glycerol (20-50%) |

TABLE 31

Process and formulation parameters for preparing cross-linked, cationic starch.

| | Sample 4.2A | Sample 4.2B | Sample 4.2C |
|---|---|---|---|
| Temperature (° C.) | 90 | 90 | 90 |
| RPM | 120 | 120 | 120 |
| Post-treatment | No | No | No |
| Crosslinker | EPI | PEDGE | PPDGE |
| Crosslinker (wt % relative to starch) | 0.1 | 0.1 | 0.1 |
| NaOH (wt % relative to Starch) | 0.2 | 0.2 | 0.2 |
| Plasticizer (% relative to starch) | Water (40%) | Water (40%) | Water (40%) |

TABLE 32

Properties of cross-linked cationic starch.

| | Solubility (%) | Swelling (g/g) |
|---|---|---|
| Sample 4.2A | 12.6 | 1.9 |
| Sample 4.2B | 39.9 | 11.2 |
| Sample 4.2C | 40.3 | 14.7 |

Here, cross linked, charge modified biopolymers were created via reactive extrusion. Solubility results show values significantly lower than that of the raw material (84%). Here, decreasing solubility indicates increased degree of cross-linking. Swelling results may be higher or lower than that of the raw material (4.4 g/g) depending on degree of cross-linking.

Example 5.1

Extruded Cross Linked, Charge Modified Biopolymer (Demonstration of Cross Linking Multiple Biopolymers Using 2-Step, in Line Method)

To demonstrate crosslinking two charge modified biopolymers, cross-linked, charged-modified starch citrate chitosan was prepared using a 2-step inline process using the Leistritz, 18mm extruder as described in Example 1.1. Grafting citric acid onto starch provides an anionic charge, which changes the degree of charge as can be measured using back titration (meq/g). Acetic acid may be used to protonate chitosan upon mixing, thereby providing a cationic charge on the chitosan. The charge-modified chitosan may be assumed to be partially (i.e., 50% or more) or fully (100%) protonated due to its solubility in water.

Furthermore, the extruder having multiple zones as shown in FIG. 2, allows for implementation of temperature and injection profiles. Extrusion and composition parameters for preparing cross-linked, charge-modified starch citrate chitosan were varied as described in Table 33. Here, powder samples of starch, citric acid, and SHP were fed into the initial injection zone (Step 1), while chitosan (Trading Resources, Cocoa Beach, Fla.), acetic acid (Sigma Aldrich, Item# A6283, St. Louis, Mo.), and plasticizers were simultaneously added in at injection zone 3 (Step 2) as shown in Table 34 below. Reactions zones 1-2 were used for charge modification, while reaction zones 3-8 were used for cross-linking the charge modified-starch to charge-modified chitosan. Temperature profiles for each zone are provided in Table 34 below. Screw profile utilized largely conforms to the medium shear screw as described in FIG. 6 (medium shear screw). After the graft reaction of citric acid onto starch, the temperature was decreased to 100° C. to allow for the injection of protonated chitosan inside the extruder in zone 3 before raising the temperature to 105° C. and 110° C. in zones 4 and 5, respectively, to initiate the crosslinking reaction between the starch carboxylate and the free amine groups on the backbone of chitosan. In some runs, extruded samples in solid form were post-treated by placing the charge-modified, cross-linked polymer in an oven at 120° C. for 90 minutes. The simultaneous injection of two mixtures demonstrated below is defined as a 2-step, inline reaction.

TABLE 33

Parameter ranges for cross-linked starch citrate chitosan via parallel twin screw extruder.

| | |
|---|---|
| Temperature Ranges (° C.) | 100-120 (see Table 34) |
| RPM Ranges (RPM) | 140-170 |
| Chitosan Ranges (wt % relative to Starch) | 100 |
| Acetic Acid Ranges (wt % relative to Chitosan) | 33 |
| Starch Citrate Ranges (wt % relative to Chitosan) | 100 |
| Plasticizer Types | Citric Acid |
| Plasticizer Ranges (wt % relative to Chitosan) | 90-140 |

TABLE 34

Example of temperature and injection profile for charge-modified starch cross-linked to another biopolymer via parallel twin-screw extruder.

| | | Zone | | | | | | | |
|---|---|---|---|---|---|---|---|---|---|
| | | 1 | 2 | 3 | 4 | 5 | 6 | 7 | 8 |
| Temperature (° C.) | | 120 | 120 | 100 | 105 | 110 | 110 | 110 | 105 |
| Injection | Starch + Reagents | N/A | N/A | Chitosan + Reagents | N/A | N/A | N/A | N/A | N/A |

Specific examples of process parameters and resulting responses are shown in Tables 35 and 36 below, respectively. The methods for determining the measured responses (e.g. solubility, DI uptake, and extractables) are described in Example 1. For FTIR analysis, bonds of interest for charged-modified starch, cross linked to chitosan system include the Amide-Carbonyl (R—CO—CNH—R) stretch at ~1650cm$^{-1}$.

TABLE 35

Process parameters for preparing cross-linked, charge-modified starch citrate chitosan.

| | Sample # | | |
|---|---|---|---|
| | Sample 5.1A | Sample 5.1B | Sample 5.1C |
| Temperature (° C.) | 100-120 (multiple zones) | 100-120 (multiple zones) | 100-120 (multiple zones) |
| RPM | 140 | 140 | 170 |
| Post Treatment | Yes | No | Yes |
| Reaction Type | 2-step inline | 2-step inline | 2-step inline |
| Plasticizer Type | Citric Acid | Citric Acid | Citric Acid |
| Plasticizer (wt % relative to Chitosan) | 75 | 75 | 75 |
| Starch Citrate (wt % relative to Chitosan) | 100 | 100 | 100 |
| Acetic Acid (wt % relative to Chitosan) | 33 | 33 | 33 |

TABLE 36

Properties of the cross-linked, charge-modified starch citrate chitosan.

| Sample # | Solubility (%) | FTIR (% Trans) | DI Uptake (g/g) | Extractables (%) |
|---|---|---|---|---|
| 5.1A | 4.1 | 67.5 | 2.6 | 19 |
| 5.1B | 2.4 | 65.4 | 9.5 | 69 |
| 5.1C | 4.1 | 68.2 | 1.9 | 19 |

As described in Example 2, charge modified polymers without cross-linking show increasing solubility with increasing charge density (>5% and up to 100%). Due to the presence of charge modified starch and charge modified chitosan, solubility values <5% indicate presence of cross-linking. FTIR analysis confirms presence of the amide-carbonyl stretch where a modified and unmodified chitosan shows transmission values of 26% and modified and unmodified starch shows values of 5%. % Transmission values above 26% indicate presence of charge modified starch cross linked to charge modified chitosan, confirming the ability to form a charge modified biopolymer cross linked to another biopolymer in a 2-step, in-line method.

Example 5.2

Extruded Cross Linked, Charge Modified Biopolymer (Demonstration of Cross Linking Multiple Biopolymers Using 2-Step, 2-Pass Method)

To demonstrate a method where charged-modified biopolymers may be produced and subsequently cross linked to another biopolymer, charged-modified starches as prepared in Example 1.1 were cross-linked with chitosan by mixing powdered starch citrate (i.e., the citric acid-modified starch) with acetic acid, chitosan, and plasticizer so that the mixture was in powdered form. To obtain the powdered charge-modified starch, the charge-modified starch was ground using a blender to sugar/starch consistency where there were no visible chunks/inconsistencies in the powder mixtures. At least one plasticizer selected from: glycerol [Item#0854, Amresco, Solon, Ohio], citric acid, and polyethylene glycol [molecular weights of 400, 800, 20,000, Sigma Aldrich, St. Louis, Mo.] was added to the mixture comprising of starch citrate, acetic acid, chitosan, and plasticizer to induce melt blending during the extrusion process. The resulting powder mixture was added to the extruder described in Example 1.1 in a method resembling the process for preparing charge-modified starch as described in Example 1.1. Extrusion parameters and compositions were modified according to Table 37 below.

TABLE 37

Parameter ranges for cross-linked, charge-modified starch citrate chitosan via twin screw conical extruder.

| Temperature Ranges (° C.) | 90-130 |
|---|---|
| RPM Ranges (RPM) | 60-200 |
| Chitosan Ranges (rel % to Starch) | 50-150 |
| Acetic Acid Ranges (rel % to Chitosan) | 5-100 |
| Starch Citrate Ranges (rel % to Chitosan) | 150-250 |
| Plasticizer Types | Glycerol Citric Acid, Water |
| Plasticizer Ranges (rel % to Chitosan) | 120-275 |

Completion of the reaction in two steps is defined here as a "2-step, 2-pass" reaction. Examples of process parameters for cross-linked, charge-modified starch citrate chitosan and measured responses are shown in Tables 38 and 39, respectively below. The charge-modified starch used to prepare the cross-linked, charge-modified starch citrate chitosan had previously been prepared as described in Example 1 according to parameters described in sample 1.1A.

Each sample was analyzed via FTIR to characterize chemical identity, determine its deionized water (DI) uptake, and to measure extractables (inverse of yield) following the methods described in Example 1.

TABLE 38

Process parameters for preparing cross-linked, charge-modified starch citrate chitosan.

| | Sample # | |
|---|---|---|
| | Sample 5.2A | Sample 5.2B |
| Extruder | DSM | DSM |
| Temperature (° C.) | 100 | 110 |
| RPM | 120 | 120 |
| Post Treatment | No | No |
| Reaction Type | 2-step, 2-pass | 2-step, 2-pass |
| Plasticizer Type | Citric acid | Citric Acid |
| Plasticizer (wt % relative to Chitosan) | 175 | 175 |
| Starch Citrate (wt % relative to Chitosan) | 100 | 250 |
| Acetic Acid (wt % relative to Chitosan) | 33 | 33 |

TABLE 39

Properties of the cross-linked starch citrate chitosan.

| Sample # | FTIR (% Trans) | DI Uptake (g/g) | Extractables (%) |
|---|---|---|---|
| 5.2A | 59.4 | 2.7 | 73 |
| 5.2B | 62.6 | 1.5 | 61 |

As described in Example 5.1, a citric acid modified starch cross-linked to chitosan may show the amide-carbonyl (R—CO—CNH—R) stretch at ~1650cm$^{-1}$ when subjected to FTIR analysis. FTIR analysis confirms presence of the amide-carbonyl stretch where a modified and unmodified chitosan shows transmission values of 26% and modified and unmodified starch shows values of 5%. Here, % Transmission values of 59 and 62% (>26%) indicate presence of charge modified starch cross linked to charge modified chitosan and confirming the ability to form a charge modified biopolymer cross linked to another biopolymer in a 2-step, 2-pass method.

Example 5.3

Extruded Cross Linked, Charge Modified Biopolymer (Demonstration of Cross Linking Multiple Biopolymers Using all-in-One Method)

To demonstrate simultaneous charge modification and cross-linking via reactive extrusion, all raw materials (i.e., starch, citric acid, SHP, chitosan, acetic acid, and plasticizer as described in Examples 5.1 and 5.2) were injected simultaneously in powder form to induce charge modification and cross-linking reactions in one injection through multiple extruders (defined here as an "all-in-one" reaction). Here, the mixture of all raw materials was added to the extruder described in Example 1.1 and 1.3 in a method resembling the process for preparing charge-modified starch as described in Example 1.1 and 1.3. Extrusion parameters and compositions were modified according to Table 40 below. Examples of process parameters for preparing cross-linked, charge-modified starch citrate chitosan are shown in Table 41 below with measured responses provided in Table 42. The methods for determining the measured responses are provided in Examples 1 and 2.

TABLE 40

Parameter ranges for cross-linked, charge-modified starch citrate chitosan via twin screw conical extruder and 52 mm, parallel twin screw extruder.

| Extruder | DSM | Wegner TX-52 |
|---|---|---|
| Temperature Ranges (° C.) | 90-130 | 105-130 |
| RPM Ranges (RPM) | 60-200 | 120-250 |
| Chitosan Ranges (wt % relative to Starch) | 50-150 | 50-75 |
| Acetic Acid Ranges (wt % relative to Chitosan) | 5-100 | N/A |
| Starch Ranges (wt % relative to Chitosan) | 150-250 | 100 |
| Plasticizer Types | Glycerol Citric Acid, Poly Ethylene Glycol, Water | Citric Acid, Water |
| Plasticizer Ranges (wt % relative to Chitosan) | 120-275 | 100-130 |

TABLE 41

Process parameters for preparing cross-linked, charge-modified starch citrate chitosan.

| | Sample 5.3A | Sample 5.3B | Sample 5.3C | Sample 5.3D |
|---|---|---|---|---|
| Extruder | DSM | DSM | Wegner TX-52 | Wegner TX-52 |
| Temperature (° C.) | 100 | 133 | 120 | 110 |
| RPM | 120 | 120 | 120 | 200 |
| Post Treatment | No | No | No | No |
| Reaction Type | All-in-one | All-in-one | All-in-one | All-in-one |
| Plasticizer Type | Citric Acid | Glycerol | Citric Acid | Citric Acid |
| Plasticizer (% rel to Chitosan) | 175 | 175 | 100 | 100 |
| Starch (% rel to Chitosan) | 150 | 100 | 150 | 150 |
| Citric Acid (% rel to Starch) | 66 | 66 | N/A | N/A |
| SHP (% rel to Starch) | 20 | 20 | 20 | 20 |
| Acetic Acid (% rel to Chitosan) | 33 | 33 | N/A | N.A |

TABLE 42

Properties of the cross-linked, charge-modified starch citrate chitosan.

| Sample # | FTIR (% Trans) | DI Uptake (g/g) | Extractables (%) |
|---|---|---|---|
| 5.3A | 58.8 | 4.3 | 58 |
| 5.3B | 66.9 | 4.9 | 54 |
| 5.3C | 67.2 | N/A | 67 |
| 5.3D | 65.3 | N/A | 65 |

As described in Example 5.1 and 5.2, a citric acid modified starch cross-linked to chitosan may show the Amide-Carbonyl (R—CO—CNH—R) stretch at ~1650cm$^{-1}$ when subjected to FTIR analysis. The presence of carbonyl groups indicate citric acid charge modification on starch, and the presence of the Amide-carbonyl group indicates cross-linking. FTIR analysis confirms presence of the Amide-carbonyl stretch where a modified and unmodified chitosan shows transmission values of 26% and modified and unmodified starch shows values of 5%. Here, % Transmission values of >26% indicate simultaneous charge modification and cross linking of charge modified starch cross linked to chitosan to form a charge modified biopolymer cross linked to another biopolymer in an all-in-one method.

Example 6

Example of Modified Biopolymer for IEX Application (Demonstration of Salt/Heavy Metal Uptake)

To demonstrate ion removal capabilities of a charge modified, cross linked biopolymer, citric acid-modified starch cross-linked to chitosan were prepared according to Examples 5.1, 5.2, and 5.3. Samples were tested for their salt uptake capacity measured by conductivity and ash content post exposure to a saline solution.

Ash content testing is a measure of residual inorganic material in a sample upon exposure to high temperatures. 0.3g of samples was exposed to a 10% saline (NaCl) solution for 5 minutes, then squeezed by hand to remove absorbed liquids. Samples were then transferred to clean, dry, glass vials whose weights were previously recorded. Samples were then exposed to high temperatures in a muffle furnace (Vulcan, Model 3-550), for 4 hours at 575° C. following TAPPI Standard: T211 om-02 —"Ash in wood, pulp, paper and paperboard, combustion at 525° C.". To determine the ash content, the vial weight was subtracted from the final recorded weight comprising of vial and ash. Final ash weight was assumed to be residual captured salts where the final ash weight is divided by the initial sample weight to normalize data to a g NaCl/g sample (g/g) format.

Conductivity is a measure of ionic mobility in a given solution. Reductions in conductivity may be attributed to captured ions, changes in system energy (i.e., temperature, pressure, etc.), and/or potential of dissolved ions (i.e., pH changes in presence of acids/bases). Samples (0.3g) were exposed to 25ml of 10% NaCl solution where initial conductivity (Metler-Toledo conductivity instrument [model #51302530]) was measured to be 142 mS/cm with a standard deviation of 3.7. Final conductivity measurements were assumed to be attributed to ion capture and was therefore used to calculate a percent difference in conductivity (captured salt). The uptake of salt was correlated to the resulting decrease in conductivity by the following formula:

Uptake=(volume in mL*salinity*% Δ)/sample weight, where % Δ is the % change in conductivity. The % change in conductivity is attributed to a reduction in mass of NaCl in solution and is normalized to samples weight. The resulting measurement parameter yields salt uptake as g NaCl/g sample.

TABLE 43

Salt removal properties of a charge modified and cross linked biopolymer system.

| Sample # | Salt Uptake - Conductivity (g/g) | Salt Uptake - Ash Content (g/g) |
|---|---|---|
| 5.1A | 0.24 | 0.98 |
| 5.1B | 0.22 | 1.1 |
| 5.1C | 0.16 | 0.69 |
| 5.2A | 0.13 | N/A |
| 5.2B | 0.13 | N/A |
| 5.3A | N/A | 0.1 |
| 5.3B | 0.25 | 0.74 |
| 5.3C | 0.2 | N/A |
| 5.3D | 0.24 | N/A |

Here, salt uptake results of a cross linked biopolymer (cross-linked cationic starch as prepared via the method found in Example 4.2) as measured by conductivity show values of 0g/g. While not wishing to be bound to any particular theory, the presence of amphoteric charge (including both cationic and anionic charge simultaneously) is expected to improve the polymer's interaction with free ions in solution and is shown in Table 43. Data demonstrated the ability of charge modified and cross linked biopolymers to remove ions from solution at a greater rate than a cross-linked biopolymer. Salt uptake is further demonstrated through ash content measurements as shown in Table 43 above.

Example 7

Example of Modified Biopolymer for SAP Application (Demonstration of Charge Modified Starch (Cationic) Crosslinked to Form Superabsorbent A superabsorbent polymer was prepared using a commercially available charged cationic starch (AquaFlocc 330AW) and a catalyst on the P11 extruder described in Example 1.1. The extruder having multiple zones similar to that shown in FIG. 2, allows for implementation of temperature and injection profiles. Screw profile utilized is described in FIG. 6 (medium shear screw). Extrusion and composition parameters for preparing a material for super absorbent material were varied as described in Table 44. In preparing the super absorbent polymer, powder cationic starch (Aquafloc 330AW) and sodium hydroxide were fed into the initial injection zone via volumetric powder feeder (olumetric MiniTwin Process 11, Typ 567-7660, Thermo Electron/Thermo Fisher Scientific, Germany), while plasticizer (glycerol) was simultaneously added in at injection zone 2 via liquid injector and peristaltic pump (Masterflex P/S Peristaltic Pump, Model No 1300-3600-0004, Thermo Fisher Scientific, USA) with corresponding peristaltic pump head (Masterflex P/S Easy Load II, Model No 955-0000, Thermo Fisher Scientific, USA). In some runs, extruded samples in solid form were post-treated by placing the modified cationic polymer in an oven at 120° C. for 90 minutes. The simultaneous injection of two mixtures demonstrated below is defined as a 2-step, inline reaction.

In preparing the absorbent polymers, the following parameters were varied: temperature, screw rpm, plasticizer, plasticizer concentration, and amount of catalyst. Table 44 sets forth the ranges for the temperature, screw rpm, and amount of catalyst tested using the 11 mm, parallel twin screw extruder.

Samples were tested as absorbents using the EDANA/INDA method WSP 240.2.R3: free swell capacity in saline by gravimetric determination in order to measure the fluid uptake of samples. For the gravimetric method, 0.2 g of sample was sealed in a 2"×2" teabag. The teabag/sample packet was submerged in a solution for 1 hr, then hanged to dry for 10 mins. Solutions were prepared according to an industrially relevant application (0.9% NaCl). Weight measurements were recorded pre- and-post submerging and normalized for a teabag control sample undergoing the same conditions. The calculation was as follows:

$$\frac{W_w - W_b - W_i}{W_i}$$

where $W_w$ is the wet weight of the teabag/sample, $W_b$ is the wet weight of the teabag alone, and $W_i$ is the initial weight of the teabag/sample.

TABLE 44

Parameter ranges absorbent polymers via twin screw conical extruder.

| | |
|---|---|
| Temperature Ranges (° C.) | 80-160 |
| RPM Ranges (RPM) | 50-200 |
| Plasticizer | Water, Glycerol, PEG |
| Plasticizer (wt % relative to cat. Starch) | 20-60% |
| NaOH (wt % relative to cat. starch) | 0-30% |

Table 45 provides specific parameters tested with specific temperature profiles shown in Table 46 and test responses described in Table 47. Each sample was tested to determine its swelling capacity according to the method described above, and solubility according to the method in example 2.

TABLE 45

Process and formulation parameters for absorbent polymers.

| | Sample # | |
|---|---|---|
| | Sample 7A | Sample 7B |
| Temperature (° C.) | Temp Profile 7 | Temp Profile 7 |
| RPM | 150 | 80 |
| Post Treatment | Yes | Yes |
| Plasticizer (wt % relative to cat. starch) | Glycerol (25%) | Glycerol (25%) |
| NaOH (wt % relative to cat. starch) | 7.5% | 7.5% |

TABLE 46

Temperature and injection profiles for examples 7A and 7B: charge-modified starch via 11 mm, parallel twin-screw extruder.

| | | Zone | | | | | | | | |
|---|---|---|---|---|---|---|---|---|---|---|
| Sample # | | 1 | 2 | 3 | 4 | 5 | 6 | 7 | 8 | Die |
| | Temp Profile 7 (° C.) | Unheated | 70 | 75 | 80 | 95 | 110 | 100 | 100 | 100 |
| | Injection | Cat. Starch + NaOH | Glycerol | N/A | N/A | N/A | N/A | N/A | N/A | N/A |
| 7A | Feed Rate (RPM) | 50 | 5.9 | N/A | N/A | N/A | N/A | N/A | N/A | N/A |
| 7B | Feed Rate (RPM) | 25 | 2.4 | N/A | N/A | N/A | N/A | N/A | N/A | N/A |

TABLE 47

Properties of the absorbent polymers.

| Sample # | Free Swell Capacity (g/g) | Solubility (g/g) |
|---|---|---|
| 7A | 31.6 | 4.5 |
| 7B | 28.8 | 2.0 |

As shown by results in Table 47, reactive extrusion is used to make a biopolymer material that is useful for absorbing liquids in industrially relevant applications.

Example 8

Example of Modified Biopolymer for Biosorbent Application

Additionally, samples as described in Example 7 were tested as absorbents for other fluids using a modified the EDANA/INDA method WSP 240.2.R3: free swell capacity in saline by gravimetric determination in order to measure the fluid uptake of samples. Here, alternative solutions are used as shown in Table 48, in place of the specified 0.9% NaCl (saline). Instant Ocean Seal Salt was used as a sea water stimulant. Canola oil, conventional motor oil, and synthetic motor oil, were used as oil references. Gasoline and diesel fuel were used as fuel references, and whole bovine blood was used as a blood reference. The results demonstrated an improved performance for cross-linked, charge-modified biopolymers of the present invention relative to conventional superabsorbent materials: Sodium Polyacrylate (NaPoly, Item 432784, Sigma-Aldrich, St. Louis, Mo.) in Table 48 below.

TABLE 48

Biosorbent properties of a cross-linked, charge-modified biopolymer of the present invention ("Modified Biopolymer") relative to commercially available superabsorbent polymers (NaPoly).

| Solution | Sample | Uptake (g/g) |
|---|---|---|
| Instant Ocean (Sea Water) | Modified Biopolymer | 29 |
| | Na Poly | 19 |
| Canola Oil | Modified Biopolymer | 18 |
| | Na Poly | 2.2 |
| Motor Oil (Conventional) | Modified Biopolymer | 5.3 |
| | Na Poly | 1.7 |
| Motor Oil (Synthetic) | Modified Biopolymer | 9.2 |
| | Na Poly | 2.3 |
| Gasoline | Modified Biopolymer | 3.9 |
| | Na Poly | 0.8 |
| Diesel | Modified Biopolymer | 4.7 |
| | Na Poly | 3.4 |
| Blood | Modified Biopolymer | 16.6 |
| | Na Poly | 1.48 |

As shown by results in Table 48, reactive extrusion is used to make a biopolymer material that is useful for absorbing liquids in a range of industrially relevant applications.

Example 9

Example of Modified Biopolymer Showing Comparative Homogeneity (Homogeneity Analysis)

A JEOL JSM-6010LA scanning electron microscopy (SEM) with a solid state EDS detector was used to characterize and compare samples. Samples were adhered to a mount using double sided carbon tape and analyzed at 20kV. Micrographs were collected along with corresponding EDS scans of the target area.

Indications of homogeneity were derived from the comparison of commercially available cationic starch to an extruded cationic starch of the present invention (Example 2.2C). AquaFlocc 330AW manufactured by Aquasol Corp (Rock Hill, S.C.) represented the commercially available starch. It is believed that the commercially available cationic starch is modified in a dry process, which maintains starch in granular form and allows only for surface modification of the starch. In contrast, while not wishing to be bound to any particular theory, the extrusion process is believed to completely destroy the granular structure of the biopolymer (e.g., starch).

As can be seen in FIGS. 7A and 7B, which are SEM images of commercially available starch, the commercially available starch retains the starch's characteristic granular structure. In contrast, as can be seen in FIGS. 7D and 7E, which are SEM images of extruded cationic starch prepared according to methods of the present invention, starches extruded according to embodiments of the present invention exhibit complete destruction of the granular structure and morphology arises only from topology in sample preparation. This can be seen by comparing FIGS. 7A and 7B with FIGS. 7D and 7E.

Furthermore, when exposed to water and dried, the commercially available starches showed the presence of insoluble materials. These insoluble materials indicate uncharged or lowly charged regions, which are a product of inhomogeneous processing. These results were confirmed via Energy-Dispersive X-ray Spectroscopy (EDS of EDXS), which was used to map the elemental composition of the SEM image for the commercially available starch (FIG. 7C) and the extruded cationic starch prepared according to methods of the present invention (FIG. 7F). As can be seen in FIG. 7C, a clear/defined dark region is present where the discrete particles are imaged. This indicates that these particles are different in composition (lacking chlorine) compared to the surrounding region. In contrast, as can be seen in FIG. 7F, EDS scans of the extruded starch show a gradual change in contrast towards the bottom right of the image. This change correlates to a sloping region on the SEM image towards the bottom right. However, the top left of the image in FIG. 7F also shows a sloping region in the SEM image, with little change in the EDS map. Thus, it can be concluded that any contrast here is from a shadowing effect, rather than a compositional effect and the sample is therefore homogeneous.

The foregoing is illustrative of the present invention, and is not to be construed as limiting thereof. The invention is defined by the following claims, with equivalents of the claims to be included therein. All publications, patent applications, patents, patent publications, and other references cited herein are incorporated by reference in their entireties for the teachings relevant to the sentence and/or paragraph in which the reference is presented.

That which is claimed is:

1. A cross-linked, charged modified starch, wherein the cross-linked, charge modified starch includes at least one negatively charged moiety and the cross-linked charge modified starch is provided by reacting a starch with a charge-modifying agent including the at least one negatively charged moiety;

wherein the cross-linked, charge modified starch has a charge density of greater than 5 meq/g, as measured by titration, for the at least one negatively charged moiety;

wherein the cross-linked, charge modified starch has a net negative charge and is anionic;

wherein the at least one negatively charged moiety is a carboxyl, a sulfonate, a sulfate, and/or a phosphate group; and wherein the cross-linked, charge-modified starch comprises a plurality of void spaces formed therein having an average diameter of about 0.1 microns to about 500 microns.

2. The cross-linked, charge modified starch of claim 1, wherein the cross-linked, charge modified starch further comprises a biopolymer that is different than starch.

3. The cross-linked, charge modified starch of claim 1, wherein the at least one negatively charged moiety is a carboxyl, and the cross-linked, charge modified starch is covalently cross-linked.

4. The cross-linked, charge-modified starch of claim 1, wherein the cross-linked, charge modified starch has a charge density in a range of greater than 5 meq/g to 10 meq/g, as determined by titration.

5. A cross-linked, charge modified starch, wherein the cross-linked, charge modified starch includes at least one negatively charged moiety and charge modified starch is provided by reacting a starch with a charge-modifying agent including the at least one negatively charged moiety;

wherein the cross-linked, charge modified starch has a charge density of greater than 5 meq/g, as measured by titration, for the at least one negatively charged moiety;

wherein the cross-linked, charge modified starch has a net negative charge and is anionic;

wherein the at least one negatively charged moiety is a carboxyl, a sulfonate, a sulfate, and/or a phosphate group, and wherein the cross-linked, charge-modified starch is in the form of a particle having a diameter in a range of about 1 micron to about 2,000 microns.

6. The cross-linked, charge modified starch of claim 5, further comprising a biopolymer that is different than starch.

7. The cross-linked, charge modified starch of claim 5, wherein the cross-linked, charge-modified starch is in the form of a particle having a diameter in a range of about 10 microns to about 1000 microns.

8. The cross-linked, charge-modified starch of claim 5, wherein the cross-linked, charge modified starch has a charge density in a range of greater than 5 meq/g to 10 meq/g, as determined by titration.

9. The cross-linked, charge-modified starch of claim 5, wherein the cross-linked, charge modified starch has a charge density in a range of greater than 5 meq/g to 7 meq/g, as determined by titration.

10. The cross-linked, charge-modified starch of claim 5, wherein the at least one negatively charged moiety is a carboxyl group.

11. The cross-linked, charge-modified starch of claim 5, wherein the charge-modifying agent is selected from the group consisting of an acid, a mono-halogen substituted fatty acid, an acetate, an anhydride, an alkyl ester of acrylic acid, crotonic acid or itaconic acid, an acrylonitrile, sodium periodate, a sulfone, a sulfonic acid, and any combination thereof.

12. The cross-linked, charge-modified starch of claim 5, wherein the charge-modifying agent comprises a carboxylic acid group.

13. The cross-linked, charge-modified starch of claim 5, wherein the charge-modifying agent reacts with a hydroxyl group of the starch.

14. The cross-linked, charge-modified starch of claim 5, wherein the cross-linked, charge-modified starch is covalently cross-linked.

15. The cross-linked, charge modified starch of claim 5, wherein the cross-linked, charge modified starch is in the form of a particle having a diameter in a range of about 300 micron to about 800 micron.

16. The cross-linked, charge-modified starch of claim 5, wherein the at least one negatively charged moiety is a phosphate group.

17. A method for producing a cross-linked, charge-modified starch, the method comprising:
melting a starch in the presence of a plasticizer to form a homogeneous reaction blend, wherein the plasticizer comprises water in an amount of at least 20% by weight of the starch and the homogeneous reaction blend is a single, continuous phase that comprises a plasticized starch;
reacting the plasticized starch and a charge-modifying agent that includes at least one negatively charged moiety in the homogeneous reaction blend to form the charge-modified starch; and
cross-linking the charge-modified starch to form the cross-linked, charge-modified starch,
wherein the at least one negatively charge moiety is a carboxly, a sulfonate, a sulfate, and/or phosphate group; and
wherein the cross-linked, charge modified starch has a net negative charge, is anionic, and has a charge density of greater than 5 meq/q, as measured by titration, for the at least one negatively charged moiety.

18. The method of claim 17, wherein cross-linking the charge-modified starch comprises cross-linking the charge-modified starch in the homogeneous reaction blend to form the cross-linked, charge-modified starch.

19. The method of claim 17, wherein the melting step further comprises combining a catalyst with the starch and the plasticizer to form the homogeneous reaction blend.

20. The method of claim 17, wherein the cross-linking step further comprises reacting the charge-modified starch with at least one cross-linking agent.

21. The method of claim 17, wherein the reacting and cross- linking steps occur simultaneously.

22. The method of claim 17, further comprising foaming the cross-linked, charge-modified starch.

23. The method of claim 17, wherein the melting step comprises melt blending the starch and the plasticizer using a reactive extrusion process.

24. The method of claim 17, wherein the reacting and cross- linking steps are carried out using a reactive extrusion process.

25. The method of claim 17, wherein the method is carried out in an extruder.

26. The method of claim 25, wherein the method is a single-stage direct extrusion process.

27. The method of claim 25, wherein the extruder comprises at least two reaction zones.

28. The method of claim 27, wherein the method comprises reacting the plasticized starch and at least one charge-modifying agent at a first reaction zone and cross-linking the charge-modified starch at a second reaction zone.

29. The method of claim 25, wherein the method is a multi-stage extrusion process.

30. The method of claim 17, wherein the reacting and/or cross-linking step(s) is/are carried out at a temperature in a range of about 80° C. to about 150° C.

31. The method of claim 17, wherein the reacting and/or cross-linking step(s) is/are carried out in an extruder with a residence time in a range of about 0.1 minutes to about 5 minutes.

32. The method of claim 17, wherein the reacting and/or cross-linking step(s) is/are carried out in an extruder having a screw RPM in a range of about 250 to about 500.

33. The method of claim 17, further comprising heating the cross-linked, charge-modified starch at a temperature in a range of about 100° C. to about 150° C. for a period of time in a range of about 1 minute to about 8 hours.

34. The method of claim 17, wherein the cross-linked, charge-modified starch is in the form of a particle wherein the cross-linked, charge-modified starch is in the form of a particle having a diameter in a range of about 1 micron to about 2,000 microns.

35. The method of claim 34, wherein the cross-linked, charge-modified starch is in the form of a particle having a diameter in a range of about 300 microns to about 800 microns.

36. The method of claim 17, wherein the at least one negatively charged moiety is a carboxyl, and the cross-linked, charge modified starch is covalently cross-linked.

37. The method of claim 17, wherein the cross-linked, charge modified starch further comprises a biopolymer that is different than starch.

38. The method of claim 17, wherein the cross-linked, charge modified starch has a charge density in a range of greater than 5 meq/g to 10 meq/g, as determined by titration.

39. A cross-linked, charge modified starch, wherein the cross-linked, charge modified starch includes at least one negatively charged moiety and the cross-linked, charge modified starch is provided by reacting a starch with a charge-modifying agent including the at least one negatively charged moiety;
wherein the cross-linked, charge modified starch has a charge density of greater than 5 meq/g, as measured by titration, for the at least one negatively charged moiety;
wherein the cross-linked, charge modified starch has a net negative charge and is anionic; wherein the at least one negatively charged moiety is a carboxyl, a sulfonate, and/or a phosphate group; and
wherein the cross-linked, charge-modified starch absorbs a 0.9% saline soluation, at room temperature, in an amount of at least 20times the weight of the cross-linked, charge-modified starch.

40. The cross-linked, charge modified starch of claim 39, wherein the cross-linked, charge modified starch further comprises a biopolymer that is different than starch.

41. The cross-linked, charge-modified starch of claim 39, wherein the at least one negatively charged moiety is a carboxyl, and the cross-linked, charge modified starch is covalently cross-linked.

42. The cross-linked, charge-modified starch of claim 39, wherein the cross-linked, charge modified starch has a charge density in a range of greater than 5 meq/g to 10 meq/g, as determined by titration.

43. A cross-linked, charge modified starch, wherein the cross-linked, charge modified starch includes at least one negatively charged moiety and the cross-linked, charge modified starch includes at least one negatively charged moiety and the cross-linked, charge modified starch is provided by reacting a starch with a charge-modifying agent including, the at least one negatively charged moiety;
- wherein the cross-linked, charge modified starch has a charge density of greater than 5 meq/g, as measured by titration, for the at least one negativey charged moiety;
- wherein the cross-linked, charge modified starch has a net negative charge and is anionic; wherein the at least one negatively charged moiety is a carboxyl, a sulfonate, a sulfate, and/or a phosphate group; and
- wherein the cross-linked, charge-modified starch has a free swell capacity (FSC) in a range of about 25 g/g to about 100 g/g.

44. The cross-linked, charge modified starch of claim 43, wherein the cross-linked, charge modified starch further comprises a biopolymer that is different than starch.

45. The cross-linked, charge modified starch of claim 43, wherein the at least one negatively charged moiety is a carboxyl, and the cross-linked, charge modified starch is covalently cross-linked.

46. The cross-linked, charge-modified starch of claim 43, wherein the c cross-linked, charge modified starch has a charge density in a range of greater than 5 meq/g to 10 meq/g, as determined by titration.

47. A cross-linked, charge modified starch, wherein the cross-linked, charge modified starch includes at least one negatively charged moiety and the cross-linked charge modified starch is provided by reacting a starch with a charge-modifying agent including the at least one negatively charged moiety;
- wherein the cross-linked, charge modified starch has a charge density of greater than 5 meq/g, as measured by titration, for the at least one negatively charged moiety;
- wherein the cross-linked, charge modified has a net negative charge and is anionic;
- wherein the at least one negatively charged moiety is a carboxly, a sulfonate, a sulfate, and/or a phosphate group; and
- wherein the cross-linked, charge-modified starch has a Centrifuge Retention Capacity (CRC) in a range of about 15 g/g to about 60 g/g.

48. The cross-linked, charge modified starch of claim 47, wherein the cross-linked, charge modified starch further comprises a biopolymer that is different than starch.

49. The cross-linked, charge modified starch of claim 47, wherein the at least one negatively charged moiety is a carboxyl, and the cross-linked, charge modified starch is covalently cross-linked.

50. The cross-linked, charge-modified starch of claim 47, wherein the cross-linked, charge modified starch has a charge density in a range of greater than 5 meq/g to 10 meq/g, as determined by titration.

* * * * *

UNITED STATES PATENT AND TRADEMARK OFFICE
CERTIFICATE OF CORRECTION

PATENT NO. : 10,982,013 B2
APPLICATION NO. : 14/728240
DATED : April 20, 2021
INVENTOR(S) : Ayoub et al.

It is certified that error appears in the above-identified patent and that said Letters Patent is hereby corrected as shown below:

On the Title Page

Item (56) References Cited, OTHER PUBLICATIONS, Column 2, Line 50, Alqnso cite:
Please correct "Alqnso" to read -- Alonzo --

Item (56) References Cited, U.S. PATENT DOCUMENTS, Page 2, Column 1, Line 12:
Please correct "Sinith" to read -- Smith --

Item (56) References Cited, FOREIGN PATENT DOCUMENTS, Page 3, Column 2, Line 50:
Please correct "WO 20071035099" to read -- WO 2007/035099 --

In the Specification

Column 11, Line 6: Please correct "(F)" to read -- ($F^-$) --

In the Claims

Column 51, Line 32, Claim 17:
Please correct "carboxly" to read -- carboxyl --

Column 51, Line 36, Claim 17:
Please correct "5 meq/q" to read -- 5 meq/g --

Column 52, Lines 17-18, Claim 34:
Please delete "wherein the cross-linked, charge-modified starch is in the form of a particle"

Column 52, Line 50, Claim 39:
Please correct "20times" to read -- 20 times --

Signed and Sealed this
Ninth Day of November, 2021

Drew Hirshfeld
*Performing the Functions and Duties of the*
*Under Secretary of Commerce for Intellectual Property and*
*Director of the United States Patent and Trademark Office*

CERTIFICATE OF CORRECTION (continued)
U.S. Pat. No. 10,982,013 B2

Column 52, Lines 66-67, Claim 43:
Please delete "includes at least one negatively charged moiety and the cross-linked, charge modified starch"

Column 53, Line 2, Claim 43:
Please correct "including, the" to read -- including the --

Column 53, Line 5, Claim 43:
Please correct "negativey" to read -- negatively --

Column 53, Line 21, Claim 46:
Please correct "the c cross-linked" to read -- the cross-linked --